US010590412B2

(12) United States Patent
Ward et al.

(10) Patent No.: US 10,590,412 B2
(45) Date of Patent: Mar. 17, 2020

(54) COMPOSITIONS AND METHODS FOR MODULATION NUCLEIC ACIDS THROUGH NONSENSE MEDIATED DECAY

(71) Applicant: Ionis Pharmaceuticals, Inc., Carlsbad, CA (US)

(72) Inventors: Amanda Ward, Cambridge, MA (US); Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 70 days.

(21) Appl. No.: 14/785,411

(22) PCT Filed: Apr. 21, 2014

(86) PCT No.: PCT/US2014/034768
§ 371 (c)(1),
(2) Date: Oct. 19, 2015

(87) PCT Pub. No.: WO2014/172698
PCT Pub. Date: Oct. 23, 2014

(65) Prior Publication Data
US 2016/0076027 A1    Mar. 17, 2016

Related U.S. Application Data

(60) Provisional application No. 61/946,591, filed on Feb. 28, 2014, provisional application No. 61/814,139, filed on Apr. 19, 2013.

(51) Int. Cl.
*C12N 15/113* (2010.01)

(52) U.S. Cl.
CPC ........ *C12N 15/113* (2013.01); *C12N 2310/11* (2013.01); *C12N 2310/321* (2013.01); *C12N 2310/322* (2013.01); *C12N 2310/3231* (2013.01); *C12N 2310/3341* (2013.01); *C12N 2310/346* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,138,045 A | 8/1992 | Cook et al. |
| 5,214,136 A | 5/1993 | Lin et al. |
| 5,218,105 A | 6/1993 | Cook et al. |
| 5,245,022 A | 9/1993 | Weis et al. |
| 5,254,469 A | 10/1993 | Miln et al. |
| 5,258,506 A | 11/1993 | Ureda et al. |
| 5,262,536 A | 11/1993 | Hobbs |
| 5,272,250 A | 12/1993 | Spielvogel et al. |
| 5,292,873 A | 3/1994 | Rokita et al. |
| 5,317,098 A | 5/1994 | Shizuya et al. |
| 5,319,080 A | 6/1994 | Leumann |
| 5,359,044 A | 10/1994 | Cook et al. |
| 5,371,241 A | 12/1994 | Brush |
| 5,391,723 A | 2/1995 | Priest |
| 5,393,878 A | 2/1995 | Leumann |
| 5,414,077 A | 5/1995 | Lin et al. |
| 5,416,203 A | 5/1995 | Letsinger |
| 5,446,137 A | 8/1995 | Maag et al. |
| 5,451,463 A | 9/1995 | Nelson et al. |
| 5,466,786 A | 11/1995 | Buhr et al. |
| 5,486,603 A | 1/1996 | Buhr |
| 5,510,475 A | 4/1996 | Agrawal et al. |
| 5,512,439 A | 4/1996 | Hornes et al. |
| 5,512,667 A | 4/1996 | Reed et al. |

(Continued)

FOREIGN PATENT DOCUMENTS

| | | |
|---|---|---|
| WO | WO 1994/026887 | 11/1994 |
| WO | WO 1997/026270 | 7/1997 |

(Continued)

OTHER PUBLICATIONS

Akinc et al., "A combination library of lipid-like materials for delivery of RNAi therapeutics" Nature Biotechnology (2008) 26:561-569.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16: 917-926.

Altmann et al., "Second Generation of Antisense Oligonucleotides: From Nuclease Resistance to Biological Efficacy in Animals" Chimia (1996) 50: 168-176.

(Continued)

*Primary Examiner* — J. E Angell
(74) *Attorney, Agent, or Firm* — McNeill Baur PLLC

(57) ABSTRACT

Disclosed herein are compounds, compositions and methods for modulating the amount or activity of a target nucleic acid. In certain embodiments, the amount or activity of a target nucleic acid is modulated through nonsense mediated decay.

12 Claims, 1 Drawing Sheet
Specification includes a Sequence Listing.

(56) References Cited

U.S. PATENT DOCUMENTS

| | | | |
|---|---|---|---|
| 5,514,785 | A | 5/1996 | Van Ness et al. |
| 5,519,134 | A | 5/1996 | Acevedo et al. |
| 5,525,465 | A | 6/1996 | Haralambidis et al. |
| 5,541,313 | A | 7/1996 | Ruth |
| 5,545,730 | A | 8/1996 | Ureda et al. |
| 5,552,538 | A | 9/1996 | Ureda et al. |
| 5,565,552 | A | 10/1996 | Magda et al. |
| 5,567,810 | A | 10/1996 | Weis et al. |
| 5,567,811 | A | 10/1996 | Misiura et al. |
| 5,574,142 | A | 11/1996 | Meyer, Jr. et al. |
| 5,576,427 | A | 11/1996 | Cook et al. |
| 5,578,717 | A | 11/1996 | Ureda et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,371 | A | 12/1996 | Sessler et al. |
| 5,591,584 | A | 1/1997 | Chang et al. |
| 5,591,722 | A | 1/1997 | Montgomery et al. |
| 5,595,726 | A | 1/1997 | Magda et al. |
| 5,597,696 | A | 1/1997 | Lin et al. |
| 5,597,909 | A | 1/1997 | Ureda et al. |
| 5,599,923 | A | 2/1997 | Sessler et al. |
| 5,599,928 | A | 2/1997 | Hemmi et al. |
| 5,608,046 | A | 3/1997 | Cook et al. |
| 5,610,300 | A | 3/1997 | Altmann et al. |
| 5,627,053 | A | 5/1997 | Usman et al. |
| 5,627,274 | A | 5/1997 | Kole et al. |
| 5,639,873 | A | 6/1997 | Barascut et al. |
| 5,646,265 | A | 7/1997 | McGee |
| 5,658,873 | A | 8/1997 | Bertsch-Frank et al. |
| 5,665,593 | A | 9/1997 | Kole et al. |
| 5,670,633 | A | 9/1997 | Cook et al. |
| 5,688,941 | A | 11/1997 | Cook et al. |
| 5,700,920 | A | 12/1997 | Altmann et al. |
| 5,792,747 | A | 8/1998 | Schally et al. |
| 5,916,808 | A | 6/1999 | Kole et al. |
| 5,976,879 | A | 11/1999 | Kole et al. |
| 6,172,216 | B1 | 1/2001 | Bennett et al. |
| 6,210,892 | B1 | 4/2001 | Bennett et al. |
| 6,214,986 | B1 | 4/2001 | Bennett et al. |
| 6,268,490 | B1 | 7/2001 | Imanishi et al. |
| 6,525,191 | B1 | 2/2003 | Ramasamy |
| 6,656,730 | B1 | 12/2003 | Manoharan |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel |
| 7,399,845 | B2 | 7/2008 | Seth et al. |
| 7,427,672 | B2 | 9/2008 | Imanishi et al. |
| 7,741,457 | B2 | 6/2010 | Seth et al. |
| 2004/0171570 | A1 | 9/2004 | Allerson et al. |
| 2005/0020525 | A1 | 1/2005 | McSwiggen et al. |
| 2005/0053965 | A1* | 3/2005 | Baker ............. C07H 21/02 435/6.18 |
| 2005/0054836 | A1 | 3/2005 | Kminer et al. |
| 2005/0074801 | A1 | 4/2005 | Monia et al. |
| 2005/0130923 | A1 | 6/2005 | Bhat et al. |
| 2006/0172962 | A1 | 8/2006 | Vickers et al. |
| 2007/0105807 | A1 | 3/2007 | Sazani et al. |
| 2007/0287831 | A1 | 12/2007 | Seth et al. |
| 2008/0039618 | A1 | 2/2008 | Allerson et al. |

FOREIGN PATENT DOCUMENTS

| | | |
|---|---|---|
| WO | WO 1999/014226 | 3/1999 |
| WO | WO 2003/004602 | 1/2003 |
| WO | WO 2004/106356 | 12/2004 |
| WO | WO 2005/021570 | 3/2005 |
| WO | WO 2007/002390 | 1/2007 |
| WO | WO 2007/047913 | 4/2007 |
| WO | WO 2007/090073 | 8/2007 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036698 | 4/2010 |
| WO | WO 2010/048585 | 4/2010 |
| WO | WO 2011/017521 | 2/2011 |
| WO | WO 2013/022990 | 2/2013 |

OTHER PUBLICATIONS

Altmann et al., "Second-generation antisense oligonucleotides: structure-activity relationships and the design of improved signal-transduction inhibitors." Biochem. Soc. Trans. (1996) 24: 630-637.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem., (1997) 272: 11944-12000.

Baker et al., "Nonsense-mediated mRNA decay: terminating erroneous gene express", Current Opinion in Cell Biology (2004) 16(3):293-299.

Beaucage et al., "The Synthesis of Specific Ribonucleotides and Unrelated Phosphoiylated Biomolecules by the Phosphoramidite Method" Tetrahedron (1993) 49(46):10441-10488.

Braasch et al., "Locked nucleic acid (LNA): fine-tuning the recognition of DNA and RNA" Chem. Biol. (2001) 8:1-7.

Cartegni et al., "Listening to silence and understanding nonsense: exonic mutations that affect splicing" Nat. Rev. Genet. (2002) 3(4): 285-298.

Crooke et al., "Pharmacokinetic Properties of Several Novel Oligonucleotide Analogs in mice" J. Pharmacol. Exp. Ther. (1996) 277(2):923-937.

Elayadi et al., "Application of PNA and LNA oligomers to chemotherapy" Curr. Opinion Invens. Drugs (2001) 2:558-561.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Hovhannisyan et al., "A Nove Intronic cis Element, ISE/ISS-3, Regulates Rat Fibroblast Growth Factor Receptor 2 Splicing through Activiation of an Upstream Exon and Repression of a Downstream Exon Containing a Noncanonical Branch Point Sequence" Mol. Cell. Biol. (2005) 25(1):250-263.

Hua et al., "Antisens Masking of an hnRNP A1/A2 Intronic Splicing Silencer Corrects SMN2 Splicing in Transgenic Mice" American J. of Human Genetics (2008) 82:1-15.

Hua et al., "Enhancement of SMN2 Exon 7 Inclusion by Antisense Oligonucleotides Targeting the Exon" PLoS Biol (2007) 5(4):e73.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.

Kole, "Modification of pre-mRNA splicing by antisense oligonucleotides" Acta Biochimica Polonica (1997) 44:231-238.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Krawczak et al., "The mutational spectrum of single base-pair substitutions in mRNA splice junctions of human genes: causes and consequences" Hum. Genet. (1992) 90:41-54.

Kumar et al., "The first analogues of LNA (locked nucleic acids): phosphorothioate-LNA and 2'-thio-LNA" Bioorg Med Chem Lett. (1998) 8:2219-2222.

Letsinger et al., "Cholesteiyl-conjugated oligonucleotides: Synthesis, properties, and activity as inhibitors of replication of human immunodeficiency virus in cell culture" PNAS (1989) 86:6553-6556.

(56) References Cited

OTHER PUBLICATIONS

Leumann et al., "DNA Analogues: From Supramolecular Principles to Biological Properties" Bioorganic & Medicinal Chemistry (2002) 10:841-854.

Manoharan et al., "Chemical Modifications to Improve Uptake and Bioavailability of Antisense Oligonucleotides" Ann. N.Y. Acad. Sci. (1992) 660: 306-309.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Cholic Acid-Oligonucleotide Conjugates for Antisense Applications" Bioorg. Med. Chem. Lett. (1994) 4:1053-1060.

Manoharan et al., "Oligonucleotide Conjugates: Alteration of the Pharmacokinetic Properties of Antisense Agents" Nucleosides & Nucleotides (1995) 14(3-5):969-973.

Manoharan et al., "Lipidic Nucleic Acids" Tetrahedron Lett. (1995) 36(21):3651-3654.

Martin, "Ein neuer Zugang zu 2'-O-Alkylribonucleosiden and Eigenschaften deren Oligonucleotide" Helv. Chim. Acta (1995) 78: 486-504.

Minovitsky et al., "The splicing regulatory element, UGCAUG, is phylogenetically and spatially conserved in introns that flank tissue-specific alternative exons" Nucleic Acids Res. (2005) 33(2):714-724.

Mishra et al., "Improved leishmanicidal effect of phosphorotioate antisense oligonucleotides by LDL-mediated delivery" Biochim. Biophys. Acta (1995) 1264:229-237.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Orum et al., "Locked nucleic acids: A promising molecular family for gene-function analysis and antisense drug development" Curr. Opinion Mol. Ther. (2001) 3:239-243.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Scamborova et al., "An Intronic Enhancer Regulates Splicing of the Twintron of *Drosophila melanogaster* prospero Pre-mRNA by Two Different Spliceosomes" Mol. Cell. Biol. (2004) 24(5):1855-1869.

Shea et al., "Synthesis, hybridization properties and antiviral activity of lipid-oligodeoxynucleotide conjugates" Nucl. Acids Res. (1990) 18(13):3777-3783.

Singh et al., "LNA (locked nucleic acids): synthesis and high-affinity nucleic acid recognition" Chem. Commun. (1998) 4:455-456.

Singh et al., "Synthesis of 2'-amino-LNA: A novel conformationally restricted high-affinity oligonucleotide analogue with a handle" J. Org. Chem. (1998) 63: 10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Taylor et al., "Induction of endogenous Bcl-xS through the control of Bcl-x pre-mRNA splicing by antisense oligonucleotides" Nat. Biotechnol. (1999) 17:1097-1100.

Vickers et al., "Modification of MyD88 mRNA splicing and inhibition of IL-1beta signaling in cell culture and in mice with a 2'-O-methoxyethyl-modified oligonucleotide" J. Immunol. (2006) 176(6):3652-61.

Wahlestedt et al., "Potent and nontoxic antisense oligonucleotide containing locked nucleic acids" Proc. Natl. Acad. Sci. USA (2000) 97: 5633-5638.

Ward et al, "Nonsense-mediated decas as a termination mechanism for antisense oligonucleotides" Nucleic Acids Research (2014) 42(9):5871-5879.

Wilton et al., "Specific removal of the nonsense mutation from the mdx dystrophin mRNA using antisense oligonucleotides" Neuromuscul. Disord., (1999) 9:330-338.

Yeo et al. "Variation in sequence and organization of splicing regulatory elements in vertebrate genes" Proc. Natl. Acad. Sci. (2004) 101(44):15700-15705.

Zammarchi et al., "Antitumorigenic potential of STAT3 alternative splicing modulation" PNAS (2011) 108(43):17779-84.

Lefave et al., "Splicing factor hnRNPH drives an oncogenic splicing switch in gliomas" EMBO Journal (2011) 30(19): 4084-4097.

Shi et al, "Antisense-Oligonucleotide Mediated Exon Skipping in Activin-Receptor-Like Kinase 2: Inhibiting the Receptor That Is Overactive in Fibrodysplasia Ossificans Progressiva" PLOS (2013) 8(7):1-18.

* cited by examiner

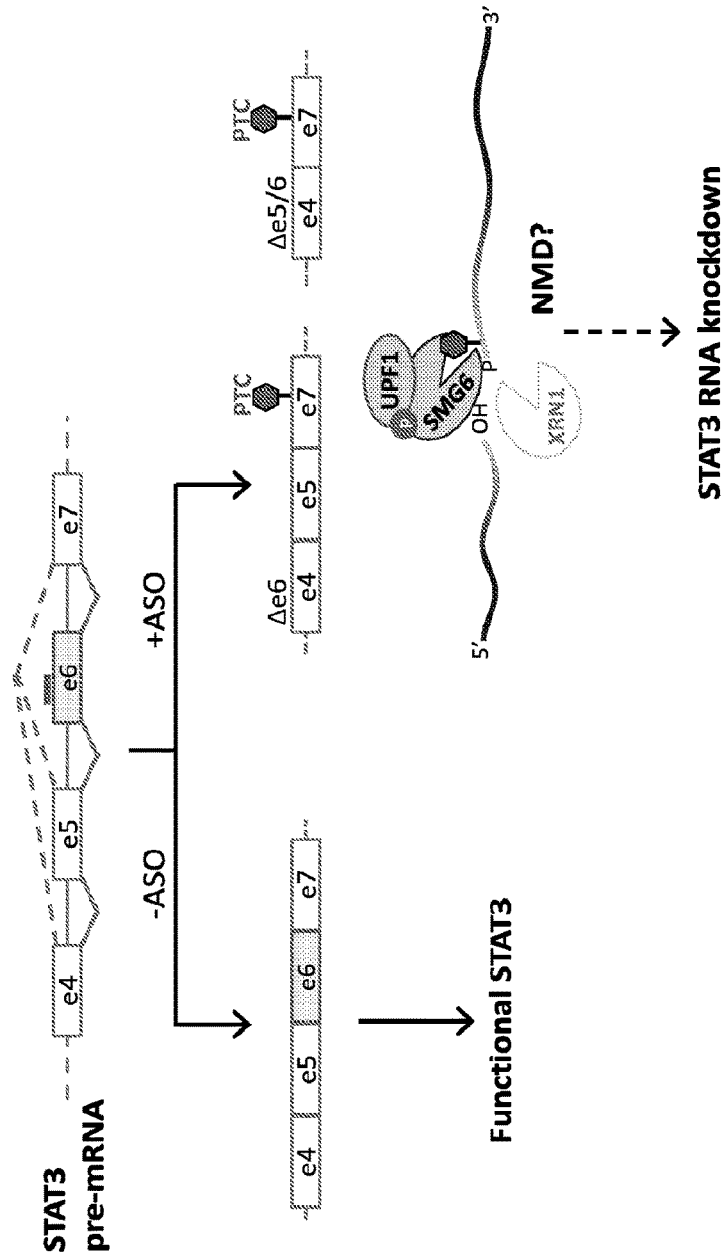

SEQUENCE LISTING

<160> NUMBER OF SEQ ID NOS: 173

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
acatgccact tggtgtttc ataa                                    24

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
tcttcgtaga ttgtgctgat agagaac                                27

<210> SEQ ID NO 3
<211> LENGTH: 29
<212> TYPE: DNA
<213> ORGANISM: Artificial Sequence
<220> FEATURE:
<223> OTHER INFORMATION: Probe

<400> SEQUENCE: 3
cagtatagcc gcttcctgca agagtcgaa                              29

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
cagcagatca agtccaggga                                        20

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
ctgtttaaaa taagcaaa                                          18

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
atcctgttta aaataagc                                          18

<210> SEQ ID NO 7
<211> LENGTH: 18
<212> TYPE: DNA
<213> ORGANISM: Artificial Sequence

```
<220> FEATURE:
<223> OTHER INFORMATION: Synthetic oligonucleotide

<400> SEQUENCE: 7
tagatcctgt ttaaaata                                                18

<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 8
ttctagatcc tgtttaaa                                                18

<210> SEQ ID NO 9
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 9
ctgttctaga tcctgttt                                                18

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 10
tttctgttct agatcctg                                                18

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
cattttctgt tctagatc                                                18

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 12
tttcattttc tgttctag                                                18

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
cactttcatt ttctgttc                                                18
```

```
<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
taccactttc attttctg                                                 18

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 15
ctctaccact ttcatttt                                                 18

<210> SEQ ID NO 16
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 16
attctctacc actttcat                                                 18

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 17
gagattctct accacttt                                                 18

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 18
ctggagattc tctaccac                                                 18

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 19
atcctggaga ttctctac                                                 18

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide
```

```
<400> SEQUENCE: 20
gtcatcctgg agattctc                                                 18

<210> SEQ ID NO 21
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 21
aaagtcatcc tggagatt                                                 18

<210> SEQ ID NO 22
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 22
atcaaagtca tcctggag                                                 18

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 23
gaaatcaaag tcatcctg                                                 18

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 24
gttgaaatca aagtcatc                                                 18

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 25
atagttgaaa tcaaagtc                                                 18

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 26
tttatagttg aaatcaaa                                                 18

<210> SEQ ID NO 27
```

```
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 27
ggttttatag ttgaaatc                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 28
gagggtttta tagttgaa                                                 18

<210> SEQ ID NO 29
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 29
cttgagggtt ttatagtt                                                 18

<210> SEQ ID NO 30
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 30
actcttgagg gttttata                                                 18

<210> SEQ ID NO 31
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 31
ttgactcttg agggtttt                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 32
tccttgactc ttgagggt                                                 18

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 33
```
gcctccttga ctcttgag					18

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 34
cttgcctcct tgactctt					18

<210> SEQ ID NO 35
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 35
tcacttgcct ccttgact					18

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 36
tattcacttg cctccttg					18

<210> SEQ ID NO 37
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 37
taatattcac ttgcctcc					18

<210> SEQ ID NO 38
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 38
ctctaatatt cacttgcc					18

<210> SEQ ID NO 39
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 39
catctctaat attcactt					18

<210> SEQ ID NO 40
<211> LENGTH: 18
<212> TYPE: DNA

```
<213> ORGANISM: Artificial Sequence
<220> FEATURE:
<223> OTHER INFORMATION: Synthetic oligonucleotide

<400> SEQUENCE: 40
taacatctct aatattca                                              18

<210> SEQ ID NO 41
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 41
ttttaacatc tctaatat                                              18

<210> SEQ ID NO 42
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 42
agattttaac atctctaa                                              18

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 43
tagagatttt aacatctc                                              18

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 44
ttctagagat tttaacat                                              18

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
ttggcttctc aagatacctg                                            20

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
acatgccact ttggtgtttc ataa                                       24
```

<210> SEQ ID NO 47
<211> LENGTH: 27
<212> TYPE: DNA
<213> ORGANISM: Artificial Sequence
<220> FEATURE:
<223> OTHER INFORMATION: Primer

<400> SEQUENCE: 47
tcttcgtaga ttgtgctgat agagaac                                27

<210> SEQ ID NO 48
<211> LENGTH: 29
<212> TYPE: DNA
<213> ORGANISM: Artificial Sequence
<220> FEATURE:
<223> OTHER INFORMATION: Probe

<400> SEQUENCE: 48
cagtatagcc gcttcctgca agagtcgaa                              29

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
gaagaggcgg caacagattg                                        20

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
ttctagccga tctaggcaga tgt                                    23

<210> SEQ ID NO 51
<211> LENGTH: 19
<212> TYPE: DNA
<213> ORGANISM: Artificial Sequence
<220> FEATURE:
<223> OTHER INFORMATION: Probe

<400> SEQUENCE: 51
ctgcattgga ggcccgccc                                         19

<210> SEQ ID NO 52
<211> LENGTH: 25
<212> TYPE: DNA
<213> ORGANISM: Artificial Sequence
<220> FEATURE:
<223> OTHER INFORMATION: Primer

<400> SEQUENCE: 52
aagtttatct gtgtgacacc aacga                                  25

<210> SEQ ID NO 53
<211> LENGTH: 25
<212> TYPE: DNA
<213> ORGANISM: Artificial Sequence
<220> FEATURE:

<223> OTHER INFORMATION: Primer

<400> SEQUENCE: 53
cttcaccatt atttccaaac tgcat                                    25

<210> SEQ ID NO 54
<211> LENGTH: 18
<212> TYPE: DNA
<213> ORGANISM: Artificial Sequence
<220> FEATURE:
<223> OTHER INFORMATION: Probe

<400> SEQUENCE: 54
tgccgatgtc ccccgca                                             18

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
tggagcagca ccttcaggat gt                                       22

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
tccagcgcag tgagcatctg tt                                       22

<210> SEQ ID NO 57
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 57
gaugcaguuc cgcuccauut t                                        21

<210> SEQ ID NO 58
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 58
gcugcagguu acuuacaagt t                                        21

<210> SEQ ID NO 59
<211> LENGTH: 21
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 59
agaugaacuu accguagaat t                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 60
gcugcagguu acuuacaagt t                                              21

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 61
gaugcaguuc cgcuccauut t                                              21

<210> SEQ ID NO 62
<211> LENGTH: 25
<212> TYPE: DNA
<213> ORGANISM: Artificial Sequence
<220> FEATURE:
<223> OTHER INFORMATION: Primer

<400> SEQUENCE: 62
gagcagtgaa cagcagctac tacag                                          25

<210> SEQ ID NO 63
<211> LENGTH: 24
<212> TYPE: DNA
<213> ORGANISM: Artificial Sequence
<220> FEATURE:
<223> OTHER INFORMATION: Primer

<400> SEQUENCE: 63
tgaccaagag tcagtgatca ggat                                           24

<210> SEQ ID NO 64
<211> LENGTH: 23
<212> TYPE: DNA
<213> ORGANISM: Artificial Sequence
<220> FEATURE:
<223> OTHER INFORMATION: Probe

<400> SEQUENCE: 64
ccgtgcatct atgggcgtga acg                                            23
```

```
<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
agcttcactg ttacatccta                                               20

<210> SEQ ID NO 66
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 66
ttcaacccaa ggacaaat                                                 18

<210> SEQ ID NO 67
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 67
acccttcaac ccaaggac                                                 18

<210> SEQ ID NO 68
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 68
tccaacccct caacccaa                                                 18

<210> SEQ ID NO 69
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 69
gatttccaac ccttcaac                                                 18

<210> SEQ ID NO 70
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 70
gcacgatttc caaccctt                                                 18

<210> SEQ ID NO 71
<211> LENGTH: 18
<212> TYPE: DNA
<213> ORGANISM: Artificial Sequence
<220> FEATURE:
<223> OTHER INFORMATION: Synthetic oligonucleotide
```

<400> SEQUENCE: 71
tttggcacga tttccaac                                              18

<210> SEQ ID NO 72
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 72
cccatttggc acgatttc                                              18

<210> SEQ ID NO 73
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 73
ttatcccatt tggcacga                                              18

<210> SEQ ID NO 74
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 74
aatgttatcc catttggc                                              18

<210> SEQ ID NO 75
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 75
cggcaatgtt atcccatt                                              18

<210> SEQ ID NO 76
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 76
ccaccggcaa tgttatcc                                              18

<210> SEQ ID NO 77
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 77
aagtccaccg gcaatgtt                                              18

<210> SEQ ID NO 78

```
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 78
ctggaagtcc accggcaa                                                 18

<210> SEQ ID NO 79
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 79
tcccctggaa gtccaccg                                                 18

<210> SEQ ID NO 80
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 80
ctcctcccct ggaagtcc                                                 18

<210> SEQ ID NO 81
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 81
cgtactcctc ccctggaa                                                 18

<210> SEQ ID NO 82
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 82
cccccgtact cctcccct                                                 18

<210> SEQ ID NO 83
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 83
gcctcccccg tactcctc                                                 18

<210> SEQ ID NO 84
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 84
```

```
gaaggcctcc cccgtact                                              18
```

<210> SEQ ID NO 85
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 85

```
gcacgaaggc ctcccccg                                              18
```

<210> SEQ ID NO 86
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 86

```
aactgcacga aggcctcc                                              18
```

<210> SEQ ID NO 87
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 87

```
agcaaactgc acgaaggc                                              18
```

<210> SEQ ID NO 88
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 88

```
gtgaagcaaa ctgcacga                                              18
```

<210> SEQ ID NO 89
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 89

```
tcctgtgaag caaactgc                                              18
```

<210> SEQ ID NO 90
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 90

```
tatttcctgt gaagcaaa                                              18
```

<210> SEQ ID NO 91
<211> LENGTH: 18
<212> TYPE: DNA

<213> ORGANISM: Artificial Sequence
<220> FEATURE:
<223> OTHER INFORMATION: Synthetic oligonucleotide

<400> SEQUENCE: 91
cagctatttc ctgtgaag                                                   18

<210> SEQ ID NO 92
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 92
ttttcagcta tttcctgt                                                   18

<210> SEQ ID NO 93
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 93
agccttttca gctatttc                                                   18

<210> SEQ ID NO 94
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 94
ttagagcctt ttcagcta                                                   18

<210> SEQ ID NO 95
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 95
ttctttagag ccttttca                                                   18

<210> SEQ ID NO 96
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 96
gtgtttcttt agagcctt                                                   18

<210> SEQ ID NO 97
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 97
ccttgtgttt ctttagag                                                   18

<210> SEQ ID NO 98
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 98
ctttccttgt gtttctttt                                          18

<210> SEQ ID NO 99
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 99
tattctttcc ttgtgttt                                           18

<210> SEQ ID NO 100
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 100
gccctattct ttccttgt                                           18

<210> SEQ ID NO 101
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 101
ctgtgcccta ttctttcc                                           18

<210> SEQ ID NO 102
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 102
ccacctgtgc cctattct                                           18

<210> SEQ ID NO 103
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 103
atccccacct gtgccta                                            18

<210> SEQ ID NO 104
<211> LENGTH: 18
<212> TYPE: DNA
<213> ORGANISM: Artificial Sequence
<220> FEATURE:

<223> OTHER INFORMATION: Synthetic oligonucleotide

<400> SEQUENCE: 104
atccatcccc acctgtgc                                                 18

<210> SEQ ID NO 105
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 105
aaccatccat ccccacct                                                 18

<210> SEQ ID NO 106
<211> LENGTH: 24
<212> TYPE: DNA
<213> ORGANISM: Artificial Sequence
<220> FEATURE:
<223> OTHER INFORMATION: Primer

<400> SEQUENCE: 106
tccaaatagt cctgacacgg ccaa                                          24

<210> SEQ ID NO 107
<211> LENGTH: 24
<212> TYPE: DNA
<213> ORGANISM: Artificial Sequence
<220> FEATURE:
<223> OTHER INFORMATION: Primer

<400> SEQUENCE: 107
tggccataag ctttcgtggt ggat                                          24

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
gaagcccttg ccagccatgt                                               20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
gactcttgca ggaatcggct                                               20

<210> SEQ ID NO 110
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 110
agttgaaatc aaagtcgt                                                 18

```
<210> SEQ ID NO 111
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 111
tcttgagggt tttgtagt                                                 18

<210> SEQ ID NO 112
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 112
agaagttcac gttctatt                                                 18

<210> SEQ ID NO 113
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 113
agtgaagaag ttcacgtt                                                 18

<210> SEQ ID NO 114
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 114
ggcttagtga agaagttc                                                 18

<210> SEQ ID NO 115
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 115
tccaattggc ggcttagt                                                 18

<210> SEQ ID NO 116
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 116
caggttccaa ttggcggc                                                 18

<210> SEQ ID NO 117
<211> LENGTH: 18
<212> TYPE: DNA
<213> ORGANISM: Artificial Sequence
<220> FEATURE:
<223> OTHER INFORMATION: Synthetic oligonucleotide
```

<400> SEQUENCE: 117
gtggtggacg agaactgc                                                    18

<210> SEQ ID NO 118
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 118
agtagttcac accaggcc                                                    18

<210> SEQ ID NO 119
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 119
ccgtcgccct tcagcacgca                                                  20

<210> SEQ ID NO 120
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 120
tgctcacctc tcttcatccg                                                  20

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
gcatacagag cgtgctgctc                                                  20

<210> SEQ ID NO 122
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 122
gtcctgacaa cacaactg                                                    18

<210> SEQ ID NO 123
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 123
ggacgtggaa cccatgct                                                    18

<210> SEQ ID NO 124
<211> LENGTH: 18

```
<212> TYPE: DNA
<213> ORGANISM: Artificial Sequence
<220> FEATURE:
<223> OTHER INFORMATION: Synthetic oligonucleotide

<400> SEQUENCE: 124
aggattaaaa tgaggtcc                                                     18

<210> SEQ ID NO 125
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 125
cttagagtga ggattaaa                                                     18

<210> SEQ ID NO 126
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 126
tttcttagag tgaggatt                                                     18

<210> SEQ ID NO 127
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 127
accatgtttc ttagagtg                                                     18

<210> SEQ ID NO 128
<211> LENGTH: 23
<212> TYPE: DNA
<213> ORGANISM: Artificial sequence
<220> FEATURE:
<223> OTHER INFORMATION: Primer

<400> SEQUENCE: 128
gccacgttgg tgtttcataa tct                                               23

<210> SEQ ID NO 129
<211> LENGTH: 24
<212> TYPE: DNA
<213> ORGANISM: Artificial sequence
<220> FEATURE:
<223> OTHER INFORMATION: Primer

<400> SEQUENCE: 129
gatagaggac attggactct tgca                                              24

<210> SEQ ID NO 130
<211> LENGTH: 29
<212> TYPE: DNA
<213> ORGANISM: Artificial sequence
<220> FEATURE:
<223> OTHER INFORMATION: Probe

<400> SEQUENCE: 130
```
ttgggtgaaa ttgaccagca atatagccg                                29

<210> SEQ ID NO 131
<211> LENGTH: 19
<212> TYPE: DNA
<213> ORGANISM: Artificial sequence
<220> FEATURE:
<223> OTHER INFORMATION: Primer

<400> SEQUENCE: 131 tttttgcgc ggtcctttc                                            19

<210> SEQ ID NO 132
<211> LENGTH: 22
<212> TYPE: DNA
<213> ORGANISM: Artificial sequence
<220> FEATURE:
<223> OTHER INFORMATION: Primer

<400> SEQUENCE: 132
gagggaccag agagagcaag ac                                       22

<210> SEQ ID NO 133
<211> LENGTH: 19
<212> TYPE: DNA
<213> ORGANISM: Artificial sequence
<220> FEATURE:
<223> OTHER INFORMATION: Probe

<400> SEQUENCE: 133
cgccttccgt ccgtcggct                                           19

<210> SEQ ID NO 134
<211> LENGTH: 22
<212> TYPE: DNA
<213> ORGANISM: Artificial sequence
<220> FEATURE:
<223> OTHER INFORMATION: Primer

<400> SEQUENCE: 134
tgcagggaac catccacttc ga                                       22

<210> SEQ ID NO 135
<211> LENGTH: 22
<212> TYPE: DNA
<213> ORGANISM: Artificial sequence
<220> FEATURE:
<223> OTHER INFORMATION: Primer

<400> SEQUENCE: 135
accgtccttt ccagcagtca ca                                       22

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
ttttgcatga tgtaaccact                                          20

<210> SEQ ID NO 137
<211> LENGTH: 23
<212> TYPE: DNA
<213> ORGANISM: Artificial sequence

```
<220> FEATURE:
<223> OTHER INFORMATION: Primer

<400> SEQUENCE: 137
gcagagtcgg gtgttagtgt tct                                    23

<210> SEQ ID NO 138
<211> LENGTH: 25
<212> TYPE: DNA
<213> ORGANISM: Artificial sequence
<220> FEATURE:
<223> OTHER INFORMATION: Primer

<400> SEQUENCE: 138
gctcacgggt aagtatacag agctt                                  25

<210> SEQ ID NO 139
<211> LENGTH: 29
<212> TYPE: DNA
<213> ORGANISM: Artificial sequence
<220> FEATURE:
<223> OTHER INFORMATION: Probe

<400> SEQUENCE: 139
tcctggaagc atctcttttc tcatttggc                              29

<210> SEQ ID NO 140
<211> LENGTH: 21
<212> TYPE: DNA
<213> ORGANISM: Artificial sequence
<220> FEATURE:
<223> OTHER INFORMATION: Primer

<400> SEQUENCE: 140
tgcagtgcct tctttcacat g                                      21

<210> SEQ ID NO 141
<211> LENGTH: 18
<212> TYPE: DNA
<213> ORGANISM: Artificial sequence
<220> FEATURE:
<223> OTHER INFORMATION: Primer

<400> SEQUENCE: 141
gggtgaggtg ggctgaga                                          18

<210> SEQ ID NO 142
<211> LENGTH: 30
<212> TYPE: DNA
<213> ORGANISM: Artificial sequence
<220> FEATURE:
<223> OTHER INFORMATION: Probe

<400> SEQUENCE: 142
catcatgctc tctgatccct caggttctgt                             30

<210> SEQ ID NO 143
<211> LENGTH: 21
<212> TYPE: DNA
<213> ORGANISM: Artificial sequence
<220> FEATURE:
<223> OTHER INFORMATION: Primer

<400> SEQUENCE: 143
gcagagggtg gacaactgaa c                                      21
```

<210> SEQ ID NO 144
<211> LENGTH: 23
<212> TYPE: DNA
<213> ORGANISM: Artificial sequence
<220> FEATURE:
<223> OTHER INFORMATION: Primer

<400> SEQUENCE: 144
gaggtcaact ccatgtcaaa ggt                                             23

<210> SEQ ID NO 145
<211> LENGTH: 29
<212> TYPE: DNA
<213> ORGANISM: Artificial sequence
<220> FEATURE:
<223> OTHER INFORMATION: Probe

<400> SEQUENCE: 145
agttttccct gtctgtccct ccagagtcc                                       29

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
aatcaaagtc atcctggaga                                                 20

<210> SEQ ID NO 147
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 147
aucaaaguca uccuggag                                                   18

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 148
caaagtcatc ctggag                                                     16

<210> SEQ ID NO 149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 149
atcaaagtca tcctgg                                                     16

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
tatagttgaa atcaaagtca                                               20

<210> SEQ ID NO 151
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 151
auaguugaaa ucaaaguc                                                 18

<210> SEQ ID NO 152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 152
agttgaaatc aaagtc                                                   16

<210> SEQ ID NO 153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 153
atagttgaaa tcaaag                                                   16

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
tggacgtgga acccatgctg                                               20

<210> SEQ ID NO 155
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 155
ggacguggaa cccaugcu                                                 18

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 156
acgtggaacc catgct                                                   16

<210> SEQ ID NO 157

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 157
ggacgtggaa cccatg                                                      16

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
tcttagagtg aggattaaaa                                                  20

<210> SEQ ID NO 159
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 159
cuuagaguga ggauuaaa                                                    18

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 160
tagagtgagg attaaa                                                      16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
cttagagtga ggatta                                                      16

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
aagcaaactg cacgaaggcc                                                  20

<210> SEQ ID NO 163
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 163
```
agcaaacugc acgaaggc                                                18

<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 164
caaactgcac gaaggc                                                  16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165
agcaaactgc acgaag                                                  16

<210> SEQ ID NO 166
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 166
tccaccggca atgttatccc                                              20

<210> SEQ ID NO 167
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 167
ccaccggcaa uguuaucc                                                18

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 168
accggcaatg ttatcc                                                  16

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 169
ccaccggcaa tgttat                                                  16

<210> SEQ ID NO 170
<211> LENGTH: 24
<212> TYPE: DNA

```
<213> ORGANISM: Artificial sequence
<220> FEATURE:
<223> OTHER INFORMATION: Primer

<400> SEQUENCE: 170
actccttgcc agttgtggtg atct                                          24

<210> SEQ ID NO 171
<211> LENGTH: 24
<212> TYPE: DNA
<213> ORGANISM: Artificial sequence
<220> FEATURE:
<223> OTHER INFORMATION: Primer

<400> SEQUENCE: 171
ttagcccatg tgatctgaca ccct                                          24

<210> SEQ ID NO 172
<211> LENGTH: 24
<212> TYPE: DNA
<213> ORGANISM: Artificial sequence
<220> FEATURE:
<223> OTHER INFORMATION: Primer

<400> SEQUENCE: 172
agtatagccg cttcctgcaa gagt                                          24

<210> SEQ ID NO 173
<211> LENGTH: 24
<212> TYPE: DNA
<213> ORGANISM: Artificial sequence
<220> FEATURE:
<223> OTHER INFORMATION: Primer

<400> SEQUENCE: 173
cgggtctgaa gttgagattc tgct                                          24
```

COMPOSITIONS AND METHODS FOR MODULATION NUCLEIC ACIDS THROUGH NONSENSE MEDIATED DECAY

SEQUENCE LISTING

The present application is being filed along with a Sequence Listing in electronic format. The Sequence Listing is provided as a file entitled CORE0114USASEQ_ST25.txt, created Oct. 19, 2015, which is 36 Kb in size. The information in the electronic format of the sequence listing is incorporated herein by reference in its entirety.

BACKGROUND OF THE INVENTION

Newly synthesized eukaryotic mRNA molecules, known as primary transcripts or pre-mRNA are processed before translation. Processing of the pre-mRNAs includes addition of a 5' methylated cap and an approximately 200-250 base poly(A) tail to the 3' end of the transcript. Processing of mRNA from pre-mRNA also frequently involves splicing of the pre-mRNA, which occurs in the maturation of 90-95% of mammalian mRNAs. Introns (or intervening sequences) are regions of a pre-mRNA (or the DNA encoding it) that are not included in the coding sequence of the mature mRNA. Exons are regions of a primary transcript that remain in the mature mRNA. The exons are spliced together to form the mature mRNA sequence. Splice junctions are also referred to as splice sites with the 5' side of the junction often called the "5' splice site," or "splice donor site" and the 3' side the "3' splice site" or "splice acceptor site." In splicing, the 3' end of an upstream exon is joined to the 5' end of the downstream exon. Thus the unspliced pre-mRNA has an exon/intron junction at the 5' end of an intron and an intron/exon junction at the 3' end of an intron. After the intron is removed, the exons are contiguous at what is sometimes referred to as the exon/exon junction or boundary in the mature mRNA. Alternative splicing, defined as the splicing together of different combinations of exons, often results in multiple mRNA transcripts from a single gene.

Up to 50% of human genetic diseases resulting from a point mutation result in aberrant pre-mRNA processing. Such point mutations can either disrupt a current splice site or create a new splice site, resulting in mRNA transcripts comprised of a different combination of exons or with deletions in exons. Point mutations also can result in activation of a cryptic splice site or disrupt regulatory cis elements (i.e. splicing enhancers or silencers) (Cartegni et al., Nat. Rev. Genet., 2002, 3, 285-298; Drawczak et al., Hum. Genet., 1992, 90, 41-54). Antisense oligonucleotides have been used to target mutations that lead to aberrant splicing in several genetic diseases in order to redirect splicing to give a desired splice product (Kole, *Acta Biochimica Polonica*, 1997, 44, 231-238).

Antisense compounds have also been used to alter the ratio of naturally occurring alternate splice variants such as the long and short forms of Bcl-x pre-mRNA (U.S. Pat. Nos. 6,172,216; 6,214,986; Taylor et al., Nat. Biotechnol. 1999, 17, 1097-1100) or to force skipping of specific exons containing premature termination codons (Wilton et al., Neuromuscul. Disord., 1999, 9, 330-338). U.S. Pat. No. 5,627,274 and WO 94/26887 disclose compositions and methods for combating aberrant splicing in a pre-mRNA molecule containing a mutation using antisense oligonucleotides which do not activate RNAse H.

Antisense technology is an effective means for modulating the expression of one or more specific gene products, including alternative splice products, and is uniquely useful in a number of therapeutic, diagnostic, and research applications. The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes involved in disease.

SUMMARY OF THE INVENTION

In certain embodiments, the present disclosure provides methods comprising contacting a cell with an oligomeric compound comprising a modified oligonucleotide complementary to a nucleic acid transcript. In certain embodiments, the present disclosure provides methods comprising contacting a cell with an oligomeric compound comprising a modified oligonucleotide that reducing the amount or activity of a nucleic acid transcript in a cell through nonsense mediated decay.

In certain embodiments, the present disclosure provides oligomeric compounds comprising modified oligonucleotides that reduce the amount or activity of a nucleic acid transcript in a cell through nonsense mediated decay.

The present disclosure provides the following non-limiting numbered embodiments:

Embodiment 1

A method of reducing the amount or activity of a target nucleic acid transcript in a cell through nonsense mediated decay, comprising contacting a cell with an oligomeric compound comprising a modified oligonucleotide, wherein the modified oligonucleotide consists of 10 to 30 linked modified nucleosides, and wherein the modified nucleosides are not morpholinos.

Embodiment 2

The method of any of embodiments 1 to 2, wherein the target nucleic acid transcript is pre-mRNA.

Embodiment 3

The method of any of embodiments 1 to 2, wherein the target nucleic acid transcript is mRNA.

Embodiment 4

The method of any of embodiments 1 to 4, wherein the oligomeric compound increases aberrant splicing of the pre-mRNA.

Embodiment 5

The method of any of embodiments 1 to 4, wherein the oligomeric compound increases inclusion of an exon into the mRNA.

Embodiment 6

The method of any of embodiments 1 to 4, wherein the oligomeric compound increases exclusion of an exon into the mRNA.

Embodiment 7

The method of any of embodiments 1 to 6, wherein the oligomeric compound introduces a premature termination codon into the mRNA.

Embodiment 8

The method of any of embodiments 1 to 7, wherein the oligomeric compound reduces the amount or activity of protein translated from the nucleic acid transcript.

Embodiment 9

The method of any of embodiments 1 to 7, wherein the oligomeric compound increases the amount of a non-functional protein isoform translated from the nucleic acid transcript.

Embodiment 10

The method of embodiments 1 to 9, wherein the oligomeric compound has a nucleobase sequence comprising an at least 8 nucleobase portion complementary to an equal length portion of the nucleic acid transcript.

Embodiment 11

The method of embodiments 1 to 9, wherein the oligomeric compound has a nucleobase sequence comprising an at least 10 nucleobase portion complementary to an equal length portion of the nucleic acid transcript.

Embodiment 12

The method of embodiments 1 to 9, wherein the oligomeric compound has a nucleobase sequence comprising an at least 12 nucleobase portion complementary to an equal length portion of the nucleic acid transcript.

Embodiment 13

The method of embodiments 1 to 9, wherein the oligomeric compound has a nucleobase sequence comprising an at least 14 nucleobase portion complementary to an equal length portion of the nucleic acid transcript.

Embodiment 14

The method of embodiments 1 to 9, wherein the oligomeric compound has a nucleobase sequence comprising an at least 16 nucleobase portion complementary to an equal length portion of the nucleic acid transcript.

Embodiment 15

The method of embodiments 1 to 9, wherein the oligomeric compound has a nucleobase sequence comprising an at least 18 nucleobase portion complementary to an equal length portion of the nucleic acid transcript.

Embodiment 16

The method of embodiments 1 to 9, wherein the oligomeric compound has a nucleobase sequence comprising an at least 20 nucleobase portion complementary to an equal length portion of the nucleic acid transcript.

Embodiment 17

The method of embodiments 1 to 16, wherein the oligomeric compound is at least 80% complementary to the nucleic acid transcript.

Embodiment 18

The method of embodiments 1 to 16, wherein the oligomeric compound is at least 90% complementary to the nucleic acid transcript.

Embodiment 19

The method of embodiments 1 to 16, wherein the oligomeric compound is at least 95% complementary to the nucleic acid transcript.

Embodiment 20

The method of embodiments 1 to 16, wherein the oligomeric compound is 100% complementary to the nucleic acid transcript.

Embodiment 21

The method of embodiments 1 to 20, wherein each modified nucleoside comprises a 2'-substituted sugar moiety.

Embodiment 22

The method of embodiments 1 to 20, wherein each modified nucleoside comprises a 2'-substituted sugar moiety, an unmodified 2'-deoxy sugar moiety, or a bicyclic sugar moiety.

Embodiment 23

The method of embodiments 1 to 20, wherein each modified nucleoside comprises a 2'-substituted sugar moiety or an unmodified 2'-deoxy sugar moiety.

Embodiment 24

The method of embodiments 1 to 20, wherein each modified nucleoside comprises a 2'-substituted sugar moiety or a bicyclic sugar moiety.

Embodiment 25

The method of embodiment 24, wherein the 2'-substituted sugar moiety is a 2'-MOE sugar moiety.

Embodiment 26

The method of embodiment 24, wherein the bicyclic sugar moiety is a cEt sugar moiety.

Embodiment 27

The method of embodiments 1 to 20, wherein each modified nucleoside comprises a bicyclic sugar moiety or an unmodified 2'-deoxy sugar moiety.

Embodiment 28

The method of embodiment 27, wherein the bicyclic sugar moiety is a cEt sugar moiety.

Embodiment 29

The method of embodiments 1 to 20, wherein each modified nucleoside comprises the same 2'-substituted sugar moiety.

Embodiment 30

The method of embodiments 1 to 20, wherein the modified oligonucleotide has an A-$B_2$-A-$B_2$-A-$B_2$-A-$B_2$-A-$B_2$-A motif, wherein each A comprises a bicyclic sugar moiety, and wherein each B is selected from a 2'-substituted sugar moiety and an unmodified 2'-deoxy sugar moiety.

Embodiment 31

The method of embodiments 1 to 20, wherein the modified oligonucleotide has an $A_2$-$B_2$-A-$B_2$-A-$B_2$-A-$B_2$-A-$B_2$-$A_2$ motif, wherein each A comprises a bicyclic sugar moiety, and wherein each B is selected from a 2'-substituted sugar moiety and an unmodified 2'-deoxy sugar moiety.

Embodiment 32

The method of embodiment 30 or 31, wherein each A is a cEt sugar moiety.

Embodiment 33

The method of embodiment 30 or 31, wherein each A is an LNA sugar moiety.

Embodiment 34

The method of any of embodiments 30 to 33, wherein each B is an unmodified 2'-deoxy sugar moiety.

Embodiment 35

The method of any of embodiments 30 to 33, wherein each B is a 2'-MOE sugar moiety.

Embodiment 36

The method of embodiments 1 to 35, wherein at least two modified nucleosides comprises different 2'-substituted sugar moieties.

Embodiment 37

The method of embodiments 21 to 23, wherein the 2'-substituted sugar moiety comprises a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, O—$(CH2)_2$—O—$N(R_m)(R_n)$ or O—$CH_2$—C(=O)—$N(R_m)(R_n)$, where each Rm and Rn is, independently, H, an amino protecting group or substituted or unsubstituted $C_1$-$C_{10}$ alkyl;

wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 38

The method of embodiment 37, wherein the 2'-substituted sugar moiety comprises a 2' substituent selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_1)(R_2)$, $O(CH_2)_2$—$ON(R_1)(R_2)$, $O(CH_2)_2$—$O(CH_2)_2$—$N(R_1)(R_2)$, $OCH_2C(=O)$—$N(R_1)(R_2)$, $OCH_2C(=O)$—$N(R_3)$—$(CH_2)_2$—$N(R_1)(R_2)$, and $O(CH_2)_2$—$N(R_3)$—$C(=NR_4)[N(R_1)(R_2)]$; wherein $R_1$, $R_2$, $R_3$ and $R_4$ are each, independently, H or $C_1$-$C_6$ alkyl.

Embodiment 39

The method of embodiment 38, wherein the 2' substituent is selected from among: a halogen, $OCH_3$, $OCF_3$, $OCH_2CH_3$, $OCH_2CF_3$, $OCH_2$—CH=$CH_2$, $O(CH_2)_2$—$OCH_3$ (MOE), $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$, and $OCH_2$—$N(H)$—$C(=NH)NH_2$.

Embodiment 40

The method of any of embodiments 1 to 23, wherein the 2' substituent is a 2'-MOE sugar moiety.

Embodiment 41

The method of any of embodiments 1 to 23, wherein the 2' substituent is a 2'-OMe sugar moiety.

Embodiment 42

The method of any of embodiments 1 to 23, wherein the 2' substituent is a 2'-F sugar moiety.

Embodiment 43

The method of any of embodiments 1 to 23, wherein the 2' substituent is a 2'-(ara)-F sugar moiety.

Embodiment 44

The method of any of embodiments 1 to 20, wherein each modified nucleoside comprises a sugar surrogate.

Embodiment 45

The method of embodiment 44, wherein the sugar surrogate comprises an F-HNA sugar moiety.

Embodiment 46

The method of embodiment 44, wherein the sugar surrogate comprises an HNA sugar moiety.

Embodiment 47

The method of any of embodiments 1 to 47, wherein at least one modified nucleoside comprises a modified nucleobase.

Embodiment 48

The method of any of embodiments 1 to 47, wherein each modified nucleoside comprises a modified nucleobase.

Embodiment 49

The method of embodiments 1 to 20, wherein each modified nucleoside comprises a bicyclic sugar moiety

Embodiment 50

The method of any of embodiments 1 to 49, wherein the oligomeric compound comprises at least one modified internucleoside linkage.

Embodiment 51

The method of any of embodiments 1 to 50, wherein each internucleoside linkage in the oligomeric compound is a modified internucleoside linkage.

Embodiment 52

The method of any of embodiments 1 to 50, wherein the oligomeric compound comprises at least one phosphorothioate internucleoside linkage.

Embodiment 53

The method of any of embodiments 1 to 50, wherein each internucleoside linkage in the oligomeric compound is a phosphorothioate internucleoside linkage.

Embodiment 54

The method of any of embodiments 1 to 50, wherein the oligomeric compound comprises at least one phosphodiester internucleoside linkage.

Embodiment 55

The method of any of embodiments 1 to 50, wherein each internucleoside linkage in the oligomeric compound is a phosphodiester internucleoside linkage.

Embodiment 56

The method of any of embodiments 1 to 55, wherein the nucleic acid transcript encodes STAT3.

Embodiment 57

The method of any of embodiments 1 to 56, wherein the oligomeric compound has a nucleobase sequence selected from among SEQ ID NOs.: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 112, 113, 114, 115, 116, 117, 118, 120, 121, 122, 123, 124, 125, 126, or 127.

Embodiment 58

The method of any of embodiments 1 to 56, wherein the oligomeric compound has a nucleobase sequence selected from among SEQ ID NOs.:136, 146, 147, 148, 149, 159, 160, 161, 162, 163, 164, 165, 166, 167, 168, or 169.

Embodiment 59

The method of any of embodiments 1 to 58, wherein the oligomeric compound increases exclusion of exon 6 from STAT3 mRNA.

Embodiment 60

The method of any of embodiments 1 to 58, wherein the oligomeric compound increases exclusion of exon 5 from STAT3 mRNA.

Embodiment 61

The method of any of embodiments 1 to 58, wherein the oligomeric compound increases exclusion of two or more exons from STAT3 mRNA.

Embodiment 62

The method of any of embodiments 1 to 58, wherein the oligomeric compound increases exclusion of exon 5 and exon 6 from STAT3 mRNA.

Embodiment 63

The method of any of embodiments 1 to 62, wherein the oligomeric compound introduces a premature termination codon into STAT3 mRNA.

Embodiment 64

The method of any of embodiments 1 to 58, wherein the oligomeric compound increases exclusion of exon 17 from STAT3 mRNA.

Embodiment 65

The method of any of embodiments 1 to 58, wherein the oligomeric compound increases exclusion of exon 2 from SOD1 mRNA.

Embodiment 66

The method of any of embodiments 1 to 58, wherein the oligomeric compound increases exclusion of exon 3 from SOD1 mRNA.

Embodiment 67

The method of any of embodiments 1 to 58, wherein the oligomeric compound increases exclusion of two or more exons from SOD1 mRNA.

Embodiment 68

The method of any of embodiments 1 to 58 or 67, wherein the oligomeric compound increases exclusion of exon 2 and exon 3 from SOD1 mRNA.

Embodiment 69

The method of any of embodiments 1 to 58 or 65 to 68, wherein the oligomeric compound introduces a premature termination codon into SOD1 mRNA.

Embodiment 70

The method of any of embodiments 1 to 69, wherein the cell is in an animal.

Embodiment 71

The method of embodiment 70, wherein the animal is a mouse.

Embodiment 72

The method of embodiment 70, wherein the animal is a human.

Embodiment 73

The method of any of embodiments 1 to 69, wherein the cell is in vivo.

Embodiment 74

An oligomeric compound comprising a modified oligonucleotide, wherein the modified oligonucleotide consists of 10 to 30 linked nucleosides, wherein each nucleoside of the modified oligonucleotide comprises a modified nucleoside, and wherein each modified nucleoside comprises a 2'-MOE modified nucleobase.

Embodiment 75

An oligomeric compound comprising a modified oligonucleotide, wherein the modified oligonucleotide has an $A-B_2-A-B_2-A-B_2-A-B_2-A-B_2-A$ motif, wherein each A comprises a bicylic sugar moiety, and wherein each B is selected from a 2'-substituted sugar moiety and an unmodified 2'-deoxy sugar moiety.

Embodiment 76

An oligomeric compound comprising a modified oligonucleotide, wherein the modified oligonucleotide has an $A_2-B_2-A-B_2-A-B_2-A-B_2-A-B_2-A_2$ motif, wherein each A comprises a bicylic sugar moiety, and wherein each B is selected from a 2'-substituted sugar moiety and an unmodified 2'-deoxy sugar moiety.

Embodiment 77

The compound of embodiment 75 or 76, wherein each A is a cEt sugar moiety.

Embodiment 78

The compound of embodiment 75 or 76, wherein each A is an LNA sugar moiety.

Embodiment 79

The compound of embodiment 75 or 76, wherein each B is an unmodified 2'-deoxy sugar moiety.

Embodiment 80

The compound of embodiment 75 or 76, wherein each B is a 2'-MOE sugar moiety.

Embodiment 81

The compound of any of embodiments 74 to 80, wherein the nucleobase sequence of the oligomeric compound comprises a nucleobase sequence selected from the group consisting of SEQ ID NOs. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 112, 113, 114, 115, 116, 117, 118, 120, 121, 122, 123, 124, 125, 126, or 127.

Embodiment 82

The compound of any of embodiments 74 to 80, wherein the nucleobase sequence of the oligomeric compound consists of a nucleobase sequence selected from the group consisting of SEQ ID NOs. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 112, 113, 114, 115, 116, 117, 118, 120, 121, 122, 123, 124, 125, 126, or 127.

Embodiment 83

The compound of any of embodiments 74 to 80, wherein the nucleobase sequence of the oligomeric compound consists of a nucleobase sequence selected from the group consisting of SEQ ID NOs. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44.

Embodiment 84

The compound of any of embodiments 74 to 80, wherein the oligomeric compound has a nucleobase sequence selected from among SEQ ID NOs.:136, 146, 147, 148, 149, 159, 160, 161, 162, 163, 164, 165, 166, 167, 168, or 169.

Embodiment 85

The compound of any of embodiments 74 to 80, wherein the oligomeric compound has a nucleobase sequence selected from among SEQ ID NOs.:136, 146, 147, 148, 149, 159, 160, 161, 162, 163, 164, 165, 166, 167, 168, or 169.

Embodiment 86

The compound of any of embodiments 74 to 80, wherein the nucleobase sequence of the oligomeric compound consists of a nucleobase sequence of SEQ ID NO. 22.

Embodiment 87

The compound of any of embodiments 74 to 80, wherein the nucleobase sequence of the oligomeric compound consists of a nucleobase sequence of SEQ ID NO. 25.

Embodiment 88

The compound of any of embodiments 74 to 80, wherein the nucleobase sequence of the oligomeric compound consists of a nucleobase sequence selected from the group consisting of SEQ ID NOs: 112, 113, 114, 115, 116, 117, or 118.

Embodiment 89

The compound of any of embodiments 74 to 80, wherein the nucleobase sequence of the oligomeric compound consists of a nucleobase sequence selected from the group consisting of SEQ ID NOs. 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, or 105.

Embodiment 90

The compound of any of embodiments 74 to 80, wherein the nucleobase sequence of the oligomeric compound consists of a nucleobase sequence selected from the group consisting of SEQ ID NOs.: 120, 121, 122, 123, 124, 125, 126, or 127.

Embodiment 91

The compound of any of embodiments 74 to 80, wherein the nucleobase sequence of the oligomeric compound consists of a nucleobase sequence selected from the group consisting of SEQ ID NOs.: 91, 87, 95, 76, 89, 90, 96, 88, 77, 78, or 92.

Embodiment 92

The compound of any of embodiments 74 to 80, wherein the nucleobase sequence of the oligomeric compound consists of a nucleobase sequence of SEQ ID NO. 87.

Embodiment 93

The compound of any of embodiments 74 to 80, wherein the nucleobase sequence of the oligomeric compound consists of a nucleobase sequence of SEQ ID NO. 76.

Embodiment 94

A method of reducing the amount or activity of a target nucleic acid, comprising contacting a cell with the compound of any of embodiments 74 to 93.

Embodiment 95

The method of embodiment 94, wherein the target nucleic acid comprises pre-mRNA.

Embodiment 96

The method of embodiment 94, wherein the target nucleic acid comprises mRNA.

Embodiment 97

The method of any of embodiments 94 to 96, wherein the target nucleic acid encodes a protein selected from the group consisting of STAT3, SOD1, or HNRNPH1.

Embodiment 98

A method of increasing exon 5 exclusion in a target nucleic acid that encodes STAT3, comprising contacting a cell with the compound of any of embodiments 56 to 61.

Embodiment 99

A method of increasing exon 6 exclusion in a target nucleic acid that encodes STAT3, comprising contacting a cell with the compound of any of embodiments 74 to 93.

Embodiment 100

A method of increasing exon 17 exclusion in a target nucleic acid that encodes STAT3, comprising contacting a cell with the compound of any of embodiments 74 to 93.

Embodiment 101

A method of increasing exon 2 exclusion in a target nucleic acid that encodes SOD1, comprising contacting a cell with the compound of any of embodiments 74 to 93.

Embodiment 102

A method of increasing exon 3 exclusion in a target nucleic acid that encodes SOD1, comprising contacting a cell with the compound of any of embodiments 74 to 93.

Embodiment 103

A method of reducing STAT3 mRNA in a cell, comprising contacting a cell with the compound of any of embodiments 74 to 93.

Embodiment 104

A method of reducing SOD1 mRNA in a cell, comprising contacting a cell with the compound of any of embodiments 74 to 93.

Embodiment 105

A method of reducing HNRNPH1 mRNA in a cell, comprising contacting a cell with the compound of any of embodiments 74 to 93.

Embodiment 106

A method of reducing STAT3 target nucleic acid in a cell, comprising contacting a cell with the compound of any of embodiments 74 to 93.

Embodiment 107

A method of reducing SOD1 target nucleic acid in a cell, comprising contacting a cell with the compound of any of embodiments 74 to 93.

Embodiment 108

A method of reducing HNRNPH1 target nucleic acid in a cell, comprising contacting a cell with the compound of any of embodiments 98 to 107.

Embodiment 109

The method of any of embodiments 98 to 107, wherein the cell is in vivo.

Embodiment 110

The method of any of embodiments 98 to 107, wherein the cell is in an animal.

Embodiment 111

The method of embodiment 110, wherein the animal is a mouse.

Embodiment 112

The method of embodiment 110, wherein the animal is a human.

BRIEF DESCRIPTION OF THE FIGURES

FIG. 1 show a schematic of antisense induced exon 6 skipping of STAT3 leading to knockdown of STAT3 mRNA through nonsense mediated decay.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

I. Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

"Nucleoside" means a compound comprising a heterocyclic base moiety and a sugar moiety. Nucleosides include, but are not limited to, naturally occurring nucleosides, modified nucleosides, and nucleosides having mimetic bases and/or sugar groups. Nucleosides may be modified with any of a variety of substituents.

"Sugar moiety" means a natural or modified sugar or sugar surrogate.

"Natural sugar" means a ribofuranose moiety of DNA (2'-H) or RNA (2'-OH).

"Modified sugar" means a ribofuranose moiety comprising at least one substituent other than that of a natural sugar.

"Sugar surrogate" means a structure other than a ribofuranose ring which is capable of substituting for the sugar of a nucleoside. Examples of sugar surrogates include, but are not limited to, open ring systems, 6-membered rings, sugars in which the oxygen is replace with, for example, sulfur or nitrogen. For example, sugar surrogates include, but are not limited to morpholinos and 4'-thio-containing sugars.

"Nucleobase" means the heterocyclic base portion of a nucleoside. Nucleobases may be naturally occurring or may be modified. In certain embodiments, a nucleobase may comprise any atom or group of atoms capable of hydrogen bonding to a nucleobase of another nucleic acid.

"Nucleotide" means a nucleoside comprising a phosphate linking group. As used herein, nucleosides include nucleotides.

"Modified nucleoside" a nucleoside comprising at least one modification compared to naturally occurring RNA or DNA nucleosides. Such modification may be at the sugar moiety and/or at the nucleobase.

"Bicyclic nucleoside" or "BNA" means a nucleoside wherein the sugar moiety of the nucleoside comprises a bridge connecting two carbon atoms of the sugar ring, thereby forming a bicyclic sugar moiety.

"4'-2' bicyclic nucleoside" means a bicyclic nucleoside comprising a furanose ring comprising a bridge connecting two carbon atoms of the furanose ring connects the 2' carbon atom and the 4' carbon atom of the sugar ring.

"2'-modified" or "2'-substituted" means a nucleoside comprising a sugar comprising a substituent at the 2' position other than H or OH.

"2'-OMe" or "2'-OCH$_3$" or "2'-O-methyl" each means a nucleoside comprising a sugar comprising an —OCH$_3$ group at the 2' position of the sugar ring.

"MOE" or "2'-MOE" or "2'-OCH$_2$CH$_2$OCH$_3$" or "2'-O-methoxyethyl" each means a nucleoside comprising a sugar comprising a —OCH$_2$CH$_2$OCH$_3$ group at the 2' position of the sugar ring.

"Oligonucleotide" means a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

"Oligonucleoside" means an oligonucleotide in which none of the internucleoside linkages contains a phosphorus atom. As used herein, oligonucleotides include oligonucleosides.

"Modified oligonucleotide" means an oligonucleotide comprising at least one modified nucleoside and/or at least one modified internucleoside linkage.

"Internucleoside linkage" means a covalent linkage between adjacent nucleosides of an oligonucleotide.

"Naturally occurring internucleoside linkage" means a 3' to 5' phosphodiester linkage.

"Modified internucleoside linkage" means any internucleoside linkage other than a naturally occurring internucleoside linkage.

"Oligomeric compound" means a compound comprising an oligonucleotide. In certain embodiments, an oligomeric compound consists of an oligonucleotide. In certain embodiments, an oligomeric compound further comprises one or more conjugate and/or terminal groups.

"Antisense compound" means an oligomeric compound, at least a portion of which is at least partially complementary to a target nucleic acid to which it hybridizes, wherein such hybridization results at least one antisense activity.

"Antisense oligonucleotide" means an antisense compound wherein the oligomeric compound consists of an oligonucleotide.

"Antisense activity" refers to any detectable and/or measurable effect attributable to the hybridization of an antisense compound to its target nucleic acid. In certain embodiments, such antisense activity is an increase or decrease in an amount of a nucleic acid or protein. In certain embodiments, such antisense activity is a change in the ratio of splice variants of a nucleic acid or protein. In certain embodiments, such antisense activity is a phenotypic change in a cell and/or subject.

"Detecting" or "measuring" of antisense activity may be direct or indirect. For example, in certain embodiments, antisense activity is assessed by detecting and/or measuring the amount of target nucleic acid or protein or the relative amounts of splice variants of a target nucleic acid or protein. In certain embodiments, antisense activity is detected by observing a phenotypic change in a cell or animal. In connection with any activity, response, or effect, the terms "detecting" and "measuring," indicate that a test for detecting or measuring is performed. Such detection and/or measuring may include values of zero. Thus, if a test for detection or measuring results in a finding of no activity (activity of zero), the step of detecting or measuring the activity has nevertheless been performed.

"Target nucleic acid" refers to any nucleic acid molecule the expression, amount, or activity of which is capable of being modulated by an antisense compound.

"Target mRNA" means a pre-selected RNA molecule that encodes a protein.

"Target pre-mRNA" means a pre-selected RNA transcript that has not been fully processed into mRNA. Notably, pre-mRNA includes one or more intron.

"Target protein" means a protein encoded by a target nucleic acid.

"Modulation" means to a perturbation of function or activity. In certain embodiments, modulation means an increase in gene expression. In certain embodiments, modulation means a decrease in gene expression.

"Expression" means any functions and steps by which a gene's coded information is converted into structures present and operating in a cell.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that a first nucleic acid is capable of hybridizing to a second nucleic acid under stringent hybridization conditions. For example, an antisense compound is complementary to its target nucleic acid if it is capable of hybridizing to the target nucleic acid under stringent hybridization conditions.

"Fully complementary" means each nucleobase of a first nucleic acid is capable of pairing with a nucleobase at each corresponding contiguous position in a second nucleic acid.

"Percent complementarity" of an antisense compound means the percentage of nucleobases of the antisense compound that are complementary to an equal-length portion of a target nucleic acid. Percent complementarity is calculated by dividing the number of nucleobases of the antisense oligonucleotide that are complementary to nucleobases at corresponding contiguous positions in the target nucleic acid by the total length of the antisense compound.

"Percent identity" means the number of nucleobases in first nucleic acid that are identical to nucleobases at corresponding positions in a second nucleic acid, divided by the total number of nucleobases in the first nucleic acid.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Identical nucleobase sequence" means having the same nucleobase sequence, independent of any chemical modifications to the nucleosides.

"Different modifications" or "differently modified" refer to nucleosides or internucleoside linkages that have different nucleoside modifications or internucleoside linkages than one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified, unless otherwise indicated. For example, a nucleoside comprising a 2'-OMe modified sugar and an adenine nucleobase and a nucleoside comprising a 2'-OMe modified sugar and a thymine nucleobase are not differently modified.

"The same modifications" refer to nucleosides and internucleoside linkages (including unmodified nucleosides and internucleoside linkages) that are the same as one another. Thus, for example, two unmodified DNA nucleoside have "the same modification," even though the DNA nucleoside is unmodified.

"Type of modification" or nucleoside of a "type" means the modification of a nucleoside and includes modified and unmodified nucleosides. Accordingly, unless otherwise indicated, a "nucleoside having a modification of a first type" may be an unmodified nucleoside.

"Separate regions" of an oligonucleotide means a portion of an oligonucleotide wherein the nucleosides and internucleoside linkages within the region all comprise the same modifications; and the nucleosides and/or the internucleoside linkages of any neighboring portions include at least one different modification.

"Motif" means a pattern of modified and/or unmodified nucleobases, sugars, and/or internucleoside linkages in an oligonucleotide.

"Fully modified oligonucleotide" means each nucleobase, each sugar, and/or each internucleoside linkage is modified.

"Uniformly modified oligonucleotide" means each nucleobase, each sugar, and/or each internucleoside linkage has the same modification throughout the modified oligonucleotide.

"Subject" means a human or non-human animal selected for treatment or therapy.

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Systemic administration" means administration to an area other than the intended locus of activity. Examples or systemic administration are subcutaneous administration and intravenous administration, and intraperitoneal administration.

"Subcutaneous administration" means administration just below the skin.

"Intravenous administration" means administration into a vein.

"Cerebrospinal fluid" or "CSF" means the fluid filling the space around the brain and spinal cord.

"Administration into the cerebrospinal fluid" means any administration that delivers a substance directly into the CSF.

"Intracerebroventricular" or "ICV" mean administration into the ventricular system of the brain.

"Intrathecal" or "IT" means administration into the CSF under the arachnoid membrane which covers the brain and spinal cord. IT injection is performed through the theca of the spinal cord into the subarachnoid space, where a pharmaceutical agent is injected into the sheath surrounding the spinal cord.

"Induction phase" means a dosing phase during which administration is initiated and steady state concentrations of active pharmaceutical agent are achieved in a target tissue. For example, an induction phase is a dosing phase during which steady state concentrations of antisense oligonucleotide are achieved in liver.

"Maintenance phase" means a dosing phase after target tissue steady state concentrations of drug have been achieved.

"Duration" means the period of time during which an activity or event continues. For example, the duration of an induction phase is the period of time during which induction doses are administered.

"Maintenance dose" means a dose administered at a single administration during the maintenance phase. As used herein, "induction dose" means a dose administered at a single administration during the induction phase.

"Co-administration" means administration of two or more pharmaceutical agents to a subject. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Therapy" means a disease treatment method. In certain embodiments, therapy includes, but is not limited to surgical therapies, chemical therapies, and physical interventions, such as assisted respiration, feeding tubes, and physical therapy for the purpose of increasing strength.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition.

"Slow the progression of" means that the severity of at least one symptom associated with a disease or condition worsens less quickly.

"Dose" means a specified quantity of a pharmaceutical agent provided in a single administration or over a specified amount of time. In certain embodiments, a dose may be administered in two or more boluses, tablets, or injections. For example, in certain embodiments, where subcutaneous or inrathecal or ICV administration is desired, the desired dose requires a volume not easily accommodated by a single injection. In such embodiments, two or more injections may be used to achieve the desired dose. In the setting of continuous infusion, dose may be expressed as the quantity of a pharmaceutical agent delivered per unit of time.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" means an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a modified oligonucleotide and a sterile aqueous solution.

"Acceptable safety profile" means a pattern of side effects that is within clinically acceptable limits.

"Side effect" means a physiological response attributable to a treatment other than desired effects.

"Nonsense mediated decay" means any number of cellular mechanisms independent of RNase H or RISC that degrade mRNA or pre-mRNA. In certain embodiments, nonsense mediated decay eliminates and/or degrades mRNA transcripts that contain premature stop codons. In certain embodiments, nonsense mediated decay eliminates and/or degrades any form of aberrant mRNA and/or pre-mRNA transcripts.

1. Certain Modified Oligonucleotides

In certain embodiments, the present invention provides methods and compositions involving antisense oligonucleotides comprising one or more modification compared to oligonucleotides of naturally occurring oligomers, such as DNA or RNA. Such modified antisense oligonucleotides may possess one or more desirable properties. Certain such modifications alter the antisense activity of the antisense oligonucleotide, for example by increasing affinity of the antisense oligonucleotide for its target nucleic acid, increasing its resistance to one or more nucleases, and/or altering the pharmacokinetics or tissue distribution of the oligonucleotide. In certain embodiments, such modified antisense oligonucleotides comprise one or more modified nucleosides and/or one or more modified nucleoside linkages and/or one or more conjugate groups.

a. Certain Modified Nucleosides

In certain embodiments, antisense oligonucleotides comprise one or more modified nucleosides. Such modified nucleosides may include a modified sugar and/or a modified nucleobase. In certain embodiments, incorporation of such modified nucleosides in an oligonucleotide results in increased affinity for a target nucleic acid and/or increased stability, including but not limited to, increased resistance to nuclease degradation, and or improved toxicity and/or uptake properties of the modified oligonucleotide.

i. Certain Nucleobases

The naturally occurring base portion of nucleosides are heterocyclic base, typically purines and pyrimidines. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to incorporation into the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

ii. Certain Modified Sugars and Sugar Surrogates

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N (R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$) (R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$ SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH (CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., J. Org. Chem., 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$alkenyl, substituted C$_2$-C$_{12}$alkenyl, C$_2$-C$_{12}$alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—

H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

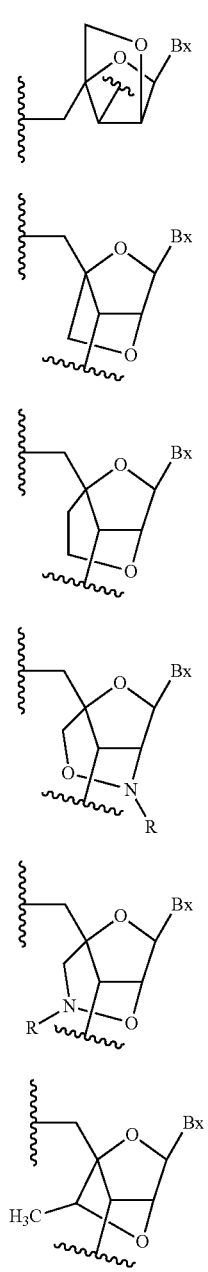

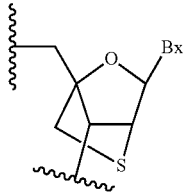

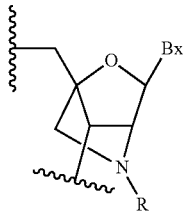

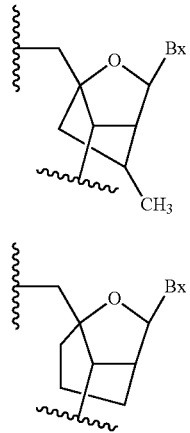

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

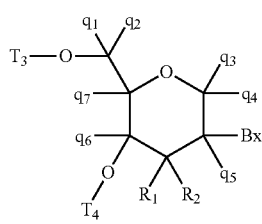

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Antisense oligonucleotides of the present invention can optionally contain one or more nucleosides wherein the sugar moiety is modified, compared to a natural sugar. Oligonucleotides comprising such sugar modified nucleosides may have enhanced nuclease stability, increased binding affinity or some other beneficial biological property. Such modifications include without limitation, addition of substituent groups, bridging of non-geminal ring atoms to form a bicyclic nucleic acid (BNA), replacement of the ribosyl ring oxygen atom with S, N(R), or $C(R_1)(R)_2$ (R=H, $C_1$-$C_{12}$ alkyl or a protecting group) and combinations of these such as for example a 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$ and 2'-O(CH$_2$)$_2$OCH$_3$ substituent groups. The substituent at the 2' position can also be selected from allyl, amino, azido, thio, O-allyl, O—$C_1$-$C_{10}$ alkyl, OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), where each R$_m$ and R$_n$ is, independently, H or substituted or unsubstituted $C_1$-$C_{10}$ alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-β-D-(CH$_2$)—O-2' (β-D-LNA); 4'-(CH$_2$)—S-2; 4'-α-L-(CH$_2$)—O-2' (α-L-LNA); 4'-(CH$_2$)$_2$—O-2' (ENA); 4'-C(CH$_3$)$_2$—O-2' (see PCT/US2008/068922); 4'-CH(CH$_3$)—O-2' and 4'-C—H(CH$_2$OCH$_3$)—O-2' (see U.S. Pat.

No. 7,399,845, issued on Jul. 15, 2008); 4'-CH$_2$—N(OCH$_3$)-2' (see PCT/US2008/064591); 4'-CH$_2$—O—N(CH$_3$)-2' (see published U.S. Patent Application US2004-0171570, published Sep. 2, 2004); 4'-CH$_2$—N(R)—O-2' (see U.S. Pat. No. 7,427,672, issued on Sep. 23, 2008); 4'-CH$_2$—C(CH$_3$)-2' and 4'-CH$_2$—C(=CH$_2$)-2' (see PCT/US2008/066154); and wherein R is, independently, H, C$_1$-C$_{12}$ alkyl, or a protecting group.

In certain embodiments, the present invention provides modified nucleosides comprising modified sugar moieties that are not bicyclic sugar moieties. Certain such modified nucleosides are known. In certain embodiments, the sugar ring of a nucleoside may be modified at any position. Examples of sugar modifications useful in this invention include, but are not limited to compounds comprising a sugar substituent group selected from: OH, F, O-alkyl, S-alkyl, N-alkyl, or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. In certain such embodiments, such substituents are at the 2' position of the sugar.

In certain embodiments, modified nucleosides comprise a substituent at the 2' position of the sugar. In certain embodiments, such substituents are selected from among: a halide (including, but not limited to F), allyl, amino, azido, thio, O-allyl, O—C$_1$-C$_{10}$ alkyl, —OCF$_3$, O—(CH$_2$)$_2$—O—CH$_3$, 2'-O(CH$_2$)$_2$SCH$_3$, O—(CH$_2$)$_2$—O—N(R$_m$)(R$_n$), or O—CH2-C(=O)—N(R$_m$)(R$_n$), where each R$_m$ and R$_n$ is, independently, H or substituted or unsubstituted C$_1$-C$_{10}$ alkyl.

In certain embodiments, modified nucleosides suitable for use in the present invention are: 2-methoxyethoxy, 2'-O-methyl (2'-O—CH$_3$), 2'-fluoro (2'-F).

In certain embodiments, modified nucleosides having a substituent group at the 2'-position selected from: O[(CH$_2$)$_n$O]$_m$CH$_3$, O(CH$_2$)$_n$—NH$_2$, O(CH$_2$)$_n$—CH$_3$, O(CH$_2$)$_n$—ONH$_2$, OCH$_2$C(=O)N(H)CH$_3$, and O(CH$_2$)$_n$—ON[(CH$_2$)$_n$—CH$_3$]$_2$, where n and m are from 1 to about 10. Other 2'-sugar substituent groups include: C$_1$ to C$_{10}$ alkyl, substituted alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, amino alkylamino, polyalkylamino, substituted silyl, an RNA cleaving group, a reporter group, an intercalator, a group for improving pharmacokinetic properties, or a group for improving the pharmacodynamic properties of an oligomeric compound, and other substituents having similar properties.

In certain embodiments, modified nucleosides comprise a 2'-MOE side chain (Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

In certain embodiments, 2'-sugar substituent groups are in either the arabino (up) position or ribo (down) position. In certain such embodiments, a 2'-arabino modification is 2'-F arabino (FANA). Similar modifications can also be made at other positions on the sugar, particularly the 3' position of the sugar on a 3' terminal nucleoside or in 2'-5' linked oligonucleotides and the 5' position of 5' terminal nucleotide.

In certain embodiments, nucleosides suitable for use in the present invention have sugar surrogates such as cyclobutyl in place of the ribofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

In certain embodiments, the present invention provides nucleosides comprising a modification at the 2'-position of the sugar. In certain embodiments, the invention provides nucleosides comprising a modification at the 5'-position of the sugar. In certain embodiments, the invention provides nucleosides comprising modifications at the 2'-position and the 5'-position of the sugar. In certain embodiments, modified nucleosides may be useful for incorporation into oligonucleotides. In certain embodiment, modified nucleosides are incorporated into oligonucleosides at the 5'-end of the oligonucleotide.

b. Certain Internucleoside Linkages

Antisense oligonucleotides of the present invention can optionally contain one or more modified internucleoside linkages. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH2-N(CH3)-O—CH2-), thiodiester (—O—C(O)—S—), thionocarbamate (—O—C(O)(NH)—S—); siloxane (—O—Si(H)2-O—); and N,N'-dimethylhydrazine (—CH2-N(CH3)-N(CH3)-). Oligonucleotides having non-phosphorus linking groups are referred to as oligonucleosides. Modified linkages, compared to natural phosphodiester linkages, can be used to alter, typically increase, nuclease resistance of the oligonucleotides. In certain embodiments, linkages having a chiral atom can be prepared as racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

The antisense oligonucleotides described herein contain one or more asymmetric centers and thus give rise to enantiomers, diastereomers, and other stereoisomeric configurations that may be defined, in terms of absolute stereochemistry, as (R) or (S), such as for sugar anomers, or as (D) or (L) such as for amino acids et al. Included in the antisense compounds provided herein are all such possible isomers, as well as their racemic and optically pure forms.

In certain embodiments, antisense oligonucleotides have at least one modified internucleoside linkage. In certain embodiments, antisense oligonucleotides have at least 2 modified internucleoside linkages. In certain embodiments, antisense oligonucleotides have at least 3 modified internucleoside linkages. In certain embodiments, antisense oligonucleotides have at least 10 modified internucleoside linkages. In certain embodiments, each internucleoside linkage of an antisense oligonucleotide is a modified internucleoside linkage. In certain embodiments, such modified internucleoside linkages are phosphorothioate linkages.

c. Lengths

In certain embodiments, the present invention provides antisense oligonucleotides of any of a variety of ranges of lengths. In certain embodiments, the invention provides antisense compounds or antisense oligonucleotides comprising or consisting of X-Y linked nucleosides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides antisense compounds or antisense oligonucleotides comprising or consisting of: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked nucleosides.

In certain embodiments, antisense compounds or antisense oligonucleotides of the present invention are 15 nucleosides in length. In certain embodiments, antisense compounds or antisense oligonucleotides of the present invention are 16 nucleosides in length. In certain embodiments, antisense compounds or antisense oligonucleotides of the present invention are 17 nucleosides in length. In certain embodiments, antisense compounds or antisense oligonucleotides of the present invention are 18 nucleosides in length. In certain embodiments, antisense compounds or antisense oligonucleotides of the present invention are 19 nucleosides in length. In certain embodiments, antisense compounds or antisense oligonucleotides of the present invention are 20 nucleosides in length.

d. Certain Oligonucleotide Motifs

In certain embodiments, antisense oligonucleotides have chemically modified subunits arranged in specific orientations along their length. In certain embodiments, antisense oligonucleotides of the invention are fully modified. In certain embodiments, antisense oligonucleotides of the invention are uniformly modified. In certain embodiments, antisense oligonucleotides of the invention are uniformly modified and each nucleoside comprises a 2'-MOE sugar moiety. In certain embodiments, antisense oligonucleotides of the invention are uniformly modified and each nucleoside comprises a 2'-OMe sugar moiety. In certain embodiments, antisense oligonucleotides of the invention are uniformly modified and each nucleoside comprises a morpholino sugar moiety.

In certain embodiments, oligonucleotides of the invention comprise an alternating motif. In certain such embodiments, the alternating modification types are selected from among 2'-MOE, 2'-F, a bicyclic sugar-modified nucleoside, and DNA (unmodified 2'-deoxy). In certain such embodiments, each alternating region comprises a single nucleoside.

In certain embodiments, oligonucleotides of the invention comprise one or more block of nucleosides of a first type and one or more block of nucleosides of a second type.

In certain embodiments, one or more alternating regions in an alternating motif include more than a single nucleoside of a type. For example, oligomeric compounds of the present invention may include one or more regions of any of the following nucleoside motifs:

$Nu_1\ Nu_1\ Nu_2\ Nu_2\ Nu_1\ Nu_1$;

$Nu_1\ Nu_2\ Nu_2\ Nu_1\ Nu_2\ Nu_2$;

$Nu_1\ Nu_1\ Nu_2\ Nu_1\ Nu_1\ Nu_2$;

$Nu_1\ Nu_2\ Nu_2\ Nu_1\ Nu_2\ Nu_1\ Nu_1\ Nu_2\ Nu_2$;

$Nu_1\ Nu_2\ Nu_1\ Nu_2\ Nu_1\ Nu_1$;

$Nu_1\ Nu_1\ Nu_2\ Nu_1\ Nu_2\ Nu_1\ Nu_2$;

$Nu_1\ Nu_2\ Nu_1\ Nu_2\ Nu_1\ Nu_1$;

$Nu_1\ Nu_2\ Nu_2\ Nu_1\ Nu_1\ Nu_2\ Nu_2\ Nu_1\ Nu_2\ Nu_2\ Nu_1\ Nu_1$;

$Nu_2\ Nu_1\ Nu_2\ Nu_2\ Nu_1\ Nu_1\ Nu_2\ Nu_2\ Nu_1\ Nu_2\ Nu_1 Nu_2\ Nu_1\ Nu_1$; or $Nu_1\ Nu_2 Nu_1\ Nu_2\ Nu_2\ Nu_1\ Nu_1\ Nu_2\ Nu_2\ Nu_1\ Nu_2\ Nu_1\ Nu_2\ Nu_1\ Nu_1$;

wherein $Nu_1$ is a nucleoside of a first type and $Nu_2$ is a nucleoside of a second type. In certain embodiments, one of $Nu_1$ and $Nu_2$ is a 2'-MOE nucleoside and the other of $Nu_1$ and $Nu_2$ is a selected from: a 2'-OMe modified nucleoside, BNA, and an unmodified DNA or RNA nucleoside.

2. Oligomeric Compounds

In certain embodiments, the present invention provides oligomeric compounds. In certain embodiments, oligomeric compounds are comprised only of an oligonucleotide. In certain embodiments, an oligomeric compound comprises an oligonucleotide and one or more conjugate and/or terminal group. Such conjugate and/or terminal groups may be added to oligonucleotides having any of the chemical motifs discussed above. Thus, for example, an oligomeric compound comprising an oligonucleotide having region of alternating nucleosides may comprise a terminal group.

a. Certain Conjugate Groups

In certain embodiments, oligonucleotides of the present invention are modified by attachment of one or more conjugate groups. In general, conjugate groups modify one or more properties of the attached oligomeric compound including but not limited to, pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Conjugate groups may be attached to either or both ends of an oligonucleotide (terminal conjugate groups) and/or at any internal position.

b. Terminal Groups

In certain embodiments, oligomeric compounds comprise terminal groups at one or both ends. In certain embodiments, a terminal group may comprise any of the conjugate groups discussed above. In certain embodiments, terminal groups may comprise additional nucleosides and/or inverted abasic nucleosides. In certain embodiments, a terminal group is a stabilizing group.

In certain embodiments, oligomeric compounds comprise one or more terminal stabilizing group that enhances properties such as for example nuclease stability. Included in stabilizing groups are cap structures. The terms "cap structure" or "terminal cap moiety," as used herein, refer to chemical modifications, which can be attached to one or both of the termini of an oligomeric compound. Certain such terminal modifications protect the oligomeric compounds having terminal nucleic acid moieties from exonuclease degradation, and can help in delivery and/or localization within a cell. The cap can be present at the 5'-terminus (5'-cap) or at the 3'-terminus (3'-cap) or can be present on both termini. (for more details see Wincott et al., International PCT publication No. WO 97/26270; Beaucage and Tyer, 1993, Tetrahedron 49, 1925; U.S. Patent Application Publication No. US 2005/0020525; and WO 03/004602.

In certain embodiments, one or more additional nucleosides is added to one or both terminal ends of an oligonucleotide of an oligomeric compound. Such additional terminal nucleosides are referred to herein as terminal-group nucleosides. In a double-stranded compound, such terminal-group nucleosides are terminal (3' and/or 5') overhangs. In the setting of double-stranded antisense compounds, such terminal-group nucleosides may or may not be complementary to a target nucleic acid. In certain embodiments, the terminal group is a non-nucleoside terminal group. Such non-terminal groups may be any terminal group other than a nucleoside.

3. Antisense

In certain embodiments, oligomeric compounds of the present invention are antisense compounds. Accordingly, in such embodiments, oligomeric compounds hybridize with a target nucleic acid, resulting in an antisense activity.

a. Hybridization

In certain embodiments, the invention provides antisense compounds that specifically hybridize to a target nucleic acid when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

Thus, "stringent hybridization conditions" or "stringent conditions" means conditions under which an antisense compounds hybridize to a target sequence, but to a minimal number of other sequences. Stringent conditions are sequence-dependent and will be different in different circumstances, and "stringent conditions" under which antisense oligonucleotides hybridize to a target sequence are determined by the nature and composition of the antisense oligonucleotides and the assays in which they are being investigated.

It is understood in the art that incorporation of nucleotide affinity modifications may allow for a greater number of mismatches compared to an unmodified compound. Similarly, certain nucleobase sequences may be more tolerant to mismatches than other nucleobase sequences. One of ordinary skill in the art is capable of determining an appropriate number of mismatches between oligonucleotides, or between an antisense oligonucleotide and a target nucleic acid, such as by determining melting temperature (Tm). Tm or ΔTm can be calculated by techniques that are familiar to one of ordinary skill in the art. For example, techniques described in Freier et al. (Nucleic Acids Research, 1997, 25, 22: 4429-4443) allow one of ordinary skill in the art to evaluate nucleotide modifications for their ability to increase the melting temperature of an RNA:DNA duplex.

b. Pre-mRNA Processing

In certain embodiments, antisense compounds provided herein are complementary to a pre-mRNA. In certain embodiments, such antisense compounds alter splicing of the pre-mRNA. In certain embodiments, such antisense compounds promote the inclusion of one or more exons into an mRNA transcript. In certain embodiments, such antisense compounds promote the exclusion of one or more exons into an mRNA transcript. In certain such embodiments, the ratio of one variant of a mature mRNA corresponding to a target pre-mRNA to another variant of that mature mRNA is altered. In certain such embodiments, the ratio of one variant of a protein expressed from the target pre-mRNA to another variant of the protein is altered. Certain oligomeric compounds and nucleobase sequences that may be used to alter splicing of a pre-mRNA may be found for example in U.S. Pat. Nos. 6,210,892; 5,627,274; 5,665,593; 5,916,808; 5,976,879; US2006/0172962; US2007/002390; US2005/0074801; US2007/0105807; US2005/0054836; WO 2007/090073; WO2007/047913, Hua et al., PLoS Biol 5(4):e73; Vickers et al., J. Immunol. 2006 Mar. 15; 176(6):3652-61; and Hua et al., American J. of Human Genetics (April 2008) 82, 1-15, each of which is hereby incorporated by reference in its entirety for any purpose. In certain embodiments antisense sequences that alter splicing are modified according to motifs of the present disclosure.

Antisense is an effective means for modulating the expression of one or more specific gene products and is uniquely useful in a number of therapeutic, diagnostic, and research applications. Provided herein are antisense compounds useful for modulating gene expression via antisense mechanisms of action, including antisense mechanisms based on target occupancy. In one aspect, the antisense compounds provided herein modulate splicing of a target gene. Such modulation includes promoting or inhibiting exon inclusion. Further provided herein are antisense compounds targeted to cis splicing regulatory elements present in pre-mRNA molecules, including exonic splicing enhancers, exonic splicing silencers, intronic splicing enhancers and intronic splicing silencers. Disruption of cis splicing regulatory elements is thought to alter splice site selection, which may lead to an alteration in the composition of splice products.

Processing of eukaryotic pre-mRNAs is a complex process that requires a multitude of signals and protein factors to achieve appropriate mRNA splicing. Exon definition by the spliceosome requires more than the canonical splicing signals which define intron-exon boundaries. One such additional signal is provided by cis-acting regulatory enhancer and silencer sequences. Exonic splicing enhancers (ESE), exonic splicing silencers (ESS), intronic splicing enhancers (ISE) and intron splicing silencers (ISS) have been identified which either repress or enhance usage of splice donor sites or splice acceptor sites, depending on their site and mode of action (Yeo et al. 2004, *Proc. Natl. Acad. Sci. U.S.A.* 101(44):15700-15705). Binding of specific proteins (trans factors) to these regulatory sequences directs the splicing process, either promoting or inhibiting usage of particular splice sites and thus modulating the ratio of splicing products (Scamborova et al. 2004, *Mol. Cell. Biol.* 24(5):1855-1869; Hovhannisyan and Carstens, 2005, *Mol. Cell. Biol.* 25(1):250-263; Minovitsky et al. 2005, *Nucleic Acids Res.* 33(2):714-724).

4. Pharmaceutical Compositions

In certain embodiments, the present invention provides pharmaceutical compositions comprising one or more antisense compound. In certain embodiments, such pharmaceutical composition comprises a sterile saline solution and one or more antisense compound. In certain embodiments, such pharmaceutical composition consists of a sterile saline solution and one or more antisense compound.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments antisense compounds, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in certain embodiments, employed in the methods described herein is a pharmaceutical composition comprising an antisense compound and a pharmaceutically acceptable diluent. In certain embodiments, the pharmaceutically acceptable diluent is PBS. In certain embodiments, the pharmaceutically acceptable diluent is artificial CSF.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid-based vectors have been used in nucleic acid therapies in a variety of methods. For example, in one method, the nucleic acid is introduced into preformed liposomes or lipoplexes made of mixtures of cationic lipids and neutral lipids. In another method, DNA complexes with mono- or poly-cationic lipids are formed without the presence of a neutral lipid.

Certain preparations are described in Akinc et al., *Nature Biotechnology* 26, 561-569 (1 May 2008), which is herein incorporated by reference in its entirety.

5. Certain Antisense Mechanisms a. Nonsense Mediated Decay

Nonsense mediated decay is a type of surveillance pathway that serves to reduce errors in aberrant gene expression through the elimination and/or degradation of aberrant mRNA transcripts. In certain embodiments, the mechanism of nonsense mediated decay selectively degrades mRNAs that result from errors in pre-mRNA processing. For example, many pre-mRNA transcripts contain a number of exons and introns that may be alternatively spliced to produce any number of mRNA transcripts containing various combinations of exons. The mRNA transcripts are then translated into any number of protein isoforms. In certain embodiments, pre-mRNA is processed in such a way to include one or more exons, the inclusion of which produces an mRNA that encodes or would encode a non-functional protein or a mis-folded protein. In certain embodiments, pre-mRNA is processed in such a way to include one or more exons, the inclusion of which produces an mRNA that contains a premature termination codon. In certain such embodiments, the nonsense mediated decay mechanism recognizes the mRNA transcript containing the extra exon and degrades the mRNA transcript prior to translation. In certain such embodiments, the nonsense mediated decay mechanism recognizes the mRNA transcript containing the premature termination codon and degrades the mRNA transcript prior to translation.

In certain embodiments, pre-mRNA is processed in such a way to exclude one or more exons, the exclusion of which produces an mRNA that encodes a non-functional protein. In certain embodiments, pre-mRNA is processed in such a way to exclude one or more exons, the exclusion of which produces an mRNA that contains a premature termination codon. In certain such embodiments, the nonsense mediated decay mechanism recognizes the mRNA transcript missing the exon and degrades the mRNA transcript prior to translation. In certain such embodiments, the nonsense mediated decay mechanism recognizes the mRNA transcript missing the exon and containing the premature termination codon and degrades the mRNA transcript prior to translation.

Antisense technology is an effective means for modulating the expression of one or more specific gene products, including alternative splice products, and is uniquely useful in a number of therapeutic, diagnostic, and research applications. In certain embodiments, the fully modified oligomeric compounds described herein modulate splicing of one or more target nucleic acids and such modulation causes the degradation and/or reduction of the target nucleic acid through nonsense mediated decay. In certain embodiments, the uniformly modified oligomeric compounds described herein modulate splicing of one or more target nucleic acids and such modulation causes the degradation and/or reduction of the target nucleic acid through nonsense mediated decay. In certain embodiments, uniformly modified oligomeric compounds described herein are used to promote splicing of a target pre-mRNA to include an exon and promote reduction of the resulting mRNA transcript through nonsense mediated decay.

In certain embodiments, an oligomeric compound complementary to a target nucleic acid alters the pre-mRNA processing in such a way as to produce an mRNA that is recognized by the nonsense mediated decay pathway. In certain embodiments, an oligomeric compound complementary to a target nucleic acid may increase inclusion of an exon, the inclusion of which causes the nonsense mediated decay pathway to recognize and degrade the exon containing mRNA. In certain embodiments, an oligomeric compound complementary to a target nucleic acid may increase inclusion of an exon and thereby introduce a premature termination codon in an mRNA transcript. In certain such embodiments, the mRNA containing the premature termination codon causes the nonsense mediated decay pathway to recognize and degrade the mRNA containing the premature termination codon.

In certain embodiments, an oligomeric compound complementary to a target nucleic acid may increase exclusion of an exon, the exclusion of which causes the nonsense mediated decay pathway to recognize and degrade the mRNA without the exon. In certain embodiments, an oligomeric compound complementary to a target nucleic acid may increase exclusion of an exon and thereby introduce a premature termination codon in an mRNA transcript. In certain such embodiments, the mRNA missing the exon and containing the premature termination codon causes the nonsense mediated decay pathway to recognize and degrade the mRNA containing the premature termination codon.

In certain embodiments, an oligomeric compound complementary to a target nucleic acid alters the pre-mRNA processing in such a way as to produce an mRNA that encodes a non-functional protein. In certain embodiments the non-functional protein is degraded by the proteasome. In certain embodiments the non-functional protein has little or no cellular activity. In certain embodiments, an oligomeric compound complementary to a target nucleic acid alters the pre-mRNA processing in such a way as to produce an mRNA that encodes a protein product having reduced function. In certain embodiments the reduced function protein is degraded by the proteasome. In certain embodiments the reduced function protein has little or no cellular activity.

In certain embodiments modulation of the amount or activity of a target nucleic acid through a nonsense mediated decay pathway is preferred over modulation of the amount or activity of a target nucleic acid through another mechanism. For example, in certain embodiments, modulation of the amount or activity of a target nucleic acid through nonsense mediated decay is preferred over modulation of the amount or activity of a target nucleic acid through the RISC pathway. For example, in certain embodiments, modulation of the amount or activity of a target nucleic acid through nonsense mediated decay is preferred over modulation of the amount or activity of a target nucleic acid through RNase H.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited herein is hereby incorporated by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Effects of Uniform 2'-MOE Modified Oligonucleotides on Human STAT3

A series of modified oligonucleotides were designed to target human STAT3 via a nonsense mediated decay mechanism and were screened for their effects in reducing STAT3 expression in vitro. The 5-10-5 MOE gapmer, ISIS 455291 was included in the study as a positive control for STAT3 knockdown. This gapmer inhibits STAT3 RNA expression via an RNase H-dependent mechanism.

The modified oligonucleotides are 18 nucleosides in length, wherein each nucleoside has a 2'-MOE modification and is denoted as subscript "e". Subscript "d" indicates β-D-2'-deoxyribonucleosides. Each internucleoside linkage throughout the modified oligonucleotide are phosphorothioate internucleoside linkages (P=S) and is denoted as subscript "s". All cytosine residues throughout the modified oligonucleotides are 5-methylcytosines and are denoted as superscripts "m".

HeLa cells were transfected using 3 µg/mL Cytofectin with 50 nM concentration of modified oligonucleotide. After a treatment period of approximately 24 hours, RNA was isolated from the cells and the RNA levels of STAT3 were measured by quantitative real-time PCR. Human primer probe set RTS199 was used to measure RNA levels. STAT3 levels were normalized to total RNA content, as measured by RIBOGREEN®. Results are presented as percent of STAT3 RNA expression, relative to untreated control levels and is denoted as "% UTC."

Human primer probe set RTS199 (forward sequence 5'-ACATGCCACTTTGGTGTTTCATAA-3', designated herein as SEQ ID NO: 1; reverse sequence 5'-TCTTCGTA-GATTGTGCTGATAGAGAAC-3', designated herein as SEQ ID NO: 2; probe sequence 5'-CAGTATAGCCGCTTC-CTGCAAGAGTCGAA-3', designated herein as SEQ ID NO: 3).

TABLE 1

Effects of uniform 2'-MOE modified oligonucleotides on human STAT3

| ISIS No. | Sequence (5' to 3') | % UTC | SEQ ID No. |
|---|---|---|---|
| 455291 | $^mC_{es}A_{es}G_{es}{}^mC_{es}A_{es}G_{ds}A_{ds}T_{ds}{}^mC_{ds}A_{ds}A_{ds}G_{ds}T_{ds}{}^mC_{ds}{}^mC_{ds}A_{es}G_{es}G_{es}G_{es}A_e$ | 12 | 4 |
| 580057 | $^mC_{es}T_{es}G_{es}T_{es}T_{es}T_{es}A_{es}A_{es}A_{es}A_{es}T_{es}A_{es}A_{es}G_{es}{}^mC_{es}A_{es}A_{es}A_e$ | 48 | 5 |
| 580058 | $A_{es}T_{es}{}^mC_{es}{}^mC_{es}T_{es}G_{es}T_{es}T_{es}T_{es}A_{es}A_{es}A_{es}T_{es}A_{es}A_{es}G_{es}{}^mC_e$ | 47 | 6 |
| 580059 | $T_{es}A_{es}G_{es}A_{es}T_{es}{}^mC_{es}{}^mC_{es}T_{es}G_{es}T_{es}T_{es}T_{es}A_{es}A_{es}A_{es}A_{es}T_{es}A_e$ | 30 | 7 |
| 580060 | $T_{es}T_{es}{}^mC_{es}T_{es}A_{es}G_{es}A_{es}T_{es}{}^mC_{es}{}^mC_{es}T_{es}G_{es}T_{es}T_{es}T_{es}A_{es}A_{es}A_e$ | 33 | 8 |
| 580061 | $^mC_{es}T_{es}G_{es}T_{es}T_{es}{}^mC_{es}T_{es}A_{es}G_{es}A_{es}T_{es}{}^mC_{es}{}^mC_{es}T_{es}G_{es}T_{es}T_{es}T_e$ | 12 | 9 |
| 580062 | $T_{es}T_{es}T_{es}{}^mC_{es}T_{es}G_{es}T_{es}T_{es}{}^mC_{es}T_{es}A_{es}G_{es}A_{es}T_{es}{}^mC_{es}{}^mC_{es}T_{es}G_e$ | 22 | 10 |
| 566296 | $^mC_{es}A_{es}T_{es}T_{es}T_{es}T_{es}{}^mC_{es}T_{es}G_{es}T_{es}T_{es}{}^mC_{es}T_{es}A_{es}G_{es}A_{es}T_{es}{}^mC_e$ | 25 | 11 |
| 580063 | $T_{es}T_{es}T_{es}{}^mC_{es}A_{es}T_{es}T_{es}T_{es}T_{es}{}^mC_{es}T_{es}G_{es}T_{es}T_{es}{}^mC_{es}T_{es}A_{es}G_e$ | 25 | 12 |
| 580064 | $^mC_{es}A_{es}{}^mC_{es}T_{es}T_{es}T_{es}{}^mC_{es}A_{es}T_{es}T_{es}T_{es}T_{es}{}^mC_{es}T_{es}G_{es}T_{es}T_{es}{}^mC_e$ | 30 | 13 |
| 580065 | $T_{es}A_{es}{}^mC_{es}{}^mC_{es}A_{es}{}^mC_{es}T_{es}T_{es}T_{es}{}^mC_{es}A_{es}T_{es}T_{es}T_{es}T_{es}{}^mC_{es}T_{es}G_e$ | 67 | 14 |
| 580066 | $^mC_{es}T_{es}{}^mC_{es}T_{es}A_{es}{}^mC_{es}{}^mC_{es}A_{es}{}^mC_{es}T_{es}T_{es}T_{es}{}^mC_{es}A_{es}T_{es}T_{es}T_{es}T_e$ | 70 | 15 |
| 580067 | $A_{es}T_{es}T_{es}{}^mC_{es}T_{es}{}^mC_{es}T_{es}A_{es}{}^mC_{es}{}^mC_{es}A_{es}{}^mC_{es}T_{es}T_{es}T_{es}{}^mC_{es}A_{es}T_e$ | 61 | 16 |
| 580068 | $G_{es}A_{es}G_{es}A_{es}T_{es}T_{es}{}^mC_{es}T_{es}{}^mC_{es}T_{es}A_{es}{}^mC_{es}{}^mC_{es}A_{es}{}^mC_{es}T_{es}T_{es}T_e$ | 16 | 17 |
| 580069 | $^mC_{es}T_{es}G_{es}G_{es}A_{es}G_{es}A_{es}T_{es}T_{es}{}^mC_{es}T_{es}{}^mC_{es}T_{es}A_{es}{}^mC_{es}{}^mC_{es}A_{es}{}^mC_e$ | 26 | 18 |
| 580070 | $A_{es}T_{es}{}^mC_{es}{}^mC_{es}T_{es}G_{es}G_{es}A_{es}G_{es}A_{es}T_{es}T_{es}{}^mC_{es}T_{es}{}^mC_{es}T_{es}A_{es}{}^mC_e$ | 34 | 19 |
| 580071 | $G_{es}T_{es}{}^mC_{es}A_{es}T_{es}{}^mC_{es}{}^mC_{es}T_{es}G_{es}G_{es}A_{es}G_{es}A_{es}T_{es}T_{es}{}^mC_{es}T_{es}{}^mC_e$ | 12 | 20 |
| 580072 | $A_{es}A_{es}A_{es}G_{es}Tes{}^mC_{es}A_{es}T_{es}{}^mC_{es}{}^mC_{es}T_{es}G_{es}G_{es}A_{es}G_{es}A_{es}T_{es}T_e$ | 12 | 21 |
| 580073 | $A_{es}T_{es}{}^mC_{es}A_{es}A_{es}A_{es}G_{es}T_{es}{}^mC_{es}A_{es}T_{es}{}^mC_{es}{}^mC_{es}T_{es}G_{es}G_{es}A_{es}G_e$ | 9 | 22 |
| 580074 | $G_{es}A_{es}A_{es}A_{es}T_{es}{}^mC_{es}A_{es}A_{es}A_{es}G_{es}T_{es}{}^mC_{es}A_{es}T_{es}{}^mC_{es}{}^mC_{es}T_{es}G_e$ | 18 | 23 |
| 580075 | $G_{es}T_{es}T_{es}G_{es}A_{es}A_{es}A_{es}T_{es}{}^mC_{es}A_{es}A_{es}A_{es}G_{es}T_{es}{}^mC_{es}A_{es}T_{es}{}^mC_e$ | 10 | 24 |
| 580076 | $A_{es}T_{es}A_{es}G_{es}T_{es}T_{es}G_{es}A_{es}A_{es}A_{es}T_{es}{}^mC_{es}A_{es}A_{es}A_{es}G_{es}T_{es}{}^mC_e$ | 13 | 25 |
| 580077 | $T_{es}T_{es}A_{es}T_{es}A_{es}G_{es}T_{es}T_{es}G_{es}A_{es}A_{es}A_{es}T_{es}{}^mC_{es}A_{es}A_{es}A_e$ | 23 | 26 |

TABLE 1-continued

Effects of uniform 2'-MOE modified oligonucleotides on human STAT3

| ISIS No. | Sequence (5' to 3') | % UTC | SEQ ID No. |
|---|---|---|---|
| 580078 | $G_{es}G_{es}T_{es}T_{es}T_{es}T_{es}A_{es}T_{es}A_{es}G_{es}T_{es}T_{es}G_{es}A_{es}A_{es}A_{es}T_{es}{}^mC_e$ | 19 | 27 |
| 580079 | $G_{es}A_{es}G_{es}G_{es}G_{es}T_{es}T_{es}T_{es}A_{es}T_{es}A_{es}G_{es}T_{es}T_{es}G_{es}A_{es}A_e$ | 23 | 28 |
| 580080 | ${}^mC_{es}T_{es}T_{es}G_{es}A_{es}G_{es}G_{es}G_{es}T_{es}T_{es}T_{es}T_{es}A_{es}T_{es}A_{es}A_{es}G_{es}T_{es}T_e$ | 19 | 29 |
| 580081 | $A_{es}{}^mC_{es}T_{es}{}^mC_{es}T_{es}T_{es}G_{es}A_{es}G_{es}G_{es}G_{es}T_{es}T_{es}T_{es}T_{es}A_{es}T_{es}A_e$ | 92 | 30 |
| 580082 | $T_{es}T_{es}G_{es}A_{es}{}^mC_{es}T_{es}{}^mC_{es}T_{es}T_{es}G_{es}A_{es}G_{es}G_{es}G_{es}T_{es}T_{es}T_e$ | 56 | 31 |
| 580083 | $T_{es}{}^mC_{es}{}^mC_{es}T_{es}T_{es}G_{es}A_{es}{}^mC_{es}T_{es}{}^mC_{es}T_{es}T_{es}G_{es}A_{es}G_{es}G_{es}G_{es}T_e$ | 33 | 32 |
| 580084 | $G_{es}{}^mC_{es}{}^mC_{es}T_{es}{}^mC_{es}{}^mC_{es}T_{es}T_{es}G_{es}A_{es}{}^mC_{es}T_{es}{}^mC_{es}T_{es}T_{es}G_{es}A_{es}G_e$ | 21 | 33 |
| 580085 | ${}^mC_{es}T_{es}T_{es}G_{es}{}^mC_{es}{}^mC_{es}T_{es}{}^mC_{es}{}^mC_{es}T_{es}T_{es}G_{es}A_{es}{}^mC_{es}T_{es}{}^mC_{es}T_{es}T_e$ | 31 | 34 |
| 580086 | $T_{es}{}^mC_{es}A_{es}{}^mC_{es}T_{es}T_{es}G_{es}{}^mC_{es}{}^mC_{es}T_{es}{}^mC_{es}{}^mC_{es}T_{es}T_{es}G_{es}A_{es}{}^mC_{es}T_e$ | 27 | 35 |
| 580087 | $T_{es}A_{es}T_{es}T_{es}{}^mC_{es}A_{es}{}^mC_{es}T_{es}T_{es}G_{es}{}^mC_{es}{}^mC_{es}T_{es}{}^mC_{es}{}^mC_{es}T_{es}T_{es}G_e$ | 54 | 36 |
| 580088 | $T_{es}A_{es}A_{es}T_{es}A_{es}T_{es}T_{es}{}^mC_{es}A_{es}{}^mC_{es}T_{es}T_{es}G_{es}{}^mC_{es}{}^mC_{es}T_{es}{}^mC_{es}{}^mC_e$ | 35 | 37 |
| 580089 | ${}^mC_{es}T_{es}{}^mC_{es}T_{es}A_{es}A_{es}T_{es}A_{es}T_{es}T_{es}{}^mC_{es}A_{es}{}^mC_{es}T_{es}T_{es}G_{es}{}^mC_{es}{}^mC_e$ | 44 | 38 |
| 580090 | ${}^mC_{es}A_{es}T_{es}{}^mC_{es}T_{es}{}^mC_{es}T_{es}A_{es}A_{es}T_{es}A_{es}T_{es}T_{es}{}^mC_{es}A_{es}{}^mC_{es}T_{es}T_e$ | 60 | 39 |
| 580091 | $T_{es}A_{es}A_{es}{}^mC_{es}A_{es}T_{es}{}^mC_{es}T_{es}{}^mC_{es}T_{es}A_{es}A_{es}T_{es}A_{es}T_{es}T_{es}{}^mC_{es}A_e$ | 92 | 40 |
| 580092 | $T_{es}T_{es}T_{es}T_{es}A_{es}A_{es}{}^mC_{es}A_{es}T_{es}{}^mC_{es}T_{es}{}^mC_{es}T_{es}A_{es}A_{es}T_{es}A_{es}T_e$ | 85 | 41 |
| 580093 | $A_{es}G_{es}A_{es}T_{es}T_{es}T_{es}T_{es}A_{es}A_{es}{}^mC_{es}A_{es}T_{es}{}^mC_{es}T_{es}{}^mC_{es}T_{es}A_{es}A_e$ | 79 | 42 |
| 580094 | $T_{es}A_{es}G_{es}A_{es}G_{es}A_{es}T_{es}T_{es}T_{es}T_{es}A_{es}A_{es}{}^mC_{es}A_{es}T_{es}{}^mC_{es}T_{es}{}^mC_e$ | 92 | 43 |
| 580095 | $T_{es}T_{es}{}^mC_{es}T_{es}A_{es}G_{es}A_{es}G_{es}A_{es}T_{es}T_{es}T_{es}T_{es}A_{es}A_{es}{}^mC_{es}A_{es}T_e$ | 85 | 44 |

Example 2

Effects of Uniform 2'-MOE Modified Oligonucleotides on Human STAT3

Several modified oligonucleotides from Table 1 were selected and further evaluated for their effects on inhibiting human STAT3 expression in vitro. The 5-10-5 MOE gapmer, ISIS 455291 was included in the study as a positive control for STAT3 knockdown.

HeLa cells were transfected using 3 μg/mL Cytofectin with 0, 3.125, 6.25, 12.5, 25, 50 or 100 nM concentration of modified oligonucleotide as specified in the table below. After a treatment period of approximately 24 hours, RNA was isolated from the cells and the RNA levels of STAT3 were measured by quantitative real-time PCR. Human STAT3 primer probe set RTS199 was used to measure RNA levels. Human STAT3 RNA levels were normalized to total RNA content, as measured by RIBOGREEN®.

The half maximal inhibitory concentration ($IC_{50}$) of each oligonucleotide is presented in the table below and was calculated by plotting the concentrations of oligonucleotides used versus the percent inhibition of human STAT3 RNA expression achieved at each concentration, and noting the concentration of oligonucleotide at which 50% inhibition of human STAT3 RNA expression was achieved compared to the control. Results are presented below.

The $IC_{50}$ of the positive control, 5-10-5 MOE gapmer, ISIS 455291 cannot be determined since it exhibits greater than 90% target knockdown at all doses tested and is denoted as "ND."

TABLE 2

Inhibitory effect of uniform 2'-MOE modified oligonucleotides on human STAT3 expression

| Isis No. | Sequence (5' to 3') | $IC_{50}$ (nM) | SEQ ID No. |
|---|---|---|---|
| 455291 | ${}^mC_{es}A_{es}G_{es}{}^mC_{es}A_{es}G_{ds}A_{ds}T_{ds}{}^mC_{ds}A_{ds}A_{ds}G_{ds}T_{ds}{}^mC_{ds}{}^mC_{ds}A_{es}G_{es}G_{es}G_{es}A_e$ | ND | 4 |
| 580073 | $A_{es}T_{es}{}^mC_{es}A_{es}A_{es}A_{es}G_{es}T_{es}{}^mC_{es}A_{es}T_{es}{}^mC_{es}{}^mC_{es}T_{es}G_{es}G_{es}A_{es}G_e$ | 0.4 | 22 |

TABLE 2-continued

Inhibitory effect of uniform 2'-MOE modified oligonucleotides on human STAT3 expression

| Isis No. | Sequence (5' to 3') | IC$_{50}$ (nM) | SEQ ID No. |
|---|---|---|---|
| 580075 | G$_{es}$T$_{es}$T$_{es}$G$_{es}$A$_{es}$A$_{es}$A$_{es}$T$_{es}$$^m$C$_{es}$A$_{es}$A$_{es}$A$_{es}$G$_{es}$T$_{es}$$^m$C$_{es}$A$_{es}$T$_{es}$$^m$C$_{e}$ | 1.5 | 24 |
| 580078 | G$_{es}$G$_{es}$T$_{es}$T$_{es}$T$_{es}$T$_{es}$A$_{es}$T$_{es}$A$_{es}$G$_{es}$T$_{es}$T$_{es}$G$_{es}$A$_{es}$A$_{es}$A$_{es}$T$_{es}$$^m$C$_{e}$ | 1.7 | 27 |
| 580076 | A$_{es}$T$_{es}$A$_{es}$G$_{es}$T$_{es}$T$_{es}$G$_{es}$A$_{es}$A$_{es}$A$_{es}$T$_{es}$$^m$C$_{es}$A$_{es}$A$_{es}$A$_{es}$G$_{es}$T$_{es}$$^m$C$_{e}$ | 2.5 | 25 |
| 580074 | G$_{es}$A$_{es}$A$_{es}$A$_{es}$T$_{es}$$^m$C$_{es}$A$_{es}$A$_{es}$A$_{es}$G$_{es}$T$_{es}$$^m$C$_{es}$A$_{es}$T$_{es}$$^m$C$_{es}$$^m$C$_{es}$T$_{es}$G$_{e}$ | 5.3 | 23 |
| 580071 | G$_{es}$T$_{es}$$^m$C$_{es}$A$_{es}$T$_{es}$$^m$C$_{es}$$^m$C$_{es}$T$_{es}$G$_{es}$G$_{es}$A$_{es}$G$_{es}$A$_{es}$T$_{es}$T$_{es}$$^m$C$_{es}$T$_{es}$$^m$C$_{e}$ | 5.6 | 20 |
| 580072 | A$_{es}$A$_{es}$A$_{es}$G$_{es}$T$_{es}$$^m$C$_{es}$A$_{es}$T$_{es}$$^m$C$_{es}$$^m$C$_{es}$T$_{es}$G$_{es}$G$_{es}$A$_{es}$G$_{es}$A$_{es}$T$_{es}$T$_{e}$ | 6.1 | 21 |
| 580080 | $^m$C$_{es}$T$_{es}$T$_{es}$G$_{es}$A$_{es}$G$_{es}$G$_{es}$G$_{es}$T$_{es}$T$_{es}$T$_{es}$T$_{es}$A$_{es}$T$_{es}$A$_{es}$G$_{es}$T$_{es}$T$_{e}$ | 7.1 | 29 |
| 580068 | G$_{es}$A$_{es}$G$_{es}$A$_{es}$T$_{es}$T$_{es}$$^m$C$_{es}$T$_{es}$$^m$C$_{es}$T$_{es}$A$_{es}$$^m$C$_{es}$$^m$C$_{es}$A$_{es}$$^m$C$_{es}$T$_{es}$T$_{es}$T$_{e}$ | 7.4 | 17 |
| 580084 | G$_{es}$$^m$C$_{es}$$^m$C$_{es}$T$_{es}$$^m$C$_{es}$$^m$C$_{es}$T$_{es}$T$_{es}$G$_{es}$A$_{es}$$^m$C$_{es}$T$_{es}$$^m$C$_{es}$T$_{es}$T$_{es}$G$_{es}$A$_{es}$G$_{e}$ | 12.0 | 33 |
| 580061 | $^m$C$_{es}$T$_{es}$G$_{es}$T$_{es}$T$_{es}$$^m$C$_{es}$T$_{es}$A$_{es}$G$_{es}$A$_{es}$T$_{es}$$^m$C$_{es}$$^m$C$_{es}$T$_{es}$G$_{es}$T$_{es}$T$_{es}$T$_{e}$ | 10.3 | 9 |

Example 3

Effects of Uniform 2'-MOE Modified Oligonucleotides on Full-Length Human STAT3 Protein Expression ISIS 580073 and 580076 from Table 2 were selected and further evaluated for their effects on full-length human STAT3 protein expression levels. The 5-10-5 MOE gapmers, ISIS 337270 and 455291 were included in the study for comparison.

HeLa cells were transfected using 3 μg/mL Cytofectin with 0, 3.125, 12.5, or 50 nM concentration of modified oligonucleotide as specified in the table below. After a treatment period of approximately 48 hours, protein was isolated from the cells and protein levels of full-length STAT3 were measured by Western blot.

For the Western blot, 15 μg of protein lysate was loaded onto 4-12% Bis-Tris gels and following transfer, the membrane with incubated with primary STAT3 antibody (79D7, Cell Signaling Technology, Inc) at 1:1000 dilution for 1 hour at room temperature. Following washing, the membrane was incubated with anti-rabbit secondary antibody (Abcam) at 1:2500 dilution for 1 hour at room temperature. α-tubulin served as a loading control (Sigma-Aldrich). Results in Table 3 are presented as percent of full-length STAT3 protein expression, relative to untreated control levels and is denoted as "% UTC."

ISIS 337270, T$_{es}$T$_{es}$G$_{es}$G$_{es}$$^m$C$_{es}$T$_{ds}$T$_{ds}$$^m$C$_{ds}$T$_{ds}$$^m$C$_{ds}$A$_{d}$-sA$_{ds}$G$_{ds}$A$_{ds}$T$_{ds}$A$_{es}$$^m$C$_{es}$$^m$C$_{es}$T$_{es}$G$_{e}$, designated herein as SEQ ID NO: 45. Subscripts "e" indicate 2'-MOE modified nucleosides. Subscripts "d" indicate β-D-2'-deoxyribonucleosides. Subscripts "s" indicate phosphorothioate internucleoside linkages. Superscripts "m" indicate 5-methylcytosines.

TABLE 3

Effects of uniform 2'-MOE modified oligonucleotides on full-length human STAT3 protein expression

| ISIS No. | Conc (nM) | % UTC | SEQ ID No. |
|---|---|---|---|
| 580073 | 3.125 | 78 | 22 |
|  | 12.5 | 15 |  |
|  | 50 | 0 |  |
| 580076 | 3.125 | 111 | 25 |
|  | 12.5 | 35 |  |
|  | 50 | 7 |  |
| 337270 | 3.125 | 50 | 45 |
|  | 12.5 | 16 |  |
|  | 50 | 0 |  |
| 455291 | 3.125 | 1 | 4 |
|  | 12.5 | 0 |  |
|  | 50 | 0 |  |

Example 4

Effects of Uniform 2'-MOE Modified Oligonucleotides on Human STAT3

Several modified oligonucleotides from Table 1 were selected and further evaluated for their inhibitory effect targeting various regions of human STAT3 expression in vitro. The 5-10-5 MOE gapmers, ISIS 337270 and 455291 were included in the study for comparison.

HeLa cells were transfected using 3 μg/mL Cytofectin with 0, 3.125, 6.25, 12.5, 25 or 50 nM concentration of modified oligonucleotide as specified in the table below. After a treatment period of approximately 24 hours, RNA was isolated from the cells and the RNA levels of STAT3 were measured by quantitative real-time PCR. Different primer probe sets were used to detect different regions of STAT3 and are presented below. Human STAT3 RNA levels were normalized to total RNA content, as measured by RIBOGREEN®.

Human primer probe set RTS199 (forward sequence 5'-ACATGCCACTTTGGTGTTTCATAA-3', designated herein as SEQ ID NO: 46; reverse sequence 5'-TCTTCG-TAGATTGTGCTGATAGAGAAC-3', designated herein as SEQ ID NO: 47; probe sequence 5'-CAGTATAGCCGCT-TCCTGCAAGAGTCGAA-3', designated herein as SEQ ID NO: 48).

Human primer probe set hSTAT3_EXON8_LTS01120 (forward sequence, 5'-GAAGAGGCGGCAACAGATTG-3', designated herein as SEQ ID NO: 49; reverse sequence, 5'-TTCTAGCCGATCTAGGCAGATGT-3', designated herein as SEQ ID NO: 50; probe sequence, 5'-CTGCATTG-GAGGCCCGCCC-3', designated herein as SEQ ID NO: 51).

Human primer probe set RTS3235 (forward sequence, 5'-AAGTTTATCTGTGTGACACCAACGA-3', designated herein as SEQ ID NO: 52; reverse sequence, 5'-CTTCAC-CATTATTTCCAAACTGCAT-3', designated herein as SEQ ID NO: 53; probe sequence, 5'-TGCCGATGTC-CCCCCGCA-3', designated herein as SEQ ID NO: 54).

The half maximal inhibitory concentration ($IC_{50}$) of each oligonucleotide was calculated using similar methods as described previously in Example 2 and the results are presented in Table 4.

TABLE 4

Inhibitory effect of uniform 2'-MOE modified oligonucleotides on various regions of human STAT3

| Isis No. | Region | Primer Probe Set | $IC_{50}$ (nM) | SEQ ID No. |
|---|---|---|---|---|
| 580073 | Exon 3 | RTS199 | 3.4 | 22 |
|  | Exon 8 | hSTAT3_EXON8_LTS01120 | 3.8 |  |
|  | Exon22/23 | RTS3235 | 2.7 |  |
| 580076 | Exon 3 | RTS199 | 9.9 | 25 |
|  | Exon 8 | hSTAT3_EXON8_LTS01120 | 7.7 |  |
|  | Exon22/23 | RTS3235 | 9.5 |  |
| 337270 | Exon 3 | RTS199 | 4.5 | 45 |
|  | Exon 8 | hSTAT3_EXON8_LTS01120 | 4.3 |  |
|  | Exon22/23 | RTS3235 | 4.1 |  |
| 455291 | Exon 3 | RTS199 | 0.05 | 4 |
|  | Exon 8 | hSTAT3_EXON8_LTS01120 | 0.005 |  |
|  | Exon22/23 | RTS3235 | 0.01 |  |

Example 5

Effects of Uniform 2'-MOE Modified Oligonucleotides on Promoting Human STAT3 Exon Skipping Several modified oligonucleotides from Table 1 were selected and further evaluated for their effect on promoting human STAT3 exon 6 skipping in vitro. The 5-10-5 MOE gapmer, ISIS 455291 was included in the study for comparison.

HeLa cells were transfected using 3 μg/mL Cytofectin with 0 or 50 nM concentration of modified oligonucleotide. After a treatment period of approximately 24 hours, standard RT-PCR for STAT3 RNA expression was performed using the following primers: STAT3 exon 5 forward (5'-TG-GAGCAGCACCTTCAGGATGT-3' SEQ ID NO: 55) and STAT3 exon 7 reverse (5'-TCCAGCGCAGTGAGCATCT-GTT-3' SEQ ID NO: 56). Quantification of STAT3 exon 6 skipping was measured using Kodak Gel Logic imager as a ratio of exon 6 skipped transcript/total expression*100 and corrected for intensity of ethidium bromide staining Results are presented in Table 5.

As illustrated, treatment with uniform 2'-MOE modified oligonucleotides promotes human STAT3 exon skipping.

TABLE 5

Effects of uniform 2'-MOE modified oligonucleotides on promoting human STAT3 exon skipping

| ISIS No. | STAT3 exon 6 skipping (%) |
|---|---|
| UTC | 1 |
| 580061 | 27 |
| 580073 | 47 |
| 580076 | 40 |
| 580080 | 28 |
| 455291 | 7 |

UTC = untreated control

Example 6

Effects of Uniform 2'-MOE Modified Oligonucleotides on Promoting Human STAT3 Nonsense-Mediated Decay (NMD)

Nonsense-mediated decay (NMD) was inhibited in HeLa cells by transfection with 10 nM concentration of negative control siRNA or siRNA targeting the NMD factors, UPF1 and SMG6 for 48 hours, followed by 0 or 50 nM concentration of modified oligonucleotide. After 24 hours, RNA was analyzed by quantitative real-time PCR and standard RT-PCR as previously described. Results in Table 6 are presented as percent of STAT3 RNA expression, relative to untreated control levels and is denoted as "% UTC". Results in Table 7 are presented as percent of STAT3 exon 6 skipping, relative to untreated control levels.

As illustrated, NMD inhibition by the presence of UPF1/SMG6 siRNA partially prevents the ability of uniform 2'-MOE modified oligonucleotide, ISIS 580073 to knockdown STAT3 expression, which indicates that STAT3 knockdown is mediated through the NMD pathway (Table 6). Further, when NMD is inhibited, there is more exon 6 skipped transcript present, which indicates that degradation of exon 6 skipped transcript is also mediated through the NMD pathway (Table 7).

The siRNAs used in the study were purchased from Dharmacon. The composition of the sense strand is presented in Table 8. The internucleoside linkages throughout each siRNA are phosphodiester (P=O) linkages. Nucleosides with capitalized letters indicate ribonucleosides (RNAs). Nucleosides with small letters "tt" indicate 2'-β-deoxyribonucleosides overhang.

TABLE 6

NMD inhibition partially prevents ASO-mediated knockdown of STAT3

| Modified Oligonucleotide Treatment | siRNA Treatment | Regions | % UTC |
|---|---|---|---|
| ISIS 580073 | Negative control | Exon 3 | 17 |
|  |  | Exon 8 | 17 |
|  |  | Exon 22/23 | 15 |
| ISIS 580073 | UPF1/SMG6 | Exon 3 | 46 |
|  |  | Exon 8 | 49 |
|  |  | Exon 22/23 | 41 |

TABLE 7

NMD inhibition stabilizes STAT3 exon 6 skipped transcript

| Modified Oligonucleotide Treatment | siRNA treatment | STAT3 exon 6 skipping (%) |
|---|---|---|
| UTC | Negative control | 4 |
|  | UPF1/SMG6 | 14 |
| 580073 | Negative control | 49 |
|  | UPF1/SMG6 | 74 |

UTC = Untreated control

TABLE 8 siRNAs

| siRNA | Composition of sense strand (5' to 3') | SEQ ID NO. |
|---|---|---|
| UPF1 | GAUGCAGUUCCGCUCCAUUtt | 57 |
| SMG6 | GCUGCAGGUUACUUACAAGtt | 58 |

Example 7

Effect of Inhibiting Endogenous Decay Enzymes on Ability of Uniform 2' MOE Modified Oligonucleotide, ISIS 580073 to Knockdown STAT3

HeLa cells were transfected with 10 nM each of negative control siRNA or siRNA targeting the decay factors as shown below for 48 hours, followed by treatment with ISIS 580073 at 0 or 50 nM concentration. After 24 hours, RNA was isolated and analyzed by qRT-PCR as described previously. Results in Table 9 are presented as percent of STAT3 expression, relative to untreated control levels and is denoted as "% UTC".

As illustrated, XRN1 inhibition partially prevents knockdown of STAT3 downstream of the modified oligonucleotide binding site but not upstream of the modified oligonucleotide binding site, suggesting entry of the XRN1 exonuclease near the modified oligonucleotide binding site.

SMG6 is an endonuclease recruited to NMD substrates following UPF1 phosphorylation. To determine if UPF1 and SMG6 are required for the generation of the cleaved product, HeLa cells were transfected with UPF1 and SMG6 siRNA in the same manner as described above.

5' RACE was also performed to identify any cleavage products generated by the modified oligonucleotide. Quantification of the 5' RACE product was determined by measuring the ratio of the RACE band intensity relative to the GAPDH band intensity.

As illustrated, results in Table 10 show that treatment with modified oligonucleotide resulted in STAT3 cleavage and the cleaved product is stabilized by XRN1 inhibition. Sequencing of the 5' RACE product shows that the cleavage sites are around the premature termination codons generated by STAT3 exon 6 skipping. Further, the intensity of the 5' RACE product is much weaker when SMG6 or UPF1 is knocked down which suggests that NMD recognition by UPF1 and SMG6 cleavage occurs prior to XRN1 degradation.

The siRNAs used in the study were purchased from Dharmacon. The composition of the sense strand is presented in Table 11. The internucleoside linkages throughout each siRNA are phosphodiester (P=O) linkages. Nucleosides with capitalized letters indicate ribonucleosides (RNAs). Nucleosides with small letters "tt" indicate 2'-β-deoxyribonucleosides overhang.

TABLE 9

XRN1 degrades STAT3 downstream of the ASO binding site

| Modified Oligonucleotide Treatment | siRNA treatment | Regions | Primer Probe Set | % UTC |
|---|---|---|---|---|
| 580073 | Negative control | Exon 3 | RTS199 | 22 |
|  |  | Exon 8 | hSTAT3_EXON8_LTS01120 | 24 |
|  |  | Exon 22/23 | RTS3235 | 20 |
|  | XRN1 | Exon 3 | RTS199 | 18 |
|  |  | Exon 8 | hSTAT3_EXON8_LTS01120 | 30 |
|  |  | Exon 22/23 | RTS3235 | 33 |
|  | XRN1/SMG6 | Exon 3 | RTS199 | 23 |
|  |  | Exon 8 | hSTAT3_EXON8_LTS01120 | 32 |
|  |  | Exon 22/23 | RTS3235 | 33 |
|  | XRN1/UPF1 | Exon 3 | RTS199 | 44 |
|  |  | Exon 8 | hSTAT3_EXON8_LTS01120 | 52 |
|  |  | Exon 22/23 | RTS3235 | 47 |
|  | XRN1/SMG6/UPF1 | Exon 3 | RTS199 | 55 |
|  |  | Exon 8 | hSTAT3_EXON8_LTS01120 | 67 |
|  |  | Exon 22/23 | RTS3235 | 59 |

TABLE 10

Modified Oligonucleotide results in STAT3 cleavage by SMG6 and degradation by XRN1

| Modified Oligonucleotide Treatment | siRNA treatment | Intensity of 5' RACE product |
|---|---|---|
| UTC | Negative control | 0.02 |
| 580073 | Negative control | 0.06 |
|  | XRN1 | 3.79 |
|  | XRN1/SMG6 | 2.05 |
|  | XRN1/UPF1 | 1.35 |
|  | XRN1/SMG6/UPF1 | 2.12 |

TABLE 11 siRNAs

| siRNA | Composition of sense strand (5' to 3') | SEQ ID NO. |
|---|---|---|
| XRN1 | AGAUGAACUUACCGUAGAAtt | 59 |
| SMG6 | GCUGCAGGUUACUUACAAGtt | 60 |
| UPF1 | GAUGCAGUUCCGCUCCAUUtt | 61 |

Example 8

Effects of Uniform 2'-MOE Modified Oligonucleotides on Human Heterogeneous Nuclear RiboNucleoProtein H1 (HNRNPH1)

A series of modified oligonucleotides were designed to target human HNRNPH1 exon 4 via the nonsense mediated decay mechanism and were screened for their effects on reducing human HNRNPH1 expression in vitro. The 5-10-5 MOE gapmer, ISIS 172290 was included in the study as a positive control for human HNRNPH1 knockdown. This gapmer inhibits HNRNPH1 RNA expression level via an RNase H-dependent mechanism.

The modified oligonucleotides are 18 nucleosides in length, wherein each nucleoside has a 2'-MOE modification and is denoted as subscript "e". Subscript "d" indicates β-D-2'-deoxyribonucleosides. Each internucleoside linkage throughout the modified oligonucleotide are phosphorothioate internucleoside linkages (P=S) and is denoted as subscript "s". All cytosine residues throughout the modified oligonucleotides are 5-methylcytosines and are denoted as superscripts "m".

HeLa cells were transfected using 3 μg/mL Cytofectin with 50 nM concentration of modified oligonucleotide. After a treatment period of approximately 24 hours, RNA was isolated from the cells and the RNA levels of HNRNPH1 transcripts were measured by quantitative real-time PCR. Human primer probe set HTS3648 was used to measure RNA levels. HNRNPH1 RNA levels were adjusted according to total RNA content, as measured by RIBOGREEN®. Results in Table 12 are presented as percent of HNRNPH1 RNA expression, relative to untreated control levels and is denoted as "% UTC."

Human primer probe set HTS3648 (forward sequence 5'-GAGCAGTGAACAGCAGCTACTACAG-3', designated herein as SEQ ID NO: 62; reverse sequence 5'-TGACCAAGAGTCAGTGATCAGGAT-3', designated herein as SEQ ID NO: 63; probe sequence 5'-CCGTGCATCTATGGGCGTGAACG-3', designated herein as SEQ ID NO: 64).

TABLE 12

Effects of uniform 2'-MOE modified oligonucleotides on human HNRNPH1

| ISIS No. | Sequence (5' to 3') | % UTC | SEQ ID NO. |
|---|---|---|---|
| 172290 | $A_{es}G_{es}{}^mC_{es}T_{es}T_{es}{}^mC_{ds}A_{ds}{}^mC_{ds}T_{ds}G_{ds}T_{ds}T_{ds}A_{ds}{}^mC_{ds}A_{ds}T_{es}{}^mC_{es}{}^mC_{es}T_{es}A_{e}$ | 8 | 65 |
| 580017 | $T_{es}T_{es}{}^mC_{es}A_{es}A_{es}{}^mC_{es}{}^mC_{es}{}^mC_{es}A_{es}A_{es}G_{es}G_{es}A_{es}{}^mC_{es}A_{es}A_{es}A_{es}T_{e}$ | 66 | 66 |
| 580018 | $A_{es}{}^mC_{es}{}^mC_{es}{}^mC_{es}T_{es}T_{es}{}^mC_{es}A_{es}A_{es}{}^mC_{es}{}^mC_{es}{}^mC_{es}A_{es}A_{es}G_{es}G_{es}A_{es}{}^mC_{e}$ | 78 | 67 |
| 580019 | $T_{es}{}^mC_{es}{}^mC_{es}A_{es}A_{es}{}^mC_{es}{}^mC_{es}{}^mC_{es}T_{es}T_{es}{}^mC_{es}A_{es}A_{es}{}^mC_{es}{}^mC_{es}{}^mC_{es}A_{es}A_{e}$ | 96 | 68 |
| 580020 | $G_{es}A_{es}T_{es}T_{es}T_{es}{}^mC_{es}{}^mC_{es}A_{es}A_{es}{}^mC_{es}{}^mC_{es}{}^mC_{es}T_{es}T_{es}{}^mC_{es}A_{es}A_{es}{}^mC_{e}$ | 67 | 69 |
| 580021 | $G^{esm}C_{es}A_{es}{}^mC_{es}G_{es}A_{es}T_{es}T_{es}T_{es}{}^mC_{es}{}^mC_{es}A_{es}A_{es}{}^mC_{es}{}^mC_{es}{}^mC_{es}T_{es}T_{e}$ | 53 | 70 |
| 580022 | $T_{es}T_{es}G_{es}G_{es}{}^mC_{es}A_{es}{}^mC_{es}G_{es}A_{es}T_{es}T_{es}T_{es}{}^mC_{es}{}^mC_{es}A_{es}A_{es}{}^mC_{e}$ | 47 | 71 |
| 580023 | ${}^mC_{es}{}^mC_{es}{}^mC_{es}A_{es}T_{es}T_{es}T_{es}G_{es}G_{es}{}^mC_{es}A_{es}{}^mC_{es}G_{es}A_{es}T_{es}T_{es}T_{es}{}^mC_{e}$ | 54 | 72 |
| 580024 | $T_{es}T_{es}A_{es}T_{es}{}^mC_{es}{}^mC_{es}{}^mC_{es}A_{es}T_{es}T_{es}T_{es}G_{es}G_{es}{}^mC_{es}A_{es}{}^mC_{es}G_{es}A_{e}$ | 55 | 73 |
| 580025 | $A_{es}A_{es}T_{es}G_{es}T_{es}T_{es}A_{es}T_{es}{}^mC_{es}{}^mC_{es}{}^mC_{es}A_{es}T_{es}T_{es}T_{es}G_{es}G_{es}{}^mC_{e}$ | 52 | 74 |
| 580026 | ${}^mC_{es}G_{es}G_{es}{}^mC_{es}A_{es}A_{es}T_{es}G_{es}T_{es}T_{es}A_{es}T_{es}{}^mC_{es}{}^mC_{es}{}^mC_{es}A_{es}T_{es}T_{e}$ | 49 | 75 |
| 580027 | ${}^mC_{es}{}^mC_{es}A_{es}{}^mC_{es}{}^mC_{es}G_{es}G_{es}{}^mC_{es}A_{es}A_{es}T_{es}G_{es}T_{es}T_{es}A_{es}T_{es}{}^mC_{es}{}^mC_{e}$ | 41 | 76 |
| 580028 | $A_{es}A_{es}G_{es}T_{es}{}^mC_{es}{}^mC_{es}A_{es}{}^mC_{es}{}^mC_{es}G_{es}G_{es}{}^mC_{es}A_{es}A_{es}T_{es}G_{es}T_{es}T_{e}$ | 41 | 77 |
| 580029 | ${}^mC_{es}T_{es}G_{es}G_{es}A_{es}A_{es}G_{es}T_{es}{}^mC_{es}{}^mC_{es}A_{es}{}^mC_{es}{}^mC_{es}G_{es}G_{es}{}^mC_{es}A_{es}A_{e}$ | 31 | 78 |
| 580030 | $T_{es}{}^mC_{es}{}^mC_{es}{}^mC_{es}{}^mC_{es}{}^mC_{es}T_{es}G_{es}G_{es}A_{es}A_{es}G_{es}T_{es}{}^mC_{es}{}^mC_{es}A_{es}{}^mC_{es}{}^mC_{es}G_{e}$ | 54 | 79 |
| 580031 | ${}^mC_{es}T_{es}{}^mC_{es}{}^mC_{es}T_{es}{}^mC_{es}{}^mC_{es}{}^mC_{es}{}^mC_{es}T_{es}G_{es}G_{es}A_{es}A_{es}G_{es}T_{es}{}^mC_{es}{}^mC_{e}$ | 54 | 80 |
| 580032 | ${}^mC_{es}G_{es}T_{es}A_{es}{}^mC_{es}T_{es}{}^mC_{es}{}^mC_{es}T_{es}{}^mC_{es}{}^mC_{es}{}^mC_{es}{}^mC_{es}T_{es}G_{es}G_{es}A_{es}A_{e}$ | 64 | 81 |
| 580033 | ${}^mC_{es}{}^mC_{es}{}^mC_{es}{}^mC_{es}{}^mC_{es}G_{es}T_{es}A_{es}{}^mC_{es}T_{es}{}^mC_{es}{}^mC_{es}T_{es}{}^mC_{es}{}^mC_{es}{}^mC_{es}{}^mC_{es}T_{e}$ | 114 | 82 |
| 580034 | $G_{es}{}^mC_{es}{}^mC_{es}T_{es}{}^mC_{es}{}^mC_{es}{}^mC_{es}{}^mC_{es}{}^mC_{es}G_{es}T_{es}A_{es}{}^mC_{es}T_{es}{}^mC_{es}{}^mC_{es}T_{es}{}^mC_{e}$ | 123 | 83 |

TABLE 12-continued

Effects of uniform 2'-MOE modified oligonucleotides on human HNRNPH1

| ISIS No. | Sequence (5' to 3') | % UTC | SEQ ID NO. |
|---|---|---|---|
| 580035 | $G_{es}A_{es}A_{es}G_{es}G_{es}{}^mC_{es}{}^mC_{es}T_{es}{}^mC_{es}{}^mC_{es}{}^mC_{es}{}^mC_{es}{}^mC_{es}G_{es}T_{es}A_{es}{}^mC_{es}T_e$ | 88 | 84 |
| 580036 | $G_{es}{}^mC_{es}A_{es}{}^mC_{es}G_{es}A_{es}A_{es}G_{es}G_{es}{}^mC_{es}{}^mC_{es}T_{es}{}^mC_{es}{}^mC_{es}{}^mC_{es}{}^mC_{es}{}^mC_{es}G_e$ | 71 | 85 |
| 580037 | $A_{es}A_{es}{}^mC_{es}T_{es}G_{es}{}^mC_{es}A_{es}{}^mC_{es}G_{es}A_{es}A_{es}G_{es}G_{es}{}^mC_{es}{}^mC_{es}T_{es}{}^mC_{es}{}^mC_e$ | 43 | 86 |
| 580038 | $A_{es}G_{es}{}^mC_{es}A_{es}A_{es}A_{es}{}^mC_{es}T_{es}G_{es}{}^mC_{es}A_{es}{}^mC_{es}G_{es}A_{es}A_{es}G_{es}G_{es}{}^mC_e$ | 37 | 87 |
| 580039 | $G_{es}T_{es}G_{es}A_{es}A_{es}G_{es}{}^mC_{es}A_{es}A_{es}A_{es}{}^mC_{es}T_{es}G_{es}{}^mC_{es}A_{es}{}^mC_{es}G_{es}A_e$ | 36 | 88 |
| 580040 | $T_{es}{}^mC_{es}{}^mC_{es}T_{es}G_{es}T_{es}G_{es}A_{es}A_{es}G_{es}{}^mC_{es}A_{es}A_{es}A_{es}{}^mC_{es}T_{es}G_{es}{}^mC_e$ | 37 | 89 |
| 580041 | $T_{es}A_{es}T_{es}T_{es}T_{es}{}^mC_{es}{}^mC_{es}T_{es}G_{es}T_{es}G_{es}A_{es}A_{es}G_{es}{}^mC_{es}A_{es}A_{es}A_e$ | 43 | 90 |
| 580042 | ${}^mC_{es}A_{es}G_{es}{}^mC_{es}T_{es}A_{es}T_{es}T_{es}T_{es}{}^mC_{es}{}^mC_{es}T_{es}G_{es}T_{es}G_{es}A_{es}A_{es}G_e$ | 33 | 91 |
| 580043 | $T_{es}T_{es}T_{es}T_{es}{}^mC_{es}A_{es}G_{es}{}^mC_{es}T_{es}A_{es}T_{es}T_{es}T_{es}{}^mC_{es}{}^mC_{es}T_{es}G_{es}T_e$ | 37 | 92 |
| 580044 | $A_{es}G_{es}{}^mC_{es}{}^mC_{es}T_{es}T_{es}T_{es}T_{es}{}^mC_{es}A_{es}G_{es}{}^mC_{es}T_{es}A_{es}T_{es}T_{es}T_{es}{}^mC_e$ | 52 | 93 |
| 580045 | $T_{es}T_{es}A_{es}G_{es}A_{es}G_{es}{}^mC_{es}{}^mC_{es}T_{es}T_{es}T_{es}T_{es}{}^mC_{es}A_{es}G_{es}{}^mC_{es}T_{es}A_e$ | 53 | 94 |
| 580046 | $T_{es}T_{es}{}^mC_{es}T_{es}T_{es}T_{es}A_{es}G_{es}A_{es}G_{es}{}^mC_{es}{}^mC_{es}T_{es}T_{es}T_{es}T_{es}{}^mC_{es}A_e$ | 36 | 95 |
| 580047 | $G_{es}T_{es}G_{es}T_{es}T_{es}T_{es}{}^mC_{es}T_{es}T_{es}T_{es}A_{es}G_{es}A_{es}G_{es}{}^mC_{es}{}^mC_{es}T_{es}T_e$ | 40 | 96 |
| 580048 | ${}^mC_{es}{}^mC_{es}T_{es}T_{es}G_{es}T_{es}G_{es}T_{es}T_{es}T_{es}{}^mC_{es}T_{es}T_{es}T_{es}A_{es}G_{es}A_{es}G_e$ | 79 | 97 |
| 580049 | ${}^mC_{es}T_{es}T_{es}T_{es}{}^mC_{es}{}^mC_{es}T_{es}T_{es}G_{es}T_{es}G_{es}T_{es}T_{es}T_{es}{}^mC_{es}T_{es}T_{es}T_e$ | 62 | 98 |
| 580050 | $T_{es}A_{es}T_{es}T_{es}{}^mC_{es}T_{es}T_{es}T_{es}{}^mC_{es}{}^mC_{es}T_{es}T_{es}G_{es}T_{es}G_{es}T_{es}T_{es}T_e$ | 79 | 99 |
| 580051 | $G_{es}{}^mC_{es}{}^mC_{es}{}^mC_{es}T_{es}A_{es}T_{es}T_{es}{}^mC_{es}T_{es}T_{es}T_{es}{}^mC_{es}{}^mC_{es}T_{es}T_{es}G_{es}T_e$ | 98 | 100 |
| 580052 | ${}^mC_{es}T_{es}G_{es}T_{es}G_{es}{}^mC_{es}{}^mC_{es}{}^mC_{es}T_{es}A_{es}T_{es}T_{es}{}^mC_{es}T_{es}T_{es}T_{es}{}^mC_{es}{}^mC_e$ | 53 | 101 |
| 580053 | ${}^mC_{es}{}^mC_{es}A_{es}{}^mC_{es}{}^mC_{es}T_{es}G_{es}T_{es}G_{es}{}^mC_{es}{}^mC_{es}{}^mC_{es}T_{es}A_{es}T_{es}T_{es}{}^mC_{es}T_e$ | 75 | 102 |
| 580054 | $A_{es}T_{es}{}^mC_{es}{}^mC_{es}{}^mC_{es}{}^mC_{es}A_{es}{}^mC_{es}{}^mC_{es}T_{es}G_{es}T_{es}G_{es}{}^mC_{es}{}^mC_{es}{}^mC_{es}T_{es}A_e$ | 160 | 103 |
| 580055 | $A_{es}T_{es}{}^mC_{es}{}^mC_{es}A_{es}T_{es}{}^mC_{es}{}^mC_{es}{}^mC_{es}{}^mC_{es}A_{es}{}^mC_{es}{}^mC_{es}T_{es}G_{es}T_{es}G_{es}{}^mC_e$ | 131 | 104 |
| 580056 | $A_{es}A_{es}{}^mC_{es}{}^mC_{es}A_{es}T_{es}{}^mC_{es}{}^mC_{es}A_{es}T_{es}{}^mC_{es}{}^mC_{es}{}^mC_{es}{}^mC_{es}A_{es}{}^mC_{es}{}^mC_{es}T_e$ | 114 | 105 |

Example 9

Effects of Uniform 2'-MOE Modified Oligonucleotides on Human HNRNPH1

Several modified oligonucleotides from Table 12 were selected and further evaluated for their effects on inhibiting human HNRNPH1 expression in vitro. The 5-10-5 MOE gapmer, ISIS 172290 was included in the study as a positive control.

HeLa cells were transfected using 3 μg/mL Cytofectin with 0, 3.125, 6.25, 12.5, 25, 50 or 100 nM concentration of modified oligonucleotide as specified in the table below. After a treatment period of approximately 24 hours, RNA was isolated from the cells and the RNA levels of human HNRNPH1 were measured by quantitative real-time PCR. Human HNRNPH1 primer probe set HTS3648 was used to measure RNA levels. Human HNRNPH1 RNA levels were adjusted according to total RNA content, as measured by RIBOGREEN®.

The half maximal inhibitory concentration ($IC_{50}$) of each oligonucleotide is presented in the table below and was calculated using similar methods as described previously.

The $IC_{50}$ of the positive control, 5-10-5 MOE gapmer, ISIS 172290 cannot be determined since it exhibits greater than 50% target knockdown at all doses tested and is denoted as "ND."

TABLE 13

Inhibitory effect of uniform 2'-MOE modified oligonucleotides on human HNRNPH1

| Isis No. | Sequence (5' to 3') | IC$_{50}$ (nM) | SEQ ID NO. |
|---|---|---|---|
| 172290 | $A_{es}G_{es}{}^mC_{es}T_{es}T_{es}{}^mC_{ds}A_{ds}{}^mC_{ds}T_{ds}G_{ds}T_{ds}T_{ds}A_{ds}{}^mC_{ds}A_{ds}T_{es}{}^mC_{es}{}^mC_{es}T_{es}A_e$ | ND | 65 |
| 580042 | ${}^mC_{es}A_{es}G_{es}{}^mC_{es}T_{es}A_{es}T_{es}T_{es}T_{es}{}^mC_{es}{}^mC_{es}T_{es}G_{es}T_{es}G_{es}A_{es}A_{es}G_e$ | 3.3 | 91 |
| 580038 | $A_{es}G_{es}{}^mC_{es}A_{es}A_{es}A_{es}{}^mC_{es}T_{es}G_{es}{}^mC_{es}A_{es}{}^mC_{es}G_{es}A_{es}A_{es}G_{es}G_{es}{}^mC_e$ | 4.3 | 87 |
| 580046 | $T_{es}T_{es}{}^mC_{es}T_{es}T_{es}T_{es}A_{es}G_{es}A_{es}G_{es}{}^mC_{es}{}^mC_{es}T_{es}T_{es}T_{es}T_{es}{}^mC_{es}A_e$ | 4.4 | 95 |
| 580027 | ${}^mC_{es}{}^mC_{es}A_{es}{}^mC_{es}{}^mC_{es}G_{es}G_{es}{}^mC_{es}A_{es}A_{es}T_{es}G_{es}T_{es}A_{es}T_{es}{}^mC_{es}{}^mC_e$ | 6.5 | 76 |
| 580040 | $T_{es}{}^mC_{es}{}^mC_{es}T_{es}G_{es}T_{es}G_{es}A_{es}A_{es}G_{es}{}^mC_{es}A_{es}A_{es}A_{es}{}^mC_{es}T_{es}G_{es}{}^mC_e$ | 7.8 | 89 |
| 580041 | $T_{es}A_{es}T_{es}T_{es}T_{es}{}^mC_{es}{}^mC_{es}T_{es}G_{es}T_{es}G_{es}A_{es}A_{es}G_{es}{}^mC_{es}A_{es}A_{es}A_e$ | 7.8 | 90 |
| 580047 | $G_{es}T_{es}G_{es}T_{es}T_{es}T_{es}{}^mC_{es}T_{es}T_{es}T_{es}A_{es}G_{es}A_{es}G_{es}{}^mC_{es}{}^mC_{es}T_{es}T_e$ | 8.0 | 96 |
| 580039 | $G_{es}T_{es}G_{es}A_{es}A_{es}G_{es}{}^mC_{es}A_{es}A_{es}A_{es}{}^mC_{es}T_{es}G_{es}{}^mC_{es}A_{es}{}^mC_{es}G_{es}A_e$ | 8.1 | 88 |
| 580028 | $A_{es}A_{es}G_{es}T_{es}{}^mC_{es}{}^mC_{es}A_{es}{}^mC_{es}{}^mC_{es}G_{es}G_{es}{}^mC_{es}A_{es}A_{es}T_{es}G_{es}T_{es}T_e$ | 8.9 | 77 |
| 580029 | ${}^mC_{es}T_{es}G_{es}G_{es}A_{es}A_{es}G_{es}T_{es}{}^mC_{es}{}^mC_{es}A_{es}{}^mC_{es}{}^mC_{es}G_{es}G_{es}{}^mC_{es}A_{es}A_e$ | 10.5 | 78 |
| 580043 | $T_{es}T_{es}T_{es}T_{es}{}^mC_{es}A_{es}G_{es}{}^mC_{es}T_{es}A_{es}T_{es}T_{es}T_{es}{}^mC_{es}{}^mC_{es}T_{es}G_{es}T_e$ | 13.7 | 92 |

Example 10

Effects of Uniform 2'-MOE Modified Oligonucleotides on Promoting Human HNRNPH1 Exon Skipping Several modified oligonucleotides from Table 12 were selected and further evaluated for their effect on promoting human HNRNPH1 exon 4 skipping in vitro. The 5-10-5 MOE gapmer, ISIS 172290 was included in the study for comparison.

HeLa cells were transfected using 3 µg/mL Cytofectin with 0 or 50 nM concentration of modified oligonucleotide. After a treatment period of approximately 24 hours, standard RT-PCR for HNRNPH1 RNA expression was performed using the following primers: HNRNPH1 exon 3 forward (5'-TCCAAATAGTCCTGACACGGCCAA-3' SEQ ID NO: 106) and HNRNPH1 exon 5 reverse (5'-TGGC-CATAAGCTTTCGTGGTGGAT-3' SEQ ID NO: 107). Quantification of HNRNPH1 exon 4 skipping was measured using Kodak Gel Logic imager as a ratio of exon 4 skipped transcript/total expression*100 and corrected for intensity of ethidium bromide staining. The results are presented in Table 14.

As illustrated, treatment with uniform 2'-MOE modified oligonucleotides promotes human HNRNPH1 exon 4 skipping.

TABLE 14

Effects of uniform 2'-MOE modified oligonucleotides on promoting human HNRNPH1 exon skipping

| ISIS No. | HNRNPH1 exon 4 skipping (%) |
|---|---|
| UTC | 32 |
| 580027 | 76 |
| 580038 | 62 |
| 172290 | 14 |

UTC = untreated control

Example 11

Effects of Uniform 2'-MOE Modified Oligonucleotides on Promoting Human HNRNPH1 Nonsense-Mediated Decay (NMD)

HeLa cells were transfected using 3 µg/mL Cytofectin with 0 or 50 nM concentration of modified oligonucleotide. After a treatment period of approximately 20 hours, cells were treated with vehicle or Emetine (10 µg/ml), a translation inhibitor, for 4 hours to inhibit the NMD pathway. RNA was then analyzed by quantitative real-time PCR and standard RT-PCR as previously described. Results are presented as percent of HNRNPH1 RNA expression, relative to untreated control levels and is denoted as "% UTC".

As illustrated, NMD inhibition by the presence of Emetine partially prevents the ability of uniform 2'-MOE modified oligonucleotides to knockdown HNRPNH1 expression as compared to vehicle treated cells. This effect is not observed for the RNase H-dependent 5-10-5 MOE gapmer, ISIS 172290 (Table 15). Further, when NMD is inhibited, the HNRNPH1 exon 4 skipped transcript is stabilized indicating that the HNRNPH1 exon 4 skipped transcript generated by modified oligonucleotide treatment is a substrate for NMD. (Table 16).

Emetine is a translation inhibitor and is commercially available.

TABLE 15

NMD inhibition partially prevents ASO-mediated knockdown of human HNRNPH1

| Modified Oligonucleotide Treatment | Treatment | % UTC |
|---|---|---|
| UTC | Vehicle | 100 |
|  | Emetine | 100 |
| ISIS 580027 | Vehicle | 19 |
|  | Emetine | 45 |
| ISIS 580038 | Vehicle | 19 |
|  | Emetine | 34 |
| ISIS 172290 | Vehicle | 2 |
| (5-10-5 MOE gapmer) | Emetine | 2 |

UTC = Untreated control

TABLE 16

NMD inhibition stabilizes human HNRNPH1 exon 4 skipped transcript

| Modified Oligonucleotide Treatment | Emetine treatment | HNRNPH1 exon 4 skipping (%) |
|---|---|---|
| UTC | Vehicle | 32 |
|  | Emetine | 54 |
| ISIS 580027 | Vehicle | 76 |
|  | Emetine | 93 |
| ISIS 580038 | Vehicle | 62 |
|  | Emetine | 88 |
| ISIS 172290 | Vehicle | 14 |
| (5-10-5 MOE gapmer) | Emetine | 10 |

UTC = Untreated control

Example 12

Evaluation of Uniform 2'-MOE Modified Oligonucleotides in Central Nervous System (CNS) Targeting Mouse STAT3—In Vivo Study A series of uniform 2'-MOE modified oligonucleotides targeting mouse STAT3 exon 6 and mouse STAT3 exon 17 were designed and tested for their effects on inhibition of mouse STAT3 in the CNS in vivo. The 5-10-5 MOE gapmers, ISIS 337332 and 383741 were included in the study as positive controls.

The modified oligonucleotides are 18 nucleosides in length, wherein each nucleoside has a 2'-MOR modification and is denoted as subscript "e" Subscript "d" indicates β-D-2'-deoxyribonucleosides. Each internucleoside linkage throughout the modified oligonucleotide are phosphorothioate internucleoside linkages (P=S) and is denoted as subscript "s". All cytosine residues throughout the modified oligonucleotides are 5-methylcytosines and are denoted as superscripts "m".

C57/BL6 mice were treated with 300 μg of 5-10-5 MOE gapmers or 500 μg of uniform 2'-MOE modified oligonucleotides by a single unilateral intracerebroventricular (ICV) bolus injection. The number of animals in each treatment group is presented below and is denoted as "n". The control group received an 8 μl ICV bolus injection of sterile PBS and consisted of 4 animals.

The animals were sacrificed at 4 weeks post-injection. The following brain and spinal cord tissues were isolated as follows: a 1 mm coronal brain section posterior to the injection site and a 3 mm section of thoracic spinal cord. Following tissue homogenization, RNA was isolated, and STAT3 RNA expression levels were determined with qRT-PCR using primer probe set RTS2381 for exon 3 (forward: 5'-GCCACGTTGGTGTTTCATAATCT-3', SEQ ID NO: 128, reverse: 5'-GATAGAGGACATTGGACTCTTGCA-3', SEQ ID NO: 129, probe: 5'-TTGGGTGAAATTGACCAG-CAATATAGCCG-3' SEQ ID NO: 130).

The results are presented in Table 18 as the average percent of STAT3 RNA levels for each treatment group in the brain and spinal cord, normalized to PBS-treated control and is denoted as "% PBS".

TABLE 17

Modified oligonucleotides targeting mouse STAT3 exon 6 and exon 17

| ISIS No. | Sequence (5' to 3') | SEQ ID No. |
|---|---|---|
| 337332 | $G_{es}A_{es}A_{es}G_{es}{}^mC_{es}{}^mC_{ds}T_{ds}T_{ds}G_{ds}{}^mC_{ds}{}^mC_{ds}A_{ds}G_{ds}{}^mC_{ds}{}^mC_{es}A_{es}T_{es}G_{es}T_e$ | 108 |
| 383741 | $G_{es}A_{es}{}^mC_{es}T_{es}{}^mC_{es}T_{ds}T_{ds}G_{ds}{}^mC_{ds}A_{ds}G_{ds}G_{ds}A_{ds}A_{ds}T_{ds}{}^mC_{es}G_{es}G_{es}{}^mC_{es}T_e$ | 109 |
| 566304 | $A_{es}G_{es}T_{es}T_{es}G_{es}A_{es}A_{es}A_{es}T_{es}{}^mC_{es}A_{es}A_{es}A_{es}G_{es}T_{es}{}^mC_{es}G_{es}T_e$ | 110 |
| 566307 | $T_{es}{}^mC_{es}T_{es}T_{es}G_{es}A_{es}G_{es}G_{es}G_{es}T_{es}T_{es}T_{es}G_{es}T_{es}A_{es}G_{es}T_e$ | 111 |
| 580769 | $A_{es}G_{es}A_{es}A_{es}G_{es}T_{es}T_{es}{}^mC_{es}A_{es}{}^mC_{es}G_{es}T_{es}T_{es}{}^mC_{es}T_{es}A_{es}T_{es}T_e$ | 112 |
| 580770 | $A_{es}G_{es}T_{es}G_{es}A_{es}A_{es}G_{es}A_{es}A_{es}G_{es}T_{es}T_{es}{}^mC_{es}A_{es}{}^mC_{es}G_{es}T_{es}T_e$ | 113 |
| 580771 | $G_{es}G_{es}{}^mC_{es}T_{es}T_{es}A_{es}G_{es}T_{es}G_{es}A_{es}A_{es}G_{es}A_{es}A_{es}G_{es}T_{es}T_{es}{}^mC_e$ | 114 |
| 580773 | $T_{es}{}^mC_{es}{}^mC_{es}A_{es}A_{es}T_{es}T_{es}G_{es}G_{es}{}^mC_{es}G_{es}G_{es}{}^mC_{es}T_{es}T_{es}A_{es}G_{es}T_e$ | 115 |
| 580774 | ${}^mC_{es}A_{es}G_{es}G_{es}T_{es}T_{es}{}^mC_{es}{}^mC_{es}A_{es}A_{es}T_{es}T_{es}G_{es}G_{es}{}^mC_{es}G_{es}G_{es}{}^mC_e$ | 116 |

TABLE 17-continued

Modified oligonucleotides targeting mouse STAT3 exon 6 and exon 17

| ISIS No. | Sequence (5' to 3') | SEQ ID No. |
|---|---|---|
| 580783 | $G_{es}T_{es}G_{es}G_{es}T_{es}G_{es}G_{es}A_{es}{}^mC_{es}G_{es}A_{es}G_{es}A_{es}A_{es}{}^mC_{es}T_{es}G_{es}{}^mC_e$ | 117 |
| 580810 | $A_{es}G_{es}T_{es}A_{es}G_{es}T_{es}T_{es}{}^mC_{es}A_{es}{}^mC_{es}A_{es}{}^mC_{es}{}^mC_{es}A_{es}G_{es}G_{es}{}^mC_{es}{}^mC_e$ | 118 |

TABLE 18

Effects of modified oligonucleotides on STAT3 RNA levels in CNS

| ASO | Target Region | n | Brain (% PBS) | Spinal Cord (% PBS) |
|---|---|---|---|---|
| PBS | — | 4 | 100 | 100 |
| ISIS 337332 | Exon 19 | 3 | 83 | 87 |
| ISIS 383741 | Exon 3 | 4 | 71 | 63 |
| ISIS 566304 | Exon 6 | 3 | 100 | 98 |
| ISIS 566307 | | 2 | 93 | 89 |
| ISIS 580769 | Exon 17 | 4 | 90 | 83 |
| ISIS 580770 | | | 91 | 88 |
| ISIS 580771 | | | 74 | 82 |
| ISIS 580773 | | | 75 | 79 |
| ISIS 580774 | | | 71 | 77 |
| ISIS 580783 | | | 83 | 82 |
| ISIS 580810 | | | 81 | 85 |

Example 13

Evaluation of Uniform 2'-MOE Modified Oligonucleotides in the CNS Targeting Mouse SOD1—In Vivo Study A series of uniform 2'-MOE modified oligonucleotides were designed targeting mouse SOD1 exon 2 and exon 3 and tested for their effects on inhibition of mouse SOD1 in the CNS in vivo. Gapmer, ISIS 333611, which targets exon 1, was included in the study as a positive control.

The modified oligonucleotides are 18 and 20 nucleosides in length, wherein each nucleoside has a 2'-MOE modification and is denoted as subscript "e". Subscript "d" indicates β-D-2'-deoxyribonucleosides. Each internucleoside linkage throughout the modified oligonucleotide are phosphorothioate internucleoside linkages (P=S) and is denoted as subscript "s". All cytosine residues throughout the modified oligonucleotides are 5-methylcytosines and are denoted as superscripts "m".

C57/BL6 mice were treated with 500 μg of 2'-MOE modified oligonucleotides by a single unilateral intracerebroventricular (ICV) bolus injection. The control group received a 7 μl ICV bolus injection of sterile PBS. Each treatment group consisted of 4 animals.

The animals were sacrificed at 4 weeks post-injection. The following brain and spinal cord tissues were isolated as follows: a 1 mm coronal brain section posterior to the injection site and a 3 mm section of thoracic spinal cord. Following tissue homogenization, RNA was isolated and assessed for SOD1 RNA expression levels using qRT-PCR.

The results below are presented as the average percent of SOD1 RNA levels for each treatment group in the brain and spinal cord, normalized to PBS-treated control and is denoted as "% PBS". The results show that uniform 2'-MOE modified oligonucleotides reduce expression of SOD1 in vivo through nonsense mediated decay.

TABLE 19

Modified oligonucleotides targeting mouse SOD1

| ISIS No. | Sequence (5' to 3') | Brain SOD1 RNA (% PBS) | Spinal Cord SOD1 RNA (% PBS) | SEQ ID No. |
|---|---|---|---|---|
| 333611 | ${}^mC_{es}{}^mC_{es}G_{es}T_{es}{}^mC_{es}G_{ds}{}^mC_{ds}{}^mC_{ds}{}^mC_{ds}T_{ds}T_{ds}{}^mC_{ds}A_{ds}G_{ds}{}^mC_{ds}A_{es}{}^mC_{es}G_{es}{}^mC_{es}A_e$ | 67 | 54 | 119 |
| 431855 | $T_{es}G_{es}{}^mC_{es}T_{es}{}^mC_{es}A_{es}{}^mC_{es}{}^mC_{es}T_{es}{}^mC_{es}T_{es}{}^mC_{es}T_{es}{}^mC_{es}A_{es}T_{es}{}^mC_{es}{}^mC_{es}G_e$ | 93 | 89 | 120 |
| 431858 | $G_{es}{}^mC_{es}A_{es}T_{es}A_{es}{}^mC_{es}A_{es}G_{es}A_{es}G_{es}{}^mC_{es}G_{es}T_{es}G_{es}{}^mC_{es}T_{es}G_{es}{}^mC_{es}T_{es}{}^mC_e$ | 89 | 72 | 121 |
| 575567 | $G_{es}T_{es}{}^mC_{es}{}^mC_{es}T_{es}G_{es}A_{es}{}^mC_{es}A_{es}A_{es}{}^mC_{es}A_{es}{}^mC_{es}A_{es}A_{es}{}^mC_{es}T_{es}G_e$ | 83 | 68 | 122 |
| 575581 | $G_{es}G_{es}A_{es}{}^mC_{es}G_{es}T_{es}G_{es}G_{es}A_{es}A_{es}{}^mC_{es}{}^mC_{es}{}^mC_{es}A_{es}T_{es}G_{es}{}^mC_{es}T_e$ | 63 | 55 | 123 |
| 575641 | $A_{es}G_{es}G_{es}A_{es}T_{es}T_{es}A_{es}A_{es}A_{es}A_{es}T_{es}G_{es}A_{es}G_{es}G_{es}T_{es}{}^mC_{es}{}^mC_e$ | 91 | 69 | 124 |
| 575644 | ${}^mC_{es}T_{es}T_{es}A_{es}G_{es}A_{es}G_{es}T_{es}G_{es}A_{es}G_{es}G_{es}A_{es}T_{es}T_{es}A_{es}A_{es}A_e$ | 75 | 53 | 125 |

TABLE 19-continued

Modified oligonucleotides targeting mouse SOD1

| ISIS No. | Sequence (5' to 3') | Brain SOD1 RNA (% PBS) | Spinal Cord SOD1 RNA (% PBS) | SEQ ID No. |
|---|---|---|---|---|
| 575645 | $T_{es}T_{es}T_{es}{}^{m}C_{es}T_{es}T_{es}A_{es}G_{es}A_{es}G_{es}T_{es}G_{es}$ $A_{es}G_{es}G_{es}A_{es}T_{es}T_{e}$ | 73 | 55 | 126 |
| 575647 | $A_{es}{}^{m}C_{es}{}^{m}C_{es}A_{es}T_{es}G_{es}T_{es}T_{es}T_{es}{}^{m}C_{es}T_{es}T_{es}$ $A_{es}G_{es}A_{es}G_{es}T_{es}G_{e}$ | 74 | 54 | 127 |

Example 14

Effects of Uniform 2'-MOE Modified Oligonucleotides on Promoting Human STAT3 Double Exon Skipping ISIS 580073 and 580076 from Table 1, which target human STAT3 exon 6, were selected and further evaluated for their effects on human STAT3 exon expression in vitro. The 5-10-5 MOE gapmer, ISIS 455291 was included in the study as a positive control for STAT3 knockdown.

HeLa cells were transfected using 3 μg/mL Cytofectin with 0 or 50 nM modified oligonucleotide as specified in the table below. After a treatment period of approximately 24 hours, RNA was isolated from the cells and the STAT3 RNA was analyzed by RT-PCR using the following primers: STAT3 exon 3 forward (5'-AGTATAGCCGCTTCCTG-CAAGAGT-3' SEQ ID NO: 172) and STAT3 exon 9 reverse (5'-CGGGTCTGAAGTTGAGATTCTGCT-3' SEQ ID NO:173). In order to visualize low abundance PCR products, 26 PCR cycles were performed followed by separation of the PCR products on an ethidium bromide stained polyacrylamide gel. The identities of the resulting bands were determined by sequencing (Retrogen, San Diego, Calif.). Both the single skipped (Δexon 6) and the double skipped (Δexons 5 & 6) sequences contained premature stop codons. Quantification of single and double exon skipping was done using Kodak Gel Logic imager, and the ratios of Δexon 6 RNA/total STAT3 RNA and Δexons 5 & 6 RNA/total STAT3 RNA were calculated and multiplied by 100 to determine the % exon skipping reported in Table 20 below. The results in Table 20 are the average values from three replicate experiments.

TABLE 20

Effects of modified oligonucleotides on human STAT3 exon skipping

| ISIS No. | % STAT3 Δexon 6 | % STAT3 Δexon 5/ Δexon 6 | SEQ ID NO. |
|---|---|---|---|
| UTC | 4 | 2 | |
| 580073 | 43 | 15 | 22 |
| 580076 | 35 | 3 | 25 |
| 455291 | 3 | 3 | 4 |

Example 15

Effects of Uniform 2'-MOE Modified Oligonucleotides on Mouse SOD1

ISIS 575581 and 575644 from Table 19, which target exon 2 and exon 3 of SOD1, respectively, were evaluated for their effects on inhibiting mouse SOD1 expression in vitro. The 5-10-5 MOE gapmer, ISIS 333611 (see Table 19), was included in the study as a positive control for SOD1 knockdown.

Mouse bEND cells were transfected using 3 μg/mL Cytofectin with 0, 3.125, 6.25, 12.5, 25, or 50 nM modified oligonucleotide as specified in Table 21 below. After a treatment period of approximately 24 hours, RNA was isolated from the cells and the RNA levels of SOD1 were measured by quantitative real-time PCR. Mouse SOD1 primer probe set for exon 1 (forward sequence 5'-TTTTTT-GCGCGGTCCTTTC-3', SEQ ID NO: 131; reverse sequence 5'-GAGGGACCAGAGAGAGCAAGAC-3', SEQ ID NO: 132; probe sequence 5'-CGCCTTCCGTCCGTCG-GCT-3', SEQ ID NO: 133) was used to measure RNA levels. Mouse SOD1 RNA levels were normalized to total RNA content, as measured by RIBOGREEN®. Results are presented below as percent SOD1 RNA level relative to the SOD1 RNA level in the untreated control cells, denoted as "% UTC".

TABLE 21

Effects of modified oligonucleotides on mouse SOD1 RNA expression

| ISIS No. | Concentration (nM) | % UTC | SEQ ID No. |
|---|---|---|---|
| 575581 | 3.125 | 75 | 123 |
| | 6.25 | 35 | |
| | 12.5 | 24 | |
| | 25 | 21 | |
| | 50 | 24 | |
| 575644 | 3.125 | 40 | 125 |
| | 6.25 | 21 | |
| | 12.5 | 21 | |
| | 25 | 13 | |
| | 50 | 17 | |
| 333611 | 3.125 | 21 | 119 |
| | 6.25 | 9 | |
| | 12.5 | 6 | |
| | 25 | 6 | |
| | 50 | 6 | |

ISIS 575581 and 575644 were also evaluated for their effects on full-length human SOD1 protein expression levels. The 5-10-5 MOE gapmer, ISIS 333611 was included as a positive control.

HeLa cells were transfected using 3 μg/mL Cytofectin with 0, 3.125, 12.5, or 50 nM modified oligonucleotide as specified in Table 22 below. After a treatment period of approximately 48 hours, protein was isolated from the cells and protein levels of full-length SOD1 were measured by Western blot.

For the Western blot, 15 μg of protein lysate was loaded onto 4-12% Bis-Tris gels and following transfer, the membrane with incubated with primary SOD1 antibody (ab16831, Abcam) at 1:2000 dilution overnight at 4° C. Following washing, the membrane was incubated with anti-rabbit secondary antibody sc-2030, Santa Cruz Biotechnology) at 1:2500 dilution for 1 hour at room temperature. α-tubulin served as a loading control (Sigma-Aldrich). Results in Table 22 are presented as percent of full-length SOD1 protein expression, relative to untreated control levels and is denoted as "% UTC."

TABLE 22

Effects of modified oligonucleotides on full-length mouse SOD1 protein expression

| ISIS No. | Conc (nM) | % UTC | SEQ ID No. |
|---|---|---|---|
| 575581 | 3.125 | 26 | 123 |
|  | 12.5 | 3 |  |
|  | 50 | 4 |  |
| 575644 | 3.125 | 18 | 125 |
|  | 12.5 | 3 |  |
|  | 50 | 9 |  |
| 333611 | 3.125 | 2 | 119 |
|  | 12.5 | 4 |  |
|  | 50 | 6 |  |

Example 16

Effects of Uniform 2'-MOE Modified Oligonucleotides on Promoting Mouse SOD1 Double Exon Skipping ISIS 575581 and 575644, which target mouse SOD1 exon 2 and exon 3, respectively, were evaluated for their effects on mouse SOD1 exon 2 and 3 expression in vitro. The 5-10-5 MOE gapmer, ISIS 333611 was included in the study as a positive control for SOD1 knockdown.

Mouse bEND cells were transfected using 3 µg/mL Cytofectin with 0 or 50 nM modified oligonucleotide as specified in the table below. After a treatment period of approximately 24 hours, RNA was isolated from the cells and the SOD1 RNA was analyzed by RT-PCR using the following primers: SOD1 exon 1 forward (5'-TGCAGGGAACCATCCACT-TCGA-3' SEQ ID NO: 134) and SOD1 exon 4 reverse (5'-ACCGTCCTTTCCAGCAGTCACA-3' SEQ ID NO: 135). In order to visualize low abundance PCR products, 26 PCR cycles were performed followed by separation of the PCR products on an ethidium bromide stained polyacrylamide gel. The identities of the resulting bands were determined by sequencing (Retrogen, San Diego, Calif.). Both the single skipped (Δexon 2 and Δexon 3) and the double skipped (Δexons 2 & 3) sequences contained premature stop codons. Quantification of single and double exon skipping was done using Kodak Gel Logic imager, and the ratios of Δexon 2 RNA/total SOD1 RNA, Δexon 3 RNA/total SOD1 RNA, and Δexons 2 & 3 RNA/total SOD1 RNA were calculated and multiplied by 100 to determine the % exon skipping reported in Table 23 below. The results in Table 23 are the average values from three replicate experiments.

TABLE 23

Effects of modified oligonucleotides on mouse SOD1 exon skipping

| ISIS No. | % SOD1 Δexon 2 | % SOD1 Δexon 3 | % SOD1 Δexon 2/ Δexon 3 | SEQ ID NO. |
|---|---|---|---|---|
| UTC | 1 | 1 | 1 |  |
| 575581 | 34 | 1 | 30 | 123 |

TABLE 23-continued

Effects of modified oligonucleotides on mouse SOD1 exon skipping

| ISIS No. | % SOD1 Δexon 2 | % SOD1 Δexon 3 | % SOD1 Δexon 2/ Δexon 3 | SEQ ID NO. |
|---|---|---|---|---|
| 575644 | 2 | 31 | 3 | 125 |
| 333611 | 3 | 3 | 4 | 119 |

Example 17

Effects of Uniform 2'-MOE Modified Oligonucleotides on Human STAT3 Pre-mRNA and mRNA ISIS 580073 and 580076 from Table 1, which target human STAT3 exon 6, were evaluated for their effects on human STAT3 pre-mRNA and mRNA expression in vitro. The 5-10-5 MOE gapmer, ISIS 337247, $T_{es} T_{es} T_{es} T_{es} G_{es} {}^mC_{ds} A_{ds} T_{ds} G_{ds} A_{ds} T_{ds} G_{ds} T_{ds} A_{ds} A_{ds} {}^mC_{es} {}^mC_{es} A_{es} {}^mC_{es} T_e$, (SEQ ID NO: 136) was included in the study as a positive control for STAT3 knockdown.

HeLa cells were transfected using 3 µg/mL Cytofectin with 0, 3.125, 6.25, 12.5, 25, or 50 nM modified oligonucleotide as specified in the table below. After a treatment period of approximately 24 hours, RNA was isolated from the cells and the STAT3 RNA was analyzed by qRT-PCR using the RTS199 primer probe set for exon 3 (see Example 1), hSTAT3_EXON8_LTS01120 primer probe set for exon 8 (see Example 4), and RTS3235 primer probe set for exons 22 and 23 (see Example 4). STAT3 pre-mRNA was analyzed by qRT-PCR using a primer probe set for intron 3: forward (5'-GCAGAGTCGGGTGTTAGTGTTCT-3' SEQ ID NO: 137), reverse (5'-GCTCACGGGTAAGTATACAGAGCTT-3' SEQ ID NO: 138), probe (5'-TCCTG-GAAGCATCTCTTTTCTCATTTGGC-3' SEQ ID NO: 139); a primer probe set for intron 21: forward (5'-TGCA-GTGCCTTCTTTCACATG-3' SEQ ID NO: 140), reverse (5'-GGGTGAGGTGGGCTGAGA-3' SEQ ID NO: 141), probe (5'-CATCATGCTCTCTGATCCCTCAGGTTCTGT-3' SEQ ID NO: 142); and a primer probe set for intron 23 and exon 24: forward (5'-GCAGAGGGTGGACAACTGAAC-3' SEQ ID NO: 143), reverse (5'-GAGGTCAACTCCAT-GTCAAAGGT-3' SEQ ID NO: 144), probe (5'-AGTTTTC-CCTGTCTGTCCCTCCAGAGTCC-3' SEQ ID NO: 145). Human STAT3 RNA and pre-mRNA levels were normalized to total RNA content, as measured by RIBOGREEN®.

Results are presented in Table 24 as percent STAT3 RNA or pre-mRNA level relative to the STAT3 RNA or pre-mRNA level in the untreated control cells, denoted as "% UTC". The results show that STAT3 RNA levels decreased in a dose dependent manner, whereas STAT3 pre-mRNA levels were largely unaffected by uniform 2'-MOE oligonucleotides. These results are consistent with a nonsense mediated decay mechanism of target knockdown, which occurs after splicing.

Exon 6 skipping was also analyzed as described in Example 5, and the results are shown in Table 25.

TABLE 24

Effects of modified oligonucleotides on STAT3 pre-mRNA versus RNA

| Concentration (nM) | Exon 3 (% UTC) | Exon 8 (% UTC) | Exon 22/Exon 23 (% UTC) | Intron 3 (% UTC) | Intron 21 (% UTC) | Intron 23/Exon 24 (% UTC) |
|---|---|---|---|---|---|---|
| ISIS No. 580073, SEQ ID NO: | | | | | | |
| 3.125 | 55 | 60 | 53 | 122 | 135 | 146 |
| 6.25 | 40 | 38 | 37 | 95 | 108 | 125 |
| 12.5 | 29 | 25 | 27 | 95 | 106 | 114 |
| 25 | 22 | 21 | 21 | 87 | 93 | 103 |
| 50 | 19 | 18 | 20 | 85 | 88 | 92 |
| ISIS No. 580076, SEQ ID NO: | | | | | | |
| 3.125 | 75 | 67 | 69 | 84 | 110 | 93 |
| 6.25 | 60 | 57 | 57 | 93 | 88 | 110 |
| 12.5 | 43 | 40 | 47 | 92 | 101 | 107 |
| 25 | 26 | 20 | 26 | 87 | 94 | 98 |
| 50 | 22 | 23 | 30 | 92 | 100 | 98 |
| ISIS No. 337247, SEQ ID NO: | | | | | | |
| 3.125 | 67 | 70 | 65 | 93 | 93 | 101 |
| 6.25 | 47 | 50 | 48 | 44 | 46 | 70 |
| 12.5 | 25 | 18 | 26 | 34 | 40 | 57 |
| 25 | 15 | 11 | 19 | 27 | 30 | 45 |
| 50 | 9 | 10 | 15 | 32 | 30 | 48 |

TABLE 25

STAT3 exon 6 skipping

| Concentration (nM) | Exon 6 skipping (%) |
|---|---|
| ISIS No. 580073, SEQ ID NO: | |
| UTC | 0 |
| 3.125 | 100 |
| 6.25 | 251 |
| 12.5 | 359 |
| 25 | 492 |
| 50 | 434 |
| ISIS No. 580076, SEQ ID NO: | |
| UTC | 0 |
| 3.125 | 21 |
| 6.25 | 64 |
| 12.5 | 178 |
| 25 | 264 |
| 50 | 318 |
| ISIS No. 337247, SEQ ID NO: | |
| UTC | 0 |
| 3.125 | 0 |
| 6.25 | 0 |
| 12.5 | 0 |
| 25 | 0 |
| 50 | 0 |

Example 18

Effects of Uniform 2'-MOE Modified Oligonucleotides on Promoting Human STAT3 Nonsense-Mediated Decay (NMD)

ISIS 580073 and 580076 were evaluated for their effects on nonsense-mediated decay of human STAT3. The 5-10-5 MOE gapmer ISIS 455291, which does not work through NMD, was included as a negative control.

HeLa cells were transfected using 3 μg/mL Cytofectin with 0 or 50 nM modified oligonucleotide. After a treatment period of approximately 20 hours, cells were treated with vehicle or Emetine (10 μg/ml), a translation inhibitor, for 4 hours to inhibit the NMD pathway. Cells were then harvested and RNA was isolated and analyzed. Exon 6 skipping was analyzed as described in Example 5, and the results are presented in Table 26. Total STAT3 RNA was analyzed by qRT-PCR using primer probe set RTS199 (see Example 1). Results are presented in Table 27 as percent of STAT3 RNA expression relative to untreated control cells, denoted as "% UTC".

As illustrated in Table 27, NMD inhibition by Emetine partially prevents the ability of uniform 2'-MOE modified oligonucleotides to knock down STAT3 expression as compared to vehicle treated cells. This effect is not observed for the RNase H-dependent 5-10-5 MOE gapmer, ISIS 455291. Further, the STAT3 exon 6 skipped transcript is stabilized when NMD is inhibited (Table 26), consistent with the NMD mechanism for knock-down in which the STAT3 exon 6 skipped transcript generated by modified oligonucleotide treatment is a substrate for NMD.

TABLE 26

Stabilization of human STAT3 exon 6 skipped transcript following Emetine treatment

| ISIS No. | Emetine treatment | STAT3 exon 6 skipping (%) |
|---|---|---|
| n/a, untreated control cells | Vehicle | 9 |
| | Emetine | 4 |
| 580073 | Vehicle | 66 |
| | Emetine | 97 |
| 580076 | Vehicle | 63 |
| | Emetine | 88 |
| 455291 | Vehicle | 18 |
| | Emetine | 18 |

TABLE 27

Partial prevention of human STAT3 knock-down by uniform 2'-MOE oligonucleotides following Emetine treatment

| ISIS No. | Treatment | % UTC |
|---|---|---|
| 580073 | Vehicle | 7 |
| | Emetine | 32 |

TABLE 27-continued

Partial prevention of human STAT3 knock-down by uniform 2'-MOE oligonucleotides following Emetine treatment

| ISIS No. | Treatment | % UTC |
|---|---|---|
| 580076 | Vehicle | 10 |
|  | Emetine | 47 |
| 455291 | Vehicle | 8 |
|  | Emetine | 10 |

Example 19

Effects of Uniform 2'-MOE Modified Oligonucleotides on Promoting Mouse SOD1 Nonsense-Mediated Decay (NMD)

ISIS 575581 and 575644, which target mouse SOD1 exon 2 and exon 3, respectively, were evaluated for their effects on nonsense-mediated decay of mouse SOD1. The 5-10-5 MOE gapmer ISIS 333611, which does not work through NMD, was included as a negative control.

Mouse bEND cells were transfected using 3 µg/mL Cytofectin with 0 or 50 nM modified oligonucleotide. After a treatment period of approximately 20 hours, cells were treated with vehicle or Emetine (10 µg/ml), a translation inhibitor, for 4 hours to inhibit the NMD pathway. Cells were then harvested and RNA was isolated. SOD1 RNA was analyzed by RT-PCR using the following primers: SOD1 exon 1 forward (5'-TGCAGGGAACCATCCACTTCGA-3' SEQ ID NO: 134) and SOD1 exon 4 reverse (5'-ACCGTC-CTTTCCAGCAGTCACA-3' SEQ ID NO: 135). 25 PCR cycles were performed followed by separation of the PCR products on an ethidium bromide stained polyacrylamide gel. Quantification of exon 2 skipping and exon 3 skipping was done using Kodak Gel Logic imager, and the ratios of Aexon 2 RNA/total SOD1 RNA and Aexon 3 RNA/total SOD1 RNA were calculated and multiplied by 100 and corrected for intensity of ethidium bromide staining. The results are presented as % exon skipping in Table 28 below. Total SOD1 RNA was analyzed by qRT-PCR using mouse SOD1 primer probe set for exon 1 (forward sequence 5'-TTTTTTGCGCGGTCCTTTC-3', SEQ ID NO: 131; reverse sequence 5'-GAGGGACCAGAGAGAGCAAGAC-3', SEQ ID NO: 132; probe sequence 5'-CGCCTTCCGTC-CGTCGGCT-3', SEQ ID NO: 133). Results are presented in Table 29 as percent of SOD1 RNA expression relative to untreated control cells, denoted as "% UTC".

As illustrated in Table 29, NMD inhibition by Emetine partially prevents the ability of uniform 2'-MOE modified oligonucleotides to knock down SOD1 expression as compared to vehicle treated cells. This effect is not observed for the RNase H-dependent 5-10-5 MOE gapmer, ISIS 333611. Further, the SOD1 exon 2 skipped and exon 3 skipped transcripts are stabilized when NMD is inhibited (Table 28), consistent with the NMD mechanism for knock-down in which the SOD1 exon 2 skipped and exon 3 skipped transcripts generated by modified oligonucleotide treatment are substrates for NMD.

TABLE 28

Stabilization of mouse SOD1 exon skipped transcripts following Emetine treatment

| ISIS No. | Emetine treatment | SOD1 exon 2 skipping (%) | SOD1 exon 3 skipping (%) |
|---|---|---|---|
| n/a, untreated control cells | Vehicle | 2 | 0 |
|  | Emetine | 2 | 2 |
| 575581 | Vehicle | 67 | 6 |
|  | Emetine | 83 | 2 |
| 575644 | Vehicle | 5 | 65 |
|  | Emetine | 2 | 77 |
| 333611 | Vehicle | 7 | 6 |
|  | Emetine | 7 | 3 |

TABLE 29

Partial prevention of mouse SOD1 knock-down by uniform 2'-MOE oligonucleotides following Emetine treatment

| ISIS No. | Treatment | % UTC |
|---|---|---|
| 575581 | Vehicle | 25 |
|  | Emetine | 33 |
| 575644 | Vehicle | 13 |
|  | Emetine | 22 |
| 333611 | Vehicle | 2 |
|  | Emetine | 3 |

Example 20

Effects of Non-Uniformly Modified Oligonucleotides on Human STAT3, Mouse SOD1, and Human HNRNPH1 Expression The modified oligonucleotides listed in Tables 30-32 below were evaluated for their effects on human STAT3, mouse SOD1, and human HNRNPH1 expression in vitro. Gapmers, which act via RNase H, were included as positive controls.

HeLa cells (for human STAT3 and HNRNPH1 studies) or bEND cells (for mouse SOD1 studies) were transfected using 3 µg/mL Cytofectin with 0, 0.78, 3.125, 12.5, or 50 nM modified oligonucleotide as specified in the table below. After a treatment period of approximately 24 hours, RNA was isolated from the cells, and RNA was analyzed by qRT-PCR using primer probe set RTS199 (see Example 1) for STAT3, primer probe set HTS3648 (see Example 8) for HNRNPH1, and primer probe set for exon 1 (see Example 15) for SOD1.

The half maximal inhibitory concentration ($IC_{50}$) of each oligonucleotide is presented in the table below and was calculated by plotting the concentrations of oligonucleotides used versus the percent inhibition of RNA expression achieved at each concentration, and noting the concentration of oligonucleotide at which 50% inhibition of human STAT3 RNA expression was achieved compared to the control. Results are presented in Tables 30-32 below. "ND" indicates that the $IC_{50}$ was not determined because the oligonucleotide failed to achieve at least 50% inhibition at any concentration tested.

In the tables below, Subscript "e" indicates 2'-MOE modified nucleoside, subscript "d" indicates β-D-2'-deoxyribonucleoside, subscript "s" indicates phosphorothioate internucleoside linkage, superscript "m" indicates 5-methylcytosine, and subscript "m" indicates 2'-O methyl nucleoside.

TABLE 30

Effects of non-uniformly modified oligonucleotides on human STAT3 expression

| ISIS No. | Sequence 5' to 3' | Motif | IC$_{50}$ (nM) | SEQ ID No. |
|---|---|---|---|---|
| 580073, Parent | A$_{es}$ T$_{es}$ $^m$C$_{es}$ A$_{es}$ A$_{es}$ A$_{es}$ G$_{es}$ T$_{es}$ $^m$C$_{es}$ A$_{es}$ T$_{es}$ $^m$C$_{es}$ $^m$C$_{es}$ T$_{es}$ G$_{es}$ G$_{es}$ A$_{es}$ G$_e$ | Uniform 2'-MOE | 7.3 | 22 |
| 337278 | A$_{es}$ A$_{es}$ T$_{es}$ $^m$C$_{es}$ A$_{ds}$ A$_{ds}$ G$_{ds}$ T$_{ds}$ $^m$C$_{ds}$ A$_{ds}$ T$_{ds}$ $^m$C$_{ds}$ $^m$C$_{ds}$ T$_{ds}$ G$_{es}$ G$_{es}$ A$_{es}$ G$_{es}$ A$_e$ | Gapmer | 6.1 | 146 |
| 671130 | A$_{ms}$ U$_{ms}$ C$_{ms}$ A$_{ms}$ A$_{ms}$ A$_{ms}$ G$_{ms}$ U$_{ms}$ C$_{ms}$ A$_{ms}$ U$_{ms}$ C$_{ms}$ C$_{ms}$ U$_{ms}$ G$_{ms}$ G$_{ms}$ A$_{ms}$ G$_m$ | Uniform 2'-OMe | 42.5 | 147 |
| 670708 | A$_{ks}$ T$_{ks}$ $^m$C$_{ds}$ A$_{ds}$ A$_{ks}$ A$_{ds}$ G$_{ds}$ T$_{ks}$ $^m$C$_{ds}$ A$_{ds}$ T$_{ks}$ $^m$C$_{ds}$ $^m$C$_{ds}$ T$_{ks}$ G$_{ds}$ G$_{ds}$ A$_{ks}$ G$_k$ | cEt/DNA | 5.2 | 22 |
| 670703 | $^m$C$_{ks}$ A$_{ds}$ A$_{ds}$ A$_{ks}$ G$_{ds}$ T$_{ds}$ $^m$C$_{ks}$ A$_{ds}$ T$_{ds}$ $^m$C$_{ks}$ $^m$C$_{ds}$ T$_{ds}$ G$_{ks}$ G$_{ds}$ A$_{ds}$ G$_k$ | cEt/DNA | 6.1 | 148 |
| 670705 | A$_{ks}$ T$_{ds}$ $^m$C$_{ds}$ A$_{ks}$ A$_{ds}$ A$_{ds}$ G$_{ks}$ T$_{ds}$ $^m$C$_{ds}$ A$_{ks}$ T$_{ds}$ $^m$C$_{ds}$ $^m$C$_{ks}$ T$_{ds}$ G$_{ds}$ G$_k$ | cEt/DNA | 17.1 | 149 |
| 670709 | A$_{ks}$ T$_{ks}$ $^m$C$_{es}$ A$_{es}$ A$_{ks}$ A$_{es}$ G$_{es}$ T$_{ks}$ $^m$C$_{es}$ A$_{es}$ T$_{ks}$ $^m$C$_{es}$ $^m$C$_{es}$ T$_{ks}$ G$_{es}$ G$_{es}$ A$_{ks}$ G$_k$ | cEt/2'-MOE | 12.0 | 22 |
| 670704 | $^m$C$_{ks}$ A$_{es}$ A$_{es}$ A$_{ks}$ G$_{es}$ T$_{es}$ $^m$C$_{ks}$ A$_{es}$ T$_{es}$ $^m$C$_{ks}$ $^m$C$_{es}$ T$_{es}$ G$_{ks}$ G$_{es}$ A$_{es}$ G$_k$ | cEt/2'-MOE | 10.2 | 148 |
| 670706 | A$_{ks}$ T$_{es}$ $^m$C$_{es}$ A$_{ks}$ A$_{es}$ A$_{es}$ G$_{ks}$ T$_{es}$ $^m$C$_{es}$ A$_{ks}$ T$_{es}$ $^m$C$_{es}$ $^m$C$_{ks}$ T$_{es}$ G$_{es}$ G$_k$ | eEt/2'-MOE | 10.0 | 149 |
| 580076, Parent | A$_{es}$ T$_{es}$ A$_{es}$ G$_{es}$ T$_{es}$ T$_{es}$ G$_{es}$ A$_{es}$ A$_{es}$ A$_{es}$ T$_{es}$ $^m$C$_{es}$ A$_{es}$ A$_{es}$ A$_{es}$ G$_{es}$ T$_{es}$ $^m$C$_e$ | Uniform 2'-MOE | 15.5 | 25 |
| 670717 | T$_{es}$ A$_{es}$ T$_{es}$ A$_{es}$ G$_{es}$ T$_{ds}$ T$_{ds}$ G$_{ds}$ A$_{ds}$ A$_{ds}$ A$_{ds}$ T$_{ds}$ $^m$C$_{ds}$ A$_{ds}$ A$_{ds}$ A$_{es}$ G$_{es}$ T$_{es}$ $^m$C$_{es}$ A$_e$ | Gapmer | 14.4 | 150 |
| 671131 | A$_{ms}$ U$_{ms}$ A$_{ms}$ G$_{ms}$ U$_{ms}$ U$_{ms}$ G$_{ms}$ A$_{ms}$ A$_{ms}$ A$_{ms}$ U$_{ms}$ C$_{ms}$ A$_{ms}$ A$_{ms}$ A$_{ms}$ G$_{ms}$ U$_{ms}$ C$_m$ | Uniform 2'-OMe | ND | 151 |
| 670715 | A$_{ks}$ T$_{ks}$ A$_{ds}$ G$_{ds}$ T$_{ks}$ T$_{ds}$ G$_{ds}$ A$_{ks}$ A$_{ds}$ A$_{ds}$ T$_{ks}$ $^m$C$_{ds}$ A$_{ds}$ A$_{ks}$ A$_{ds}$ G$_{ds}$ T$_{ks}$ $^m$C$_k$ | cEt/DNA | 25.8 | 25 |
| 670710 | A$_{ks}$ G$_{ds}$ T$_{ds}$ T$_{ks}$ G$_{ds}$ A$_{ds}$ A$_{ks}$ A$_{ds}$ T$_{ds}$ $^m$C$_{ks}$ A$_{ds}$ A$_{ds}$ A$_{ks}$ G$_{ds}$ T$_{ds}$ $^m$C$_k$ | cEt/DNA | 22.0 | 152 |
| 670711 | A$_{ks}$ T$_{ds}$ A$_{ds}$ G$_{ks}$ T$_{ds}$ T$_{ds}$ G$_{ks}$ A$_{ds}$ A$_{ds}$ A$_{ks}$ T$_{ds}$ $^m$C$_{ds}$ A$_{ks}$ A$_{ds}$ A$_{ds}$ G$_k$ | cEt/DNA | ND | 153 |
| 670716 | A$_{ks}$ T$_{ks}$ A$_{es}$ G$_{es}$ T$_{ks}$ T$_{es}$ G$_{es}$ A$_{ks}$ A$_{es}$ A$_{es}$ T$_{ks}$ $^m$C$_{es}$ A$_{es}$ A$_{ks}$ A$_{es}$ G$_{es}$ T$_{ks}$ $^m$C$_k$ | cEt/2'-MOE | 3.5 | 25 |
| 670712 | A$_{ks}$ G$_{es}$ T$_{es}$ T$_{ks}$ G$_{es}$ A$_{es}$ A$_{ks}$ A$_{es}$ T$_{es}$ $^m$C$_{ks}$ A$_{es}$ A$_{es}$ A$_{ks}$ G$_{es}$ T$_{es}$ $^m$C$_k$ | cEt/2'-MOE | 2.4 | 152 |
| 670713 | A$_{ks}$ T$_{es}$ A$_{es}$ G$_{ks}$ T$_{es}$ T$_{es}$ G$_{ks}$ A$_{es}$ A$_{es}$ A$_{ks}$ T$_{es}$ $^m$C$_{es}$ A$_{ks}$ A$_{es}$ A$_{es}$ G$_k$ | cEt/2'-MOE | 5.8 | 153 |

TABLE 31

Effects of non-uniformly modified oligonucleotides on mouse SOD1 expression

| ISIS No. | Sequence 5' to 3' | Motif | IC$_{50}$ (nM) | SEQ ID No. |
|---|---|---|---|---|
| 575581, Parent | G$_{es}$ G$_{es}$ A$_{es}$ $^m$C$_{es}$ G$_{es}$ T$_{es}$ G$_{es}$ G$_{es}$ A$_{es}$ A$_{es}$ $^m$C$_{es}$ $^m$C$_{es}$ $^m$C$_{es}$ A$_{es}$ T$_{es}$ G$_{es}$ $^m$C$_{es}$ T$_e$ | Uniform 2'-MOE | 9.9 | 123 |
| 670741 | T$_{es}$ G$_{es}$ G$_{es}$ A$_{es}$ $^m$C$_{es}$ G$_{ds}$ T$_{ds}$ G$_{ds}$ G$_{ds}$ A$_{ds}$ A$_{ds}$ $^m$C$_{ds}$ $^m$C$_{ds}$ $^m$C$_{ds}$ A$_{ds}$ T$_{es}$ G$_{es}$ $^m$C$_{es}$ T$_{es}$ G$_e$ | Gapmer | 0.7 | 154 |

TABLE 31-continued

Effects of non-uniformly modified oligonucleotides on mouse SOD1 expression

| ISIS No. | Sequence 5' to 3' | Motif | IC$_{50}$ (nM) | SEQ ID No. |
|---|---|---|---|---|
| 671134 | G$_{ms}$ G$_{ms}$ A$_{ms}$ C$_{ms}$ G$_{ms}$ U$_{ms}$ G$_{ms}$ G$_{ms}$ A$_{ms}$ A$_{ms}$ C$_{ms}$ C$_{ms}$ C$_{ms}$ A$_{ms}$ U$_{ms}$ G$_{ms}$ C$_{ms}$ U$_{m}$ | Uniform 2'-OMe | 14.2 | 155 |
| 670739 | G$_{ks}$ G$_{ks}$ A$_{ds}$ $^m$C$_{ds}$ G$_{ks}$ T$_{ds}$ G$_{ds}$ G$_{ks}$ A$_{ds}$ A$_{ds}$ $^m$C$_{ks}$ $^m$C$_{ds}$ $^m$C$_{ds}$ A$_{ks}$ T$_{ds}$ G$_{ds}$ $^m$C$_{ks}$ T$_{k}$ | cEt/DNA | 4.5 | 123 |
| 670734 | A$_{ks}$ $^m$C$_{ds}$ G$_{ds}$ T$_{ds}$ G$_{ds}$ G$_{ds}$ A$_{ks}$ A$_{ds}$ $^m$C$_{ds}$ $^m$C$_{ks}$ $^m$C$_{ds}$ A$_{ds}$ T$_{ks}$ G$_{ds}$ $^m$C$_{ds}$ T$_{k}$ | cEt/DNA | 14.3 | 156 |
| 670735 | G$_{ks}$ G$_{ds}$ A$_{ds}$ $^m$C$_{ks}$ G$_{ds}$ T$_{ds}$ G$_{ks}$ G$_{ds}$ A$_{ds}$ A$_{ks}$ $^m$C$_{ds}$ $^m$C$_{ds}$ $^m$C$_{ks}$ A$_{ds}$ T$_{ds}$ G$_{k}$ | cEt/DNA | 4.8 | 157 |
| 670740 | G$_{ks}$ G$_{ks}$ A$_{es}$ $^m$C$_{es}$ G$_{ks}$ T$_{es}$ G$_{es}$ G$_{ks}$ A$_{es}$ A$_{es}$ $^m$C$_{ks}$ $^m$C$_{es}$ $^m$C$_{es}$ A$_{ks}$ T$_{es}$ G$_{es}$ $^m$C$_{ks}$ T$_{k}$ | cEt/2'-MOE | 37.1 | 123 |
| 670736 | A$_{ks}$ $^m$C$_{es}$ G$_{es}$ T$_{es}$ G$_{es}$ G$_{es}$ A$_{ks}$ A$_{es}$ $^m$C$_{es}$ $^m$C$_{ks}$ $^m$C$_{es}$ A$_{es}$ T$_{ks}$ G$_{es}$ $^m$C$_{es}$ T$_{k}$ | cEt/2'-MOE | ND | 156 |
| 670737 | G$_{ks}$ G$_{es}$ A$_{es}$ $^m$C$_{ks}$ G$_{es}$ T$_{es}$ G$_{ks}$ G$_{es}$ A$_{es}$ A$_{ks}$ $^m$C$_{es}$ $^m$C$_{es}$ $^m$C$_{ks}$ A$_{es}$ T$_{es}$ G$_{k}$ | cEt/2'-MOE | 19.6 | 157 |
| 575644, Parent | $^m$C$_{es}$ T$_{es}$ T$_{es}$ A$_{es}$ G$_{es}$ A$_{es}$ G$_{es}$ T$_{es}$ G$_{es}$ A$_{es}$ G$_{es}$ G$_{es}$ A$_{es}$ T$_{es}$ T$_{es}$ A$_{es}$ A$_{es}$ A$_{e}$ | Uniform 2'-MOE | 6.8 | 125 |
| 670749 | T$_{es}$ $^m$C$_{es}$ T$_{es}$ T$_{es}$ A$_{es}$ G$_{ds}$ A$_{ds}$ G$_{ds}$ T$_{ds}$ G$_{ds}$ A$_{ds}$ G$_{ds}$ G$_{ds}$ A$_{ds}$ T$_{ds}$ T$_{es}$ A$_{es}$ A$_{es}$ A$_{es}$ A$_{e}$ | Gapmer | 4.3 | 158 |
| 671135 | C$_{ms}$ U$_{ms}$ U$_{ms}$ A$_{ms}$ G$_{ms}$ A$_{ms}$ G$_{ms}$ U$_{ms}$ G$_{ms}$ A$_{ms}$ G$_{ms}$ G$_{ms}$ A$_{ms}$ U$_{ms}$ U$_{ms}$ A$_{ms}$ A$_{ms}$ A$_{m}$ | Uniform 2'-OMe | 37.5 | 159 |
| 670747 | $^m$C$_{ks}$ T$_{ks}$ T$_{ds}$ A$_{ds}$ G$_{ks}$ A$_{ds}$ G$_{ds}$ T$_{ks}$ G$_{ds}$ A$_{ds}$ G$_{ks}$ G$_{ds}$ A$_{ds}$ T$_{ks}$ T$_{ds}$ A$_{ds}$ A$_{ks}$ A$_{k}$ | cEt/DNA | 2.4 | 125 |
| 670742 | T$_{ks}$ A$_{ds}$ G$_{ds}$ A$_{ks}$ G$_{ds}$ T$_{ds}$ G$_{ks}$ A$_{ds}$ G$_{ds}$ G$_{ks}$ A$_{ds}$ T$_{ds}$ T$_{ks}$ A$_{ds}$ A$_{ds}$ A$_{k}$ | cEt/DNA | 19.7 | 160 |
| 670743 | $^m$C$_{ks}$ T$_{ds}$ T$_{ds}$ A$_{ks}$ G$_{ds}$ A$_{ds}$ G$_{ks}$ T$_{ds}$ G$_{ds}$ A$_{ks}$ G$_{ds}$ G$_{ds}$ A$_{ks}$ T$_{ds}$ T$_{ds}$ A$_{k}$ | cEt/DNA | 46.3 | 161 |
| 670748 | $^m$C$_{ks}$ T$_{ks}$ T$_{es}$ A$_{es}$ G$_{ks}$ A$_{es}$ G$_{es}$ T$_{ks}$ G$_{es}$ A$_{es}$ G$_{ks}$ G$_{es}$ A$_{es}$ T$_{ks}$ T$_{es}$ A$_{es}$ A$_{ks}$ A$_{k}$ | cEt/2'-MOE | 7.2 | 125 |
| 670744 | T$_{ks}$ A$_{es}$ G$_{es}$ A$_{ks}$ G$_{es}$ T$_{es}$ Gks A$_{es}$ G$_{es}$ G$_{ks}$ A$_{es}$ T$_{es}$ T$_{ks}$ A$_{es}$ A$_{es}$ A$_{k}$ | cEt/2'-MOE | 54.8 | 160 |
| 670745 | $^m$C$_{ks}$ T$_{es}$ T$_{es}$ A$_{ks}$ G$_{es}$ A$_{es}$ G$_{ks}$ T$_{es}$ G$_{es}$ A$_{ks}$ G$_{es}$ G$_{es}$ A$_{ks}$ T$_{es}$ T$_{es}$ A$_{k}$ | cEt/2'-MOE | 9.5 | 161 |

TABLE 32

Effects of non-uniformly modified oligonucleotides on human HNRNPH1 expression

| ISIS No. | Sequence 5' to 3' | Motif | IC$_{50}$ (nM) | SEQ ID No. |
|---|---|---|---|---|
| 580038, Parent | A$_{es}$ G$_{es}$ $^m$C$_{es}$ A$_{es}$ A$_{es}$ A$_{es}$ $^m$C$_{es}$ T$_{es}$ G$_{es}$ $^m$C$_{es}$ A$_{es}$ $^m$C$_{es}$ G$_{es}$ A$_{es}$ A$_{es}$ G$_{es}$ G$_{es}$ $^m$C$_{e}$ | Uniform 2'-MOE | 20.3 | 87 |
| 670725 | A$_{es}$ A$_{es}$ G$_{es}$ $^m$C$_{es}$ A$_{es}$ A$_{ds}$ A$_{ds}$ $^m$C$_{ds}$ T$_{ds}$ G$_{ds}$ $^m$C$_{ds}$ A$_{ds}$ $^m$C$_{ds}$ G$_{ds}$ A$_{ds}$ A$_{es}$ G$_{es}$ G$_{es}$ $^m$C$_{es}$ $^m$C$_{e}$ | Gapmer | 0.9 | 162 |
| 671132 | A$_{ms}$ G$_{ms}$ C$_{ms}$ A$_{ms}$ A$_{ms}$ A$_{ms}$ C$_{ms}$ U$_{ms}$ G$_{ms}$ C$_{ms}$ A$_{ms}$ C$_{ms}$ G$_{ms}$ A$_{ms}$ A$_{ms}$ G$_{ms}$ G$_{ms}$ C$_{m}$ | Uniform 2'-OMe | ND | 163 |
| 670723 | A$_{ks}$ G$_{ks}$ $^m$C$_{ds}$ A$_{ds}$ A$_{ks}$ A$_{ds}$ $^m$C$_{ds}$ T$_{ks}$ G$_{ds}$ $^m$C$_{ds}$ A$_{ks}$ $^m$C$_{ds}$ G$_{ds}$ A$_{ks}$ A$_{ds}$ G$_{ds}$ G$_{ks}$ $^m$C$_{k}$ | cEt/DNA | 7.1 | 87 |

TABLE 32-continued

Effects of non-uniformly modified oligonucleotides on human HNRNPH1 expression

| ISIS No. | Sequence 5' to 3' | Motif | IC$_{50}$ (nM) | SEQ ID No. |
|---|---|---|---|---|
| 670718 | $^mC_{ks}$ A$_{ds}$ A$_{ds}$ A$_{ks}$ $^mC_{ds}$ T$_{ds}$ G$_{ds}$ $^mC_{ds}$ A$_{ds}$ $^mC_{ks}$ G$_{ds}$ A$_{ds}$ A$_{ks}$ G$_{ds}$ G$_{ds}$ $^mC_k$ | cEt/DNA | 11.0 | 164 |
| 670719 | A$_{ks}$ G$_{ds}$ $^mC_{ds}$ A$_{ks}$ A$_{ds}$ A$_{ds}$ $^mC_{ks}$ T$_{ds}$ G$_{ds}$ $^mC_{ks}$ A$_{ds}$ $^mC_{ds}$ G$_{ks}$ A$_{ds}$ A$_{ds}$ G$_k$ | cEt/DNA | 11.2 | 165 |
| 670724 | A$_{ks}$ G$_{ks}$ $^mC_{es}$ Aes A$_{ks}$ A$_{es}$ $^mC_{es}$ T$_{ks}$ G$_{es}$ $^mC_{es}$ A$_{ks}$ $^mC_{es}$ G$_{es}$ A$_{ks}$ A$_{es}$ G$_{es}$ G$_{ks}$ $^mC_k$ | cEt/2'-MOE | 8.0 | 87 |
| 670720 | mC$_{ks}$ A$_{es}$ A$_{es}$ A$_{ks}$ $^mC_{es}$ T$_{es}$ G$_{ks}$ $^mC_{es}$ A$_{es}$ $^mC_{ks}$ G$_{es}$ A$_{es}$ A$_{ks}$ G$_{es}$ G$_{es}$ $^mC_k$ | cEt/2'-MOE | 13.9 | 164 |
| 670721 | A$_{ks}$ G$_{es}$ $^mC_{es}$ A$_{ks}$ A$_{es}$ A$_{es}$ $^mC_{ks}$ T$_{es}$ G$_{es}$ $^mC_{ks}$ A$_{es}$ $^mC_{es}$ G$_{ks}$ A$_{es}$ A$_{es}$ G$_k$ | cEt/2'-MOE | 20.3 | 165 |
| 580027, Parent | $^mC_{es}$ $^mC_{es}$ A$_{es}$ $^mC_{es}$ $^mC_{es}$ G$_{es}$ G$_{es}$ $^mC_{es}$ A$_{es}$ A$_{es}$ T$_{es}$ G$_{es}$ T$_{es}$ T$_{es}$ A$_{es}$ T$_{es}$ $^mC_{es}$ $^mC_e$ | Uniform 2'-MOE | 12.2 | 76 |
| 670733 | T$_{es}$ $^mC_{es}$ $^mC_{es}$ A$_{es}$ $^mC_{es}$ $^mC_{ds}$ G$_{ds}$ G$_{ds}$ $^mC_{ds}$ A$_{ds}$ A$_{ds}$ T$_{ds}$ G$_{ds}$ T$_{ds}$ T$_{ds}$ A$_{es}$ T$_{es}$ $^mC_{es}$ $^mC_{es}$ $^mC_e$ | Gapmer | 3.4 | 166 |
| 671133 | C$_{ms}$ C$_{ms}$ A$_{ms}$ C$_{ms}$ C$_{ms}$ G$_{ms}$ G$_{ms}$ C$_{ms}$ A$_{ms}$ A$_{ms}$ U$_{ms}$ G$_{ms}$ U$_{ms}$ U$_{ms}$ A$_{ms}$ U$_{ms}$ C$_{ms}$ C$_m$ | Uniform 2'-OMe | 35.0 | 167 |
| 670731 | $^mC_{ks}$ $^mC_{ks}$ A$_{ds}$ $^mC_{ds}$ $^mC_{ks}$ G$_{ds}$ G$_{ds}$ $^mC_{ks}$ A$_{ds}$ A$_{ds}$ T$_{ks}$ G$_{ds}$ T$_{ds}$ T$_{ks}$ A$_{ds}$ T$_{ds}$ $^mC_{ks}$ $^mC_k$ | cEt/DNA | 0.8 | 76 |
| 670726 | A$_{ks}$ $^mC_{ds}$ $^mC_{ds}$ G$_{ks}$ G$_{ds}$ $^mC_{ds}$ A$_{ks}$ A$_{ds}$ T$_{ds}$ G$_{ks}$ T$_{ds}$ T$_{ds}$ A$_{ks}$ T$_{ds}$ $^m$Cds $^mC_k$ | cEt/DNA | 11.1 | 168 |
| 670727 | $^mC_{ks}$ $^mC_{ds}$ A$_{ds}$ $^mC_{ks}$ $^mC_{ds}$ G$_{ds}$ G$_{ks}$ $^mC_{ds}$ A$_{ds}$ A$_{ks}$ T$_{ds}$ G$_{ds}$ Tks T$_{ds}$ A$_{ds}$ T$_k$ | cEt/DNA | 32.8 | 169 |
| 670732 | $^mC_{ks}$ $^mC_{ks}$ A$_{es}$ $^mC_{es}$ $^mC_{ks}$ G$_{es}$ G$_{es}$ $^mC_{ks}$ A$_{es}$ A$_{es}$ T$_{ks}$ G$_{es}$ T$_{es}$ T$_{ks}$ A$_{es}$ T$_{es}$ $^mC_{ks}$ $^mC_k$ | cEt/2'-MOEND | | 76 |
| 670728 | A$_{ks}$ $^mC_{es}$ $^mC_{es}$ G$_{ks}$ G$_{es}$ $^mC_{es}$ A$_{ks}$ A$_{es}$ T$_{es}$ G$_{ks}$ T$_{es}$ T$_{es}$ A$_{ks}$ T$_{es}$ $^mC_{es}$ $^mC_k$ | cEt/2'-MOEND | | 168 |
| 670729 | $^mC_{ks}$ $^mC_{es}$ A$_{es}$ $^mC_{ks}$ $^mC_{es}$ G$_{es}$ G$_{ks}$ $^mC_{es}$ A$_{es}$ A$_{ks}$ T$_{es}$ G$_{es}$ T$_{ks}$ T$_{es}$ A$_{es}$ T$_k$ | cEt/2'-MOEND | | 169 |

Example 21

Evaluation of Uniform 2'-MOE Modified Oligonucleotides in Liver Targeting Mouse STAT3—In Vivo Study ISIS 580771 and 580783 (see Table 17), which target exon 17, were evaluated for their effects on inhibition of mouse STAT3 in the liver in vivo. The 5-10-5 MOE gapmer ISIS 383741 (see Table 17) was included as a positive control.

6 week old Balb/c mice were subcutaneously injected with 50 mg/kg modified oligonucleotide or PBS twice per week for 3 weeks (a total of 7 doses). Each treatment group consisted of 4 animals.

The animals were sacrificed 48 hours following the last injection. The liver tissue was homogenized, RNA was isolated, and STAT3 RNA expression levels were measured by qRT-PCR using primer probe set RTS2381 (see Example 12). Exon 17 skipping was assessed using methods similar to those in Example and primer set forward primer to exon 16 (5'-ACTCCTTGCCAGTTGTGGTGATCT-3' SEQ ID NO: 170) and reverse primer to exon 18 (5'-TTAGCCCATGTGATCTGACACCCT-3' SEQ ID NO: 171). The results of the exon 17 skipping experiment showed that ISIS 580771 and 580783 cause exon 17 skipping, whereas PBS and the gapmer ISIS 383741 did not (data not shown).

The results presented in Table 33 are the average percent of liver STAT3 RNA levels for each treatment group, normalized to the PBS treated control group and is denoted as "% PBS".

TABLE 33

Effects of modified oligonucleotides on liver STAT3 expression in vivo

| ISIS No. | STAT3 RNA (% PBS) | SEQ ID No. |
|---|---|---|
| 580771 | 67 | 114 |
| 580783 | 66 | 117 |
| 383741 | 14 | 109 |

We claim:

1. A method of reducing the amount or activity of a target mRNA that encodes a protein selected from STAT3, SOD1, and HNRNPH1 in a cell through nonsense mediated decay, comprising contacting a cell with an oligomeric compound comprising a modified oligonucleotide, wherein:

the modified oligonucleotide consists of 10 to 30 linked nucleosides, wherein each nucleoside of the modified oligonucleotide comprises a 2'-MOE modified nucleoside; or the modified oligonucleotide has an $A-B_2-A-B_2-A-B_2-A-B_2-A-B_2-A$ motif or an $A_2-B_2-A-B_2-A-B_2-A-B_2-A-B_2-A_2$ motif, wherein each A comprises a bicyclic sugar moiety, and wherein each B comprises a sugar moiety selected from a 2'-substituted sugar moiety and an unmodified 2'-deoxy sugar moiety, wherein each internucleoside linkage in the modified oligonucleotide is a phosphorothioate internucleoside linkage, and wherein the modified oligonucleotide is at least 90% complementary to a pre-mRNA corresponding to the target mRNA;

wherein the oligomeric compound increases exclusion of an exon from the target mRNA and thereby introduces a premature termination codon in the target mRNA; and wherein the target mRNA with the premature termination codon is recognized by the nonsense mediated decay mechanism, thereby reducing the amount or activity of the target mRNA in the cell through nonsense mediated decay.

2. The method of claim 1, wherein each modified nucleoside comprises a 2'-MOE sugar moiety.

3. The method of claim 1, wherein the modified oligonucleotide has an $A-B_2-A-B_2-A-B_2-A-B_2-A-B_2-A$ motif, wherein each A comprises a bicyclic sugar moiety, and wherein each B comprises a sugar moiety selected from a 2'-substituted sugar moiety and an unmodified 2'-deoxy sugar moiety.

4. The method of claim 1, wherein each A comprises a cEt sugar moiety or an LNA sugar moiety.

5. The method of claim 3, wherein each A comprises a cEt sugar moiety or an LNA sugar moiety.

6. The method of claim 1, wherein each B comprises an unmodified 2'-deoxy sugar moiety or a 2'-MOE sugar moiety.

7. The method of claim 3, wherein each B comprises an unmodified 2'-deoxy sugar moiety or a 2'-MOE sugar moiety.

8. The method of claim 1, wherein the cell is in an animal.

9. The method of claim 4, wherein each B comprises an unmodified 2'-deoxy sugar moiety.

10. The method of claim 5, wherein each B comprises an unmodified 2'-deoxy sugar moiety.

11. The method of claim 1, wherein the modified oligonucleotide has an $A_2-B_2-A-B_2-A-B_2-A-B_2-A-B_2-A_2$ motif, wherein each A comprises a bicyclic sugar moiety, and wherein each B comprises a sugar moiety selected from a 2'-substituted sugar moiety and an unmodified 2'-deoxy sugar moiety.

12. The method of claim 1, wherein each cytosine in the modified oligonucleotide is a 5-methyl cytosine.

* * * * *